(12) United States Patent
Bakthavatchalam et al.

(10) Patent No.: US 6,448,261 B1
(45) Date of Patent: Sep. 10, 2002

(54) ARYLAMINO FUSED PYRIDINES

(75) Inventors: Rajagopal Bakthavatchalam, Wilmington, DE (US); Argyrios Georgios Arvanitis, Kennett Square, PA (US); James Peter Beck, Smyrna; Gary Avonn Cain, Wilmington, both of DE (US); Robert John Chorvat, West Chester, PA (US); Paul Joseph Gilligan; Richard Eric Olson, both of Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/525,619

(22) Filed: Mar. 14, 2000

Related U.S. Application Data

(62) Division of application No. 08/823,029, filed on Mar. 21, 1997.
(60) Provisional application No. 60/014,157, filed on Mar. 27, 1996, provisional application No. 60/030,536, filed on Oct. 31, 1996, and provisional application No. 60/039,124, filed on Feb. 25, 1997.

(51) Int. Cl.$^7$ ..................... A61K 31/44; C07D 221/00; C07D 471/02
(52) U.S. Cl. ................ 514/300; 514/303; 546/112; 546/113; 546/114; 546/115; 546/118; 546/119
(58) Field of Search ................ 546/113, 112, 546/114, 115, 118, 119; 514/300, 303

(56) References Cited

U.S. PATENT DOCUMENTS 4,076,711 A    2/1978  Ganguly et al. ......... 260/256.4

FOREIGN PATENT DOCUMENTS

| EP | 778277 | * | 6/1997 |
| WO | 9533727 | | 12/1995 |
| WO | 9534563 | | 12/1995 |

OTHER PUBLICATIONS

"Imidazo(4,5–c)pyridines . . . & their . . . antiinfla, agts."Th.A.Krentsky et al.,J.Med.Ch.29/1,138–43, Jan. 1986.*
Svertilova et al,Ukr.Khim.Zh.;62/3–4,64–69(1996);Synthesis of 4–arylamino & 4–alkylamino–imidazoo–pyridines and 1,2,3–triazolo–pyridines.*
Krenitsky et al,;J.Med.Chem.29/1,138–43;"Imidazopuridines and their nucleosides as immunosupressive and antiinf.".*
J. Rivier et al., *Proc. Natl. Acad. Sci.*, 80:4851 (1983).
W. Vale et al., *Science*, 213:1394 (1981).
W. Vale et al., *Rec. Prog. Horm. Res.*, 39:245 (1983).
G.F. Koob, *Persp. Behav. Med.*, 2:39 (1985).
E.B. De Souza et al., *J. Neurosci.*, 5:3189 (1985).
J.E. Blalock, *Physiological Reviews*, 69:1 (1989).
J.E. Morley, *Life Sci.*, 41:527 (1987).
E.B. DeSouza, *Hosp. Practice*, 23:59 (1988).
C.B. Nemeroff et al., *Science*, 226:1342 (1984).
C.M. Banki et al., *Am. J. Psychiatry*, 144:873 (1987).
R.D. France et al., *Biol. Psychiatry*, 23:86 (1988).
M. Arato et al., *Biol. Psychiatry*, 25:355 (1989).
C.B. Nemeroff et al., *Arch. Gen. Psychiatry*, 45:577 (1988).
P.W. Gold et al., *Am. J. Psychiatry*, 141:619 (1984).
F. Holsboer et al., *Psychoneuroendocrinology*, 9:147 (1984).
P.W. Gold et al., *New Eng. J. Med.*, 314:1129 (1986).
R.M. Sapolsky, *Arch. Gen. Psychiatry*, 46:1047 (1989).
Grigoriadis et al., *Neuropsychopharmacology*, 2:53 (1989).
D.R. Britton et al., *Life Sci.*, 31:363 (1982).
C.W. Berridge & A.J. Dunn, *Requl. Peptides*, 16:83 (1986).
C.W. Berridge & A.J. Dunn, *Horm. Behav.*, 21:393 (1987).
*Brain Research Reviews*, 15:71 (1990) A. J. Dunn et al.
K. T. Britton et al., *Psychopharmacology*, 86:170 (1985).
N.R. Swerdlow et al., *Psychopharmacology*, 88:147 (1986).
K.T. Britton et al., *Psychopharmacology*, 94:306 (1988).
G.F. Koob & K.T. Britton, *Corticotropin–Releasing Factor: Basic & Clinical Studies of a Neuropeptide*, E.B. DeSouza & C.B. Nemeroff, CRC Press, p. 221 (1990).
*Remington's Pharmaceutical Sciences*, 17$^{th}$ ed., Mack Pub. Co., Easton, PA, p. 1418 (1985).
Albert, Brown & Wood, *J. Chem. Soc.*, 3832 (1954).
Munson & Rodbard, *Anal. Biochem.*, 107:220 (1980).
Tanji et al., *Chem. Pharm. Bull.*, 39(11), 3037–3040 (1991).
Settimo et al., *Il Farmaco*, Ed. Sc., 35(4), 308–323 (1980).
Biagi et al., *Il Farmaco*, 49(3), 183–186 (1994).
Thompson et al., *J. Med. Chem.*, 34, 2877–2882 (1991).
Kelley et al., *J. Med. Chem.*, 31, 606–612 (1990).
Kelley et al., *J. Med. Chem.*, 33, 1360–1363 (1990).
Kelley et al., *J. Heterocyclic Chem.*, 28, 1099 (1991).
Khairy et al., *J. Heterocyclic Chem.*, 22, 853 (1985).

* cited by examiner

Primary Examiner—Mukund J. Shah
Assistant Examiner—Sudhaker B. Patel
(74) Attorney, Agent, or Firm—Kenneth B. Rubin; Kalim S. Fuzail

(57) ABSTRACT

Corticotropin releasing factor (CRF) antagonists of formula I;

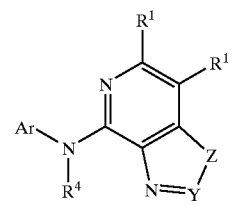

and their use in treating anxiety, depression, and other psychiatric and neurological disorders.

9 Claims, No Drawings

ARYLAMINO FUSED PYRIDINES

This application is a division of U.S. Ser. No. 08/823,029, filed Mar. 21, 1997 now allowed U.S. Pat. No. 6,107,300 on Aug. 22, 2000, which in turn claims the benefit of filing of U.S. Provisional Application No. 60/014,157, filed Mar. 27, 1996, U.S. Provisional Application No. 60/030,536, filed Oct. 31, 1996 and U.S. Provisional Application No. 60/039,124, filed Feb. 25, 1997.

FIELD OF THE INVENTION

This application is a division of U.S. Ser. No. 08/823,029, filed Mar. 21, 1997, which-in-turn claims the benefit of the filing of U.S. Provisional Application No. 60/014,157, filed Mar. 27, 1996, U.S. Provisional Application No. 60/030,536, filed Oct. 31, 1996 and U.S. Provisional Application No. 60/039,124, filed Feb. 25, 1997. This invention relates to novel compounds and pharmaceutical compositions, and to methods of using same in the treatment of psychiatric disorders and neurological diseases including major depression, anxiety-related disorders, post-traumatic stress disorder, supranuclear palsy and feeding disorders.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., *Proc. Nat. Acad. Sci.* (*USA*) 80:4851 (1983); W. Vale et al., *Science* 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J.E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

DuPont Merck PCT application US94/11050 describes corticotropin releasing factor antagonist compounds of the formula:

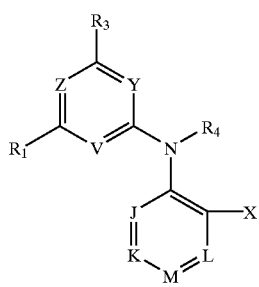

and their use to treat psychiatric disorders and neurological diseases. Included in the description are fused pyridines and pyrimidines of the formula:

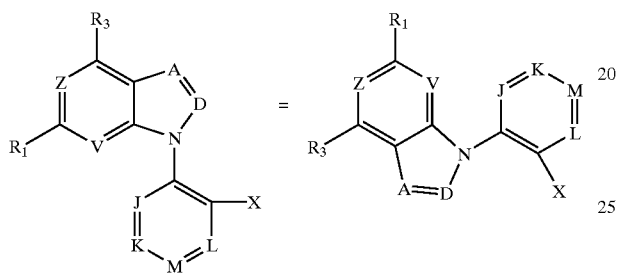

Where:
V is $CR^{1a}$ or N; Z is $CR^2$ or N; A is $CR^{30}$ or N; and D is $CR^{28}$ or N.

Pfizer WO 95/33750 describes corticotropin releasing factor antagonist compounds useful in the treatment of CNS and stress disorders. The description includes compounds of the formulae:

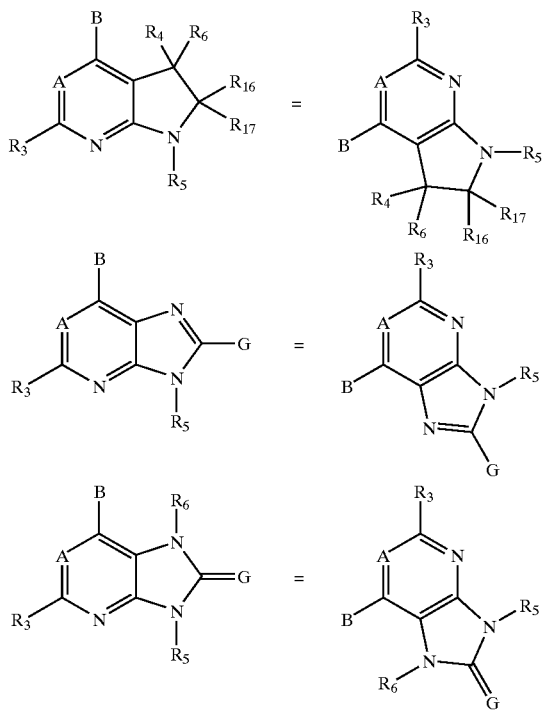

where A is $CR_7$ or N; B is $—NR_1R_2$; $R_1$ is substituted or unsubstituted alkyl; $R_2$ is substituted or unsubstituted alkyl, aryl or heteroaryl; $R_3$ is methyl, halo, cyano, methoxy, etc.; $R_4$ is H, substituted or unsubstituted alkyl, halo, amino, nitro, etc.; $R_5$ is substituted or unsubstituted aryl or heteroaryl; $R_6$ is H or substituted or unsubstituted alkyl; $R_7$ is H, methyl, halo, cyano, etc.; $R_{16}$ and $R_{17}$ taken together form an oxo (=O) group; and G is =O, =S, =NH, =NCH$_3$, hydrogen, methyl, methoxy, etc. Pfizer WO 95/33750 also describes intermediates of the formula:

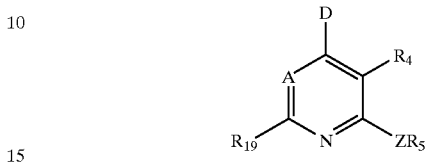

where A can be N, D can be OH, $R_4$ can be nitro, $R_{19}$ is methyl or ethyl, Z can be NH or N(CH$_3$), and $R_5$ is substituted phenyl or substituted pyridyl, each substituted with 2 or 3 substituents selected from $C_1$–$C_4$ alkyl, chloro and bromo.

Pfizer WO 95/34563 describes corticotropin releasing factor antagonist compounds, including compounds of the formula:

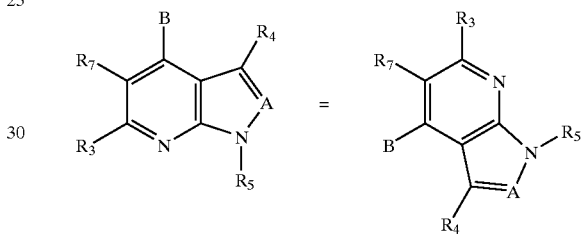

where A, B and the R groups have definitions similar to those in WO 95/33750.

Pfizer WO 95/33727 describes corticotropin releasing factor antagonist compounds of the formula:

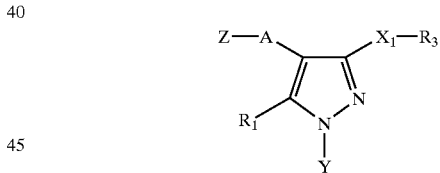

where A is CH$_2$ and Z can be a heteroaryl moiety.

Ganguly et al., U.S. Pat. No. 4,076,711 describes triazolo [4,5-d]pyrimidines of the formula:

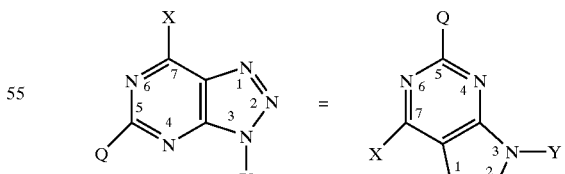

where X is halo, $—NR_1R$ or alkoxy, with R1 and R each being H or alkyl; Y is alkyl, cycloalkyl, hydroxycycloalkyl, phenyl, bicycloalkyl or phenylalkyl or bicycloalkylalkyl; and Q is H or Y. The patent states that the compounds are useful in the treatment of psoriasis.

Tanji et al., Chem. Pharm. Bull. 39(11)3037–3040 (1991), describes triazolo[4,5-d]pyrimidines of the formula:

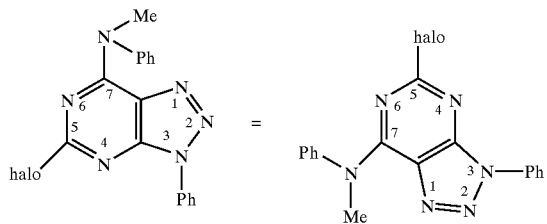

where halo is I, Br or Cl, Ph is phenyl and Me is methyl. No utility for the compounds is described.

Settimo et al., Il Farmaco, Ed. Sc., 35 (4), 308–323 (1980) describes 8-azaadenines (triazolo[4,5-d] pyrimidines) of the formula:

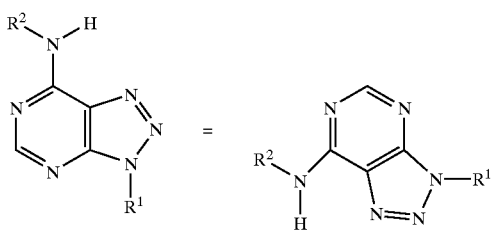

where R1 is H or benzyl and R2 is p-methylphenyl.

Biagi et al., Il Farmaco, 49 (3), 183–186, (1994), describes N(6)-substituted 2-n-butyl-9-benzyl-8-azaadenines of the formula:

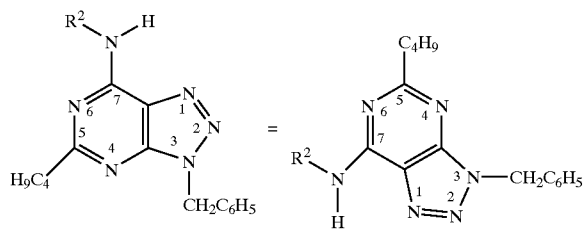

where $R^2$ can be alkyl, phenyl, or benzyl. The paper states that the compounds have affinity for adenosine receptors.

Thompson et al., J. Med. Chem., 1991, 34, 2877–2882, describes $N^6$,9-disubstituted adenines of the formula:

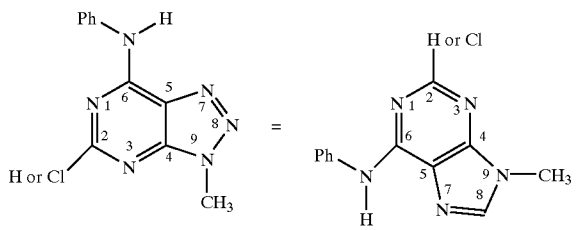

where Ph is phenyl or (when C-2 is unsubstituted) 2-fluorophenyl. The paper states that the compounds have selective affinity for the $A_1$ adenosine receptor.

Kelley et al., J. Med. Chem. 1990, 31, 606–612, describes the compound

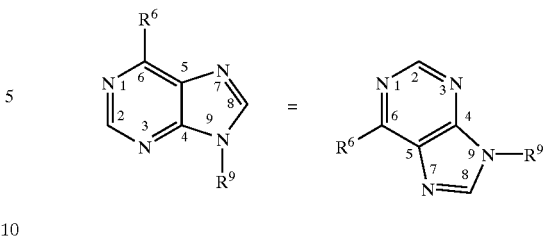

where $R^6$ is $NHC_6H_5$ and $R^9$ is $CH_2C_6H_5$, and reports that the compound was inactive when tested for anticonvulsant activity. The paper reports that various 6-(alkylamino)-9-benzyl-9H-purine analogs of the above compound exhibited anticonvulsant activity.

Kelley et al., J. Med. Chem. 1990, 33, 1360–1363, describes 6-anilino-9-benzyl-2-choro-9H-purines of the formula:

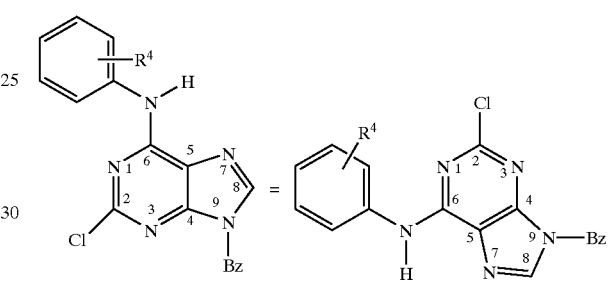

where Bz is benzyl or (when $R^4$ is H) p-methylbenzyl and $R^4$ is H or alkyl, alkoxy, halo, cyano, nitro, etc. Tests of the compounds for antirhinoviral activity are reported.

Kelley et al., J. Heterocyclic Chem., 28, 1099 (1991), describes 6-substituted-9-(3-formamidobenzyl)-9H-purines of the formula:

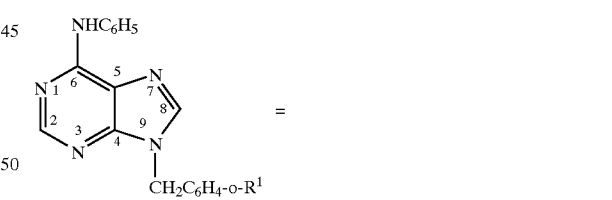

where R1 is NH2 or NHCHO. The compound where R1 is NHCHO was tested for benzodiazepine receptor binding and was inactive, although various analogs were active.

Khairy et al., J. Heterocyclic Chem., 22, 853 (1985), describes synthesis of certain 9-aryl-9H-purin-6-amines of the formula:

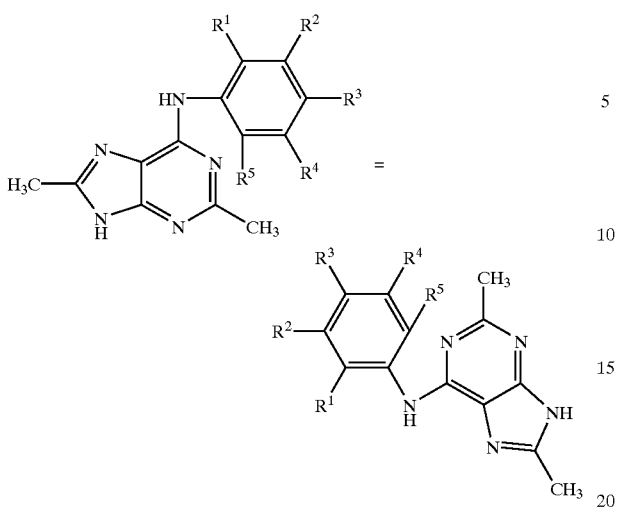

where the R groups are H, methyl, ethyl, isopropyl, chloro or fluoro.

SUMMARY OF THE INVENTION

This invention is a class of novel compounds which are CRF receptor antagonists and which can be represented by formula I or formula II:

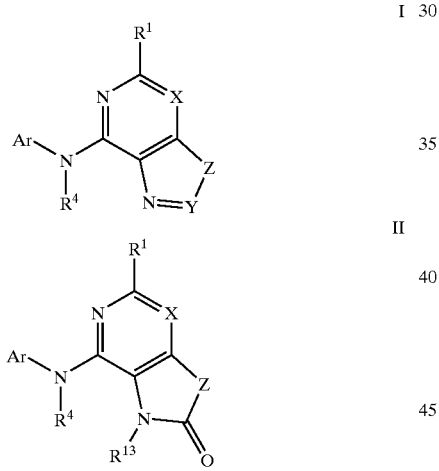

or a pharmaceutically acceptable salt or pro-drug form thereof, wherein:

X is N or $CR^1$;

Y is N or $CR^2$;

Z is $NR^3$, O, or $S(O)_n$;

G is O or S;

Ar is phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each optionally substituted with 1 to 5 $R^5$ groups;

$R^1$ is independently at each occurrence H, $C_1$–$C_4$ alkyl, $C_2$–$C_4$ alkenyl, $C_2$–C4 alkynyl, halo, CN, $C_1$–$C_4$ haloalkyl, —$NR^9R^{10}$, $NR^9COR^{10}$, —$OR^{11}$, SH or —$S(O)_nR^{12}$;

$R^2$ is H, $C_1$–$C_4$ alkyl, $C_1$–$C_6$ cycloalkyl, halo, CN, —$NR^6R^7$, $NR^9COR^{10}$, $C_1$–$C_4$ haloalkyl, —$OR^7$, SH or —$S(O)_nR^{12}$;

$R^3$ is H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —OC(O)$R^{13}$, —$NR^8COR^7$, —N(COR$^7$)$_2$, —$NR^8CONR^6R^7$, —$NR^8CO_2R^{13}$, —$NR^6R^7$, —$CONR^6R^7$, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, -$CO_2R^7$, —OC(O)$R^{13}$, —$NR^8COR^7$, —N(COR$^7$)$_2$, —$NR^8CONR^6R^7$, —$NR^8CO_2R^{13}$, —$NR^6R^7$, and —$CONR^6R^7$;

$R^4$ is H, $C_1$–$C_4$ alkyl, allyl, or propargyl, where $C_1$–$C_4$ alkyl, allyl, or propargyl is optionally substituted with $C_3$–$C_6$ cycloalkyl and where $C_1$–$C_4$ alkyl is optionally substituted with, —$OR^7$, —$S(O)_nR^{12}$ or —$CO_2R^7$;

$R^5$ is independently at each occurrence $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halo, —CN, $C_1$–$C_4$ haloalkyl, —$NR^6R^7$, $NR^8COR^7$, $NR^8CO_2R^7$, —$COR^7$ —$OR^7$, —$CONR^6R^7$, —CO(NOR$^9$)$R^7$, $CO_2R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, —$NR^6R^7$, $NR^8COR^7$, $NR^8CO_2R^7$, —$COR^7$ —$OR^7$, —$CONR^6R^7$, $CO_2R^7$, —CO(NOR$^9$)$R^7$, or —$S(O)_nR^7$;

$R^6$ and $R^7$ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence H or $C_1$–$C_4$ alkyl;

$R^9$ and $R^{10}$ are independently at each occurrence selected from H, $C_1$–$C_4$ alkyl, or $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl ($C_1$–$C_4$ alkyl)-, heteroaryl or heteroaryl($C_1$–$C_4$ alkyl)-;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR_{13}$, —$COR^7$, —$CO_2R^7$, —OC(O)$R^{13}$, —$NR^8COR^7$, —N(COR$^7$)$_2$, —$NR^8CONR^6R^7$, —$NR^8CO_2R^{13}$, —$NR^6R^7$, and —$CONR^6R^7$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, halo, $C_1$—$C_4$ haloalkyl, cyano, —$OR^7$, SH, —$S(O)_nR^{13}$, —$COR^7$, —$CO_2R^7$, —OC(O)$R^{13}$, —$NR^8COR^7$, —N(COR$^7$)$_2$, —$NR^8CONR6R^7$, —$NR^8CO_2R^{13}$, —$NR^6R^7$, and —$CONR^6R^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

n is independently at each occurrence 0, 1 or 2;

provided that $R^4$ in formula I is not H:

(a) when X is N, Y is N, Z is $NR^3$, $R^1$ is H, $R^3$ is H or benzyl, and Ar is p-methylphenyl;

(b) when X is N, Y is N, Z is $NR^3$, $R^1$ is butyl, $R^3$ is benzyl, and Ar is phenyl;

(c) when X is N, Y is CH, Z is $NR^3$, $R^3$ is methyl, $R^1$ is H, and Ar is phenyl or 2-fluorophenyl;

(d) when X is N, Y is CH, Z is $NR^3$, $R^3$ is methyl, $R^1$ is Cl and Ar is phenyl;

(e) when X is N, Y is CH, Z is $NR^3$, $R^1$ is Cl, $R^3$ is benzyl, and Ar is phenyl or substituted phenyl;

(f) when X is N, Y is CH, Z is $NR^3$, $R^3$ is p-methylbenzyl, and Ar is phenyl;

(g) when X is N, Y is $CR^2$, Z is $NR^3$, $R^2$ is $CH_3$, $R^3$ is H, and Ar is phenyl or phenyl substituted with methyl, ethyl, isopropyl, fluoro or chloro;

(h) when X is N, Y is N, Z is $NR^3$, R3 is cyclopropylmethyl, R1 is H, and Ar is 2-bromo-4-isopropylphenyl, or (i) when X is N, Y is N, Z is S, $R^1$ is H, and Ar is 2-bromo-4-isopropylphenyl.

Preferred compounds of this invention are compounds of formula I and formula II and pharmaceutically acceptable salts and pro-drug forms thereof, wherein, independently or concurrently:

X is N or $CR^1$;

Y is N or $CR^2$;

Z is $NR^3$, O, or $S(O)_n$;

G is O or S;

Ar is phenyl or pyridyl, each optionally substituted with 1 to 3 $R^5$ groups;

$R^1$ is independently at each occurrence H, $C_1$–$C_4$ alkyl, halo, CN, $C_1$–$C_4$ haloalkyl, —$NR^9R^{10}$, —$OR^{11}$ or —$S(O)_nR^{12}$;

$R^2$ is H, $C_1$–$C_4$ alkyl, $C_1$–$C_6$ cycloalkyl, halo, CN, —$NR^6R^7$, $NR^9COR^{10}$, $C_1$–$C_4$ haloalkyl, —$OR^7$ or —$S(O)_nR^{12}$;

$R^3$ is H, $C_1$–$C_{10}$ alkyl, $C_2$–$C_{10}$ alkenyl, $c_2$-$c_{10}$ alkynyl, $C_3$–$C_8$ cycloalkyl or $C_4$–$C_{12}$ cycloalkylalkyl each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, —$S(O)_nR^{13}$, —$CO_2R^7$, —$NR^8COR^7$, —$NR^8CONR^6R^7$, —$NR^8CO_2R^{13}$, —$NR^6R^7$, aryl and heteroaryl, where the aryl or heteroaryl is optionally substituted with 1 to 3 substituents independently selected at each occurrence from $C_1$–$C_4$ alkyl, halo, cyano, —$OR^7$, —$S(O)_nR^7$, —$CO_2R^7$, —$NR^8COR^7$, —$NR^8CONR^6R^7$, —$NR^8CO_2R^7$ and —$NR^6R^7$;

$R^4$ is H, $C_1$–$C_4$ alkyl, allyl, or propargyl;

$R^5$ is independently at each occurrence $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, —$NO_2$, halo, —CN $C_1$–$C_4$ haloalkyl, —$NR^6R^7$, $COR^7$ —$OR^7$, —$CONR^6R^7$, —$CO(NOR^9)R^7$, $CO_2R^7$, or —$S(O)_nR^7$, where $C_1$–$C_6$ alkyl, $C_2$–$C_6$ alkenyl, $C_2$–$C_6$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, $COR^7$, —$OR^7$, —$CONR^6R^7$, $CO_2R^7$, —$CO(NOR^9)R^7$, or —$S(O)_nR^7$;

$R^6$ and R7 are independently at each occurrence H, $C_1$–$C_4$ alkyl, $C_1$–C4 haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence H or $C_1$–$C_4$ alkyl;

$R^9$ and $R^{10}$ are independently at each occurrence selected from H, $C_1$–$C_4$ alkyl, or $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl ($C_1$–$C_4$ alkyl)-, heteroaryl or heteroaryl($C_1$–$C_4$ alkyl)-;

aryl is phenyl or naphthyl optionally substituted with 1 to 3 substituents independently selected at each occurrence from $C_1$–$C_4$ alkyl, halo, cyano, —$OR^7$, —$S(O)_nR^{12}$, —$C_{02}R^8$, —$NR^8COR^7$, —$NR^8CONR^6R^7$, —$NR^8C_2R^{12}$, and -$NR^6R^7$;

heteroaryl is pyridyl, pyrimidinyl, triazinyl, furanyl, thienyl, imidazolyl, thiazolyl, indolyl, pyrrolyl, oxazolyl, isoxazolyl, pyrazolyl, triazolyl, tetrazolyl, or indazolyl, each optionally substituted with 1 to 3 substituents independently selected at each occurrence from $C_1$–$C_4$ alkyl, halo, cyano, —$OR^7$, —$S(O)_nR^{12}$, —$CO_2R^8$, —$NR^8COR^7$, —$NR^8CONR^6R^7$, —$NR^8CO_2R^{12}$, and —$NR^6R^7$;

n is independently at each occurrence 0, 1 or 2.

Of the preferred compounds, more preferred are those of formula I wherein Z is $NR^3$ and pharmaceutically acceptable salts and pro-drug forms thereof.

Included in this invention is the method of treating affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, or fertility problem in a mammal comprising administering to the mammal a therapeutically effective amount of a compound of formula I or II.

Also included in this invention are pharmaceutical compositions comprising a pharmaceutically acceptable carrier and a therapeutically effective amount of any one of the above-described compounds.

This invention also includes intermediate compounds useful in preparation of the CRF antagonist compounds and processes for making those intermediates, as described in the following description and claims.

The CRF antagonist compounds provided by this invention (and especially labelled compounds of this invention) are also useful as standards and reagents in determining the ability of a potential pharmaceutical to bind to the CRF receptor.

DETAILED DESCRIPTION OF INVENTION

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. "Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

The term "pharmaceutically acceptable salts" includes acid or base salts of the compounds of formulas (I) and (II). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal level of CRF or treat the symptoms of affective disorder, anxiety or depression in a host.

Synthesis

The bicylic fused pyrimidine and pyridines of this invention can be prepared by one of the general schemes outlined below (Scheme 1–9).

Compounds of the Formula (I) wherein X=Y=N and Z=NR³, can be prepared as shown in Scheme 1.

(VI). Conditions which may facilitate this transformation include the optional presence of protic or aprotic acids, or bases such as alkali metal hydrides, trialkylamines, or alkali metal carbonates, or alkali metal bis(trimethylsilyl)amides wherein the metal can be sodium, lithium, or potassium. These reactions may be conducted neat, or in the optional presence of solvents such as but not limited to cyclic ethers such as tetrahydrofuran, dialkylformamides, ethylene glycol, 2-ethoxyethanol, halocarbons, alkanenitriles, or alkyl alcohols at room temperature or at elevated temperature up to the boiling point of the solvent employed. One skilled in the art of organic synthesis will readily understand the optimal combinations of these conversions to prepare a number of compounds of Formula (VI). Cyclization to triazolopyrimidines of Formula (VII) can then be readily accomplished by diazotization and cyclization of the diamino compounds of Formula (VI) with an alkali metal

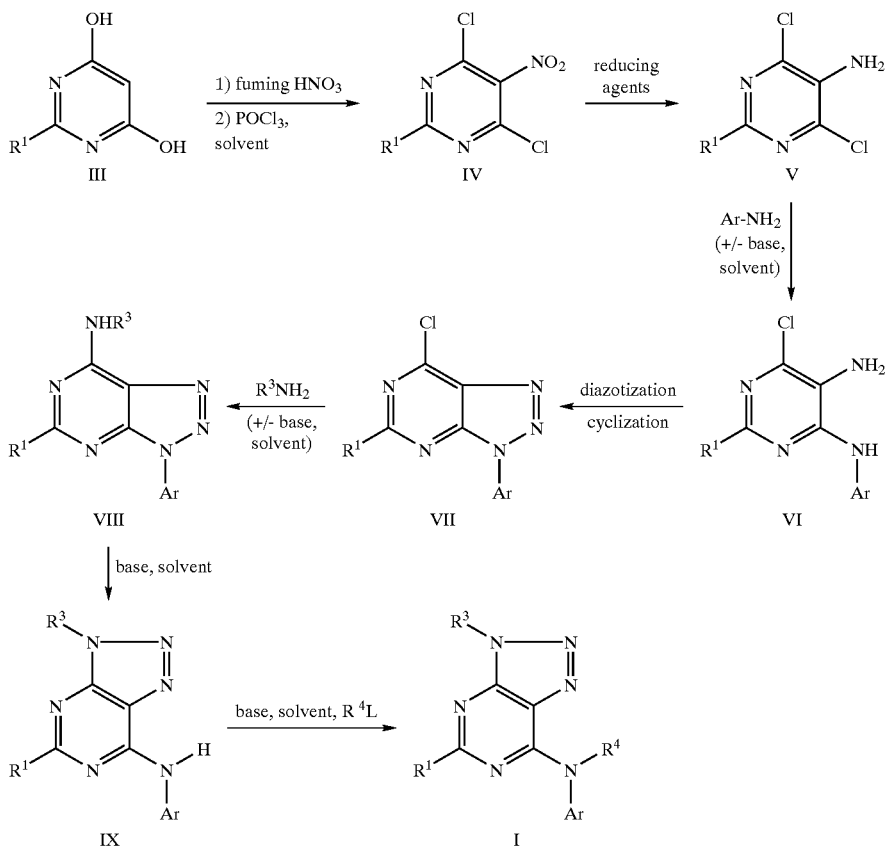

Scheme 1 wherein X=Y=N; Z=NR³

The 4,6-dihydroxypyrimidines (III) can be nitrated using fuming nitric acid and then converted into intermediates (IV) by the action of phosphorous oxychloride with the optional assistance of a catalyst such as dialkylanilines (see: Brown, D. J. et.al. *J. Chem. Soc.*, 1954, 3832). The amino group of pyrimidines of Formula (V) can be prepared from the corresponding nitro compounds (IV) by treatment with reducing agents such as, but not limited to, sodium dithionate, iron or zinc, or catalytic hydrogenation (see: Larock, R. C. *Comprehensive Organic Transformations*, VCH Publishers, New York, 1989, 411). Reaction with Ar—NH₂ can be used to provide compounds of Formula nitrite in the presence of acid in water with or without an organic cosolvent such as halocarbons, or cyclic ethers. Treatment of compound of Formula (VII) with primary amines then can provide the intermediates (VIII) using reaction conditions similar to those employed for the conversion of (V) to (VI). The rearranged triazolopyrimidine of Formula (IX) may be obtained from the triazolopyrimidine of Formula (VIII) by treatment with base such as but not limited to, alkali metal hydrides, alkaline earth metal hydrides, alkali metal dialkyl amides in inert solvents such as dialkylformamides, dialkylacetamides at temperatures ranging from 0° to 200° C. Finally, reaction with an appropriate R⁴L wherein L is a suitable leaving group such as halo, methanesulfonate, p-toluenesulfonate, or triflate in the presence or absence of bases such as but not limited to, alkali metal hydrides, alkaline earth metal hydrides, alkali metal dialkyl amides in inert solvents such as dialkylformamides or dialkylacetamides at temperatures ranging from 0° to 200° C. can be used to generate compounds of Formula (I).

Alternatively, compounds of Formula (I) wherein X=Y=N and Z=NR$^3$, of this invention can be prepared as outlined in Scheme 2:

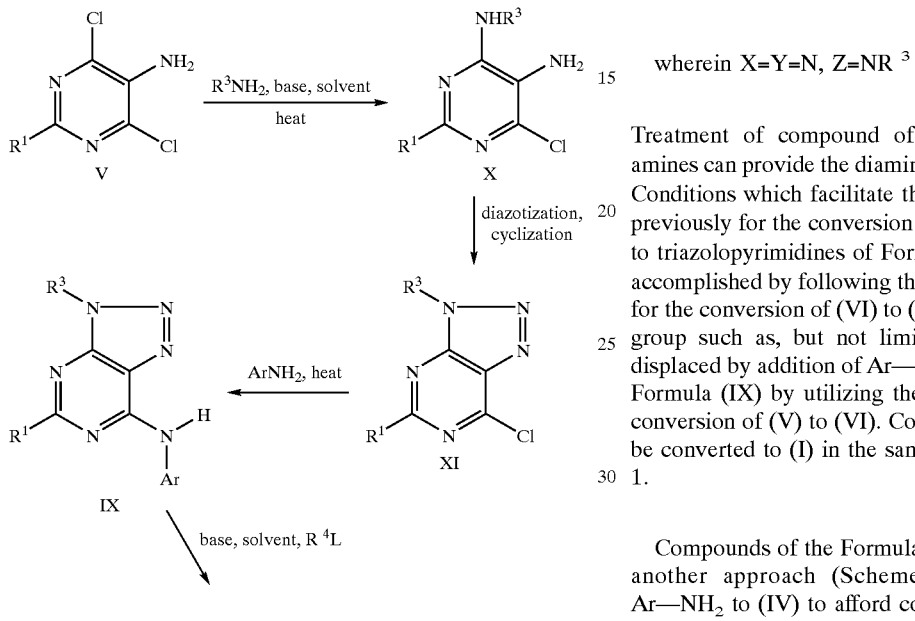

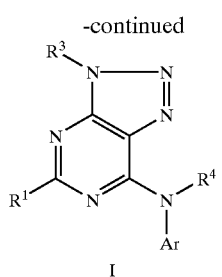

wherein X=Y=N, Z=NR $^3$

Treatment of compound of Formula (V) with primary amines can provide the diamino substituted pyrimidines (X). Conditions which facilitate this transformation are detailed previously for the conversion of (VII) to (VIII). Cyclization to triazolopyrimidines of Formula (XI) can then be readily accomplished by following the conditions already described for the conversion of (VI) to (VII) in Scheme 1. The leaving group such as, but not limited to, halogen can then be displaced by addition of Ar—NH$_2$ to provide compounds of Formula (IX) by utilizing the conditions described for the conversion of (V) to (VI). Compounds of Formula (IX) can be converted to (I) in the same way as outlined in Scheme 1.

Compounds of the Formula (VI) can also prepared by an another approach (Scheme 3) involving addition of Ar—NH$_2$ to (IV) to afford compounds of Formula (XII).

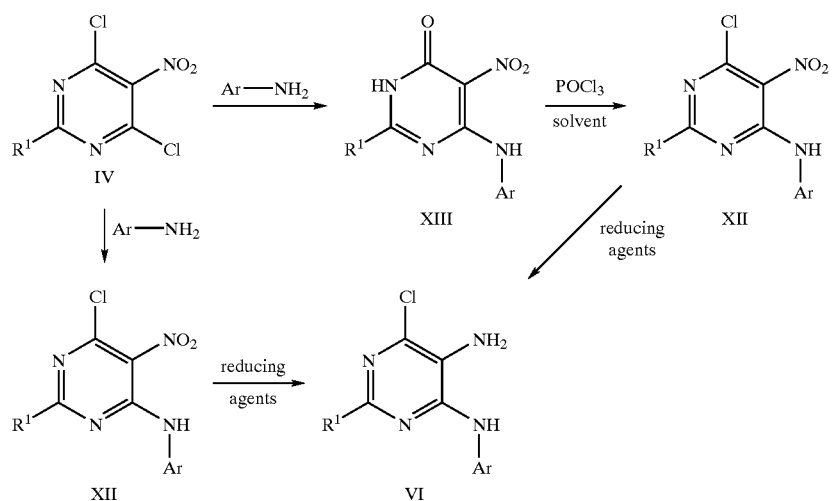

The nitro group in (XII) can be reduced to give compounds of Formula (VI) under conditions similar to those described for the transformation of (IV) to (V) in Scheme 1. Alternatively, as shown in Scheme 3, addition of Ar—NH$_2$ to compounds of Formula (IV) can generate in-situ the pyrimidones (XIII). For example, treatment of dichloropyrimidines of Formula (IV) with one equivalent of Ar—NH$_2$ in the presence of solvents such as (but not limited to) dialkylsulfoxides, dialkylformamides, and alkyl alcohols-readily generate pyrimidones (XIII). Compounds of Formula (XIII) can be converted into (IV) by the action of phosphorous oxychloride with the optional assistance of a catalyst such as dialkylanilines with or without an inert solvent. Compounds of Formula (VI) are elaborated to structures of Formula (I) as previously shown in Scheme 1.

Scheme 4 outlines another route to fused triazolopyrimidine type of compounds of this invention.

base such as but not limited to, alkali metal hydrides, alkaline earth metal hydrides, alkali metal dialkyl amides in an inert solvent. Compounds of Formula (IX) are elaborated to give (I) as delineated in Scheme 1.

Fused imidazolopyrimidines of the Formula (I) wherein X=N, Y=CR$^2$, and Z=NR$^3$, can be prepared from compound (X) as shown in Scheme 5.

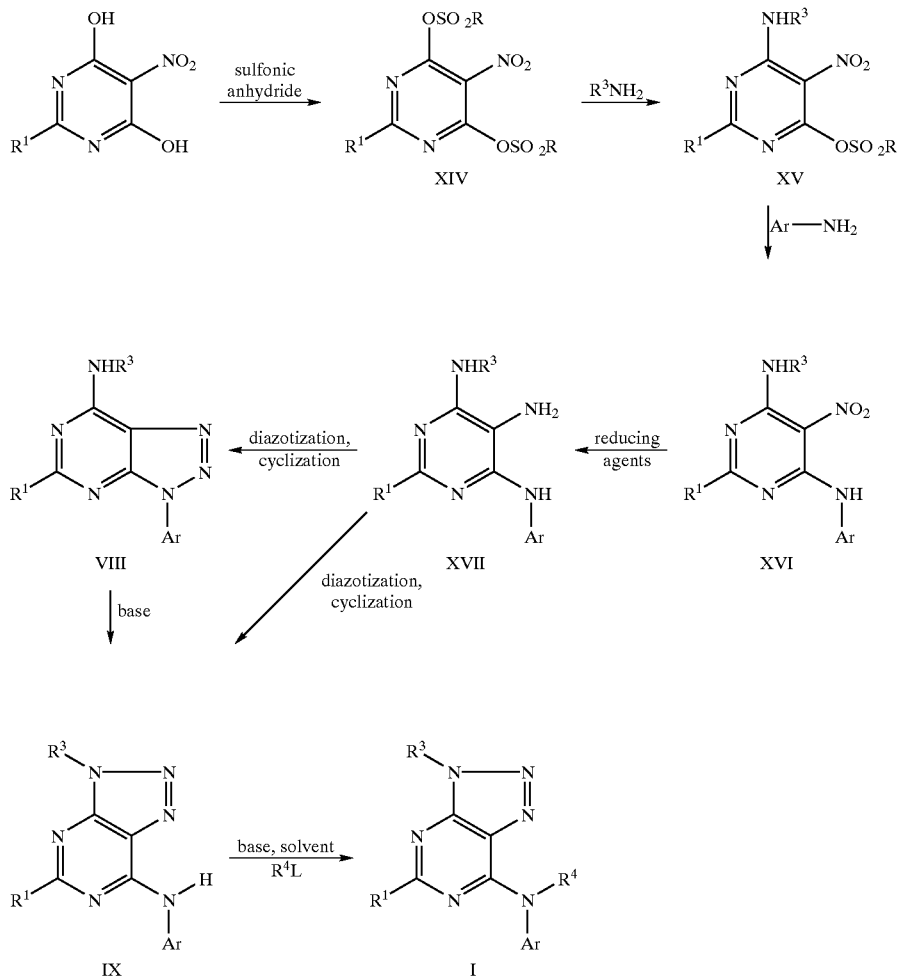

wherein X=Y=N; Z=NR$^3$ 4,6-dihydroxy-5-nitropyrimidines can be treated with aryl sulfonic anhydrides, aryl sulfonyl chlorides, alkyl sulfonic anhydrides or alkyl sulfonyl chlorides in the presence or absence of bases such as alkali metal hydrides, alkaline earth metal hydrides, alkali metal dialkyl amides in inert solvents such as dialkylformamides, dialkylacetamides at temperatures ranging from 0° to 200° C. to give intermediates of Formula (XIV). Compounds of Formula (XIV) are treated with primary amines to give aminonitropyrimidines (XV). Treatment of (XV) with Ar—NH$_2$ can provide compounds of Formula (XVI). Compounds of the formula (XVI) can be reduced to amino derivatives (XVII) using the reagents described for the conversion of (IV) to (V) in Scheme 1. Intermediate (XVII) can be converted to a mixture of (VIII) and (IX) by diazotization and cyclization. Compounds of the Formula (VIII) can be converted to (IX) by treatment with

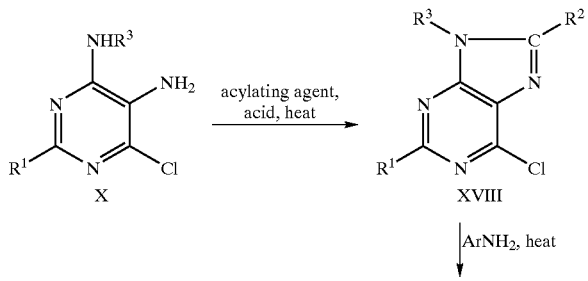

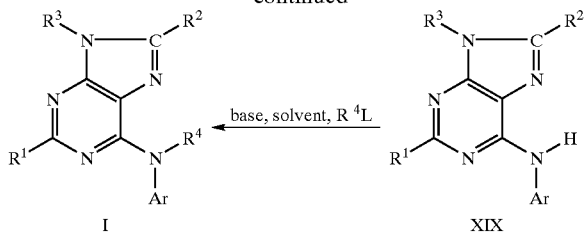

wherein X=N, Y=CR², Z=NR³

Treatment of (X) with an acylating agent such as, but not limited to, alkyl anhydrides, haloalkyl anhydrides, alkylamides, haloalkyl amides, trialkylorthoesters R²(OR)₃ (where R is C₁–C₄ alkyl), guanidines, cyanogen bromide, R²COOH, urea or thiourea in the presence or absence of an acid (such as HOAc, HCl, H₂SO₄) in the presence or absence of an organic cosolvent such as alkyl alcohols, cyclic ethers, or aromatic solvents at temperatures ranging from 0° to 200° C. Treatment of (XVIII) with Ar—NH₂ can provide compounds of Formula (XIX). Finally, alkylation of compound (XIX) can provide imidazolopyrimidine (I, wherein X=N, Y=CR², Z=NR³).

The 1,2,3-thiadiazolo[5,4-d]pyrimidines of the formula (I) (wherein X=Y=N and Z=S), can be prepared as shown in Scheme 6.

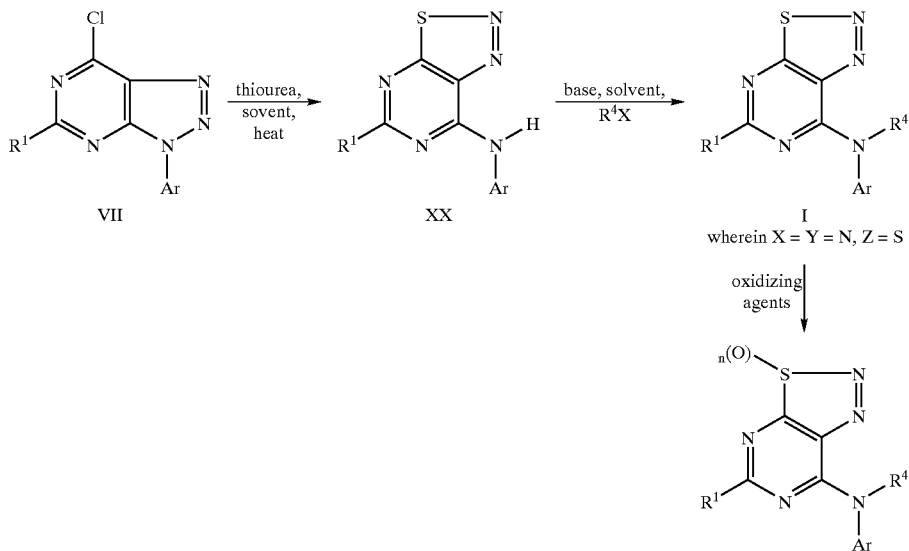

Compounds of the formula (VII) with thiourea can react upon heating in presence of solvents such as but not limited to, cyclic ethers such as tetrahydrofuran, dialkylformamides such as dimethylformamide, dialkyl acetamides, ethylene glycol, 2-ethoxyethanol, halocarbons such as methylene chloride, alkanenitriles such as acetonitrile, or alkyl alcohols such as methanol, ethanol to give compound (XX) which is alkylated to afford thiadiazolpyrimidine (I) (wherein X=Y=N and Z=S). Compounds of Formula (I) can be converted to sulfoxides as well sulfones under a variety of oxidizing agents such as but not limited to, NaIO₄, KMnO₄ or m-chloroperbenzoic acid.

The method of synthesis of the triazolopyridines of this invention is shown in Scheme 7.

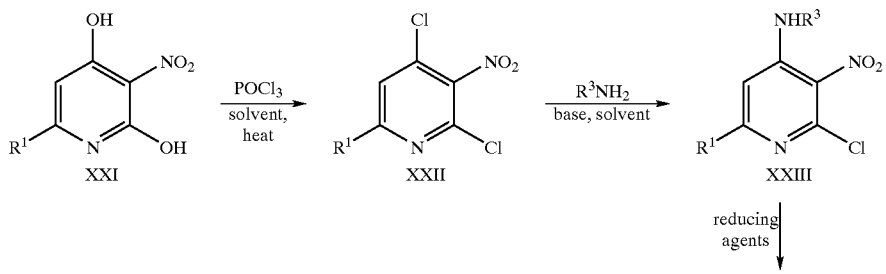

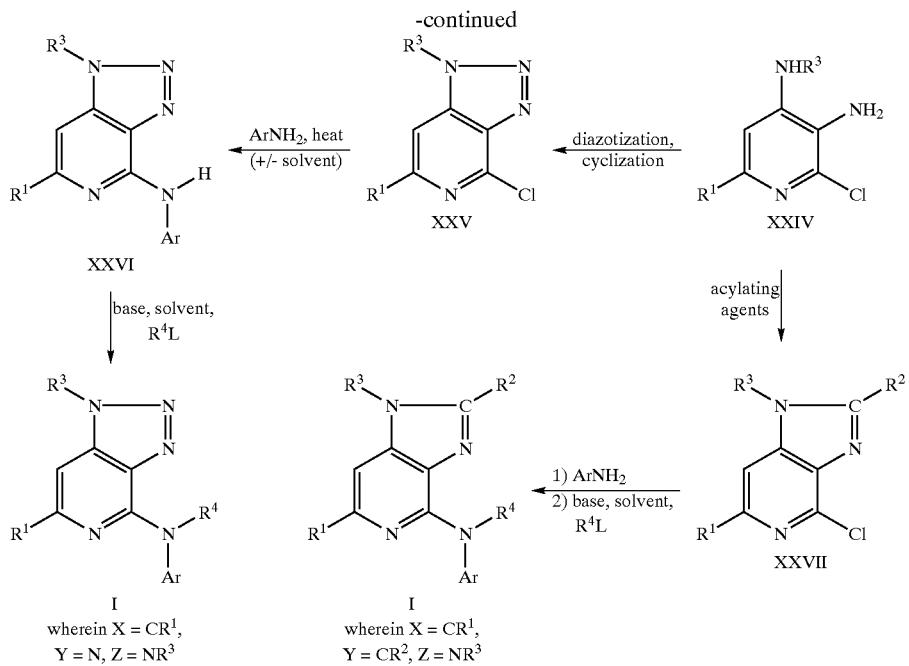

The hydroxy groups in (XXI) can be converted into chloro groups by the action of phosphorous oxychloride with the optional assistance of a catalyst such as dialkylaniline (see: Brown, D. J. et.al. *J. Chem. Soc.,* 1954, 3832) to afford compounds of Formula (XXII). Addition of primary amines to compound (XXII) can provide alkylaminonitropyridines (XXIII). The nitro group in (XXIII) can be reduced using the conditions employed for the transformation of (IV) to (V) to give (XXIV). Diazotization and cyclization of (XXIV) can provide chlorotriazolopyridine derivatives (XXV) as was described for the conversion of (VI) to (VII) in Scheme 1. The chloro group can then be displaced by addition of Ar—$NH_2$ to afford compounds (XXVI) and then treated with $R^4L$ to give (I).

Imidazolopyridines of the present invention can be prepared from compound (XXIV) as shown in Scheme 7 by following the conditions outlined for the conversion of (X) to (XVIII) in Scheme 5. Treatment of compound (XXVII) with Ar—$NH_2$ using the conditions outlined in Scheme 1 can provide compounds of Formula (I, where $R^4$=H). Alkylation with $R^4L$ can afford imidazolopyridines of formula I (where $R^4$ is not equal to H).

Alternatively, the triazolopyridines can be synthesized as shown in Scheme 8.

Scheme 8

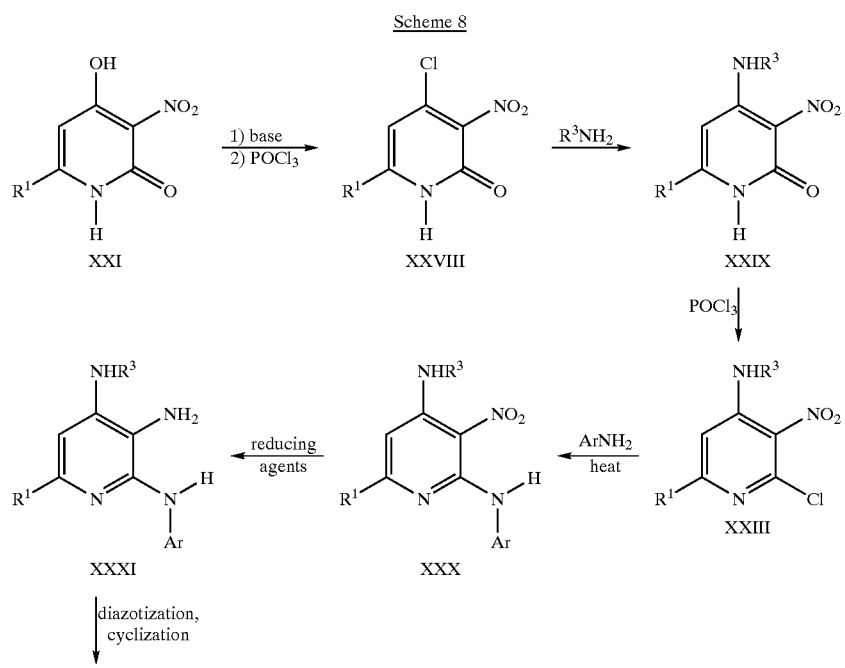

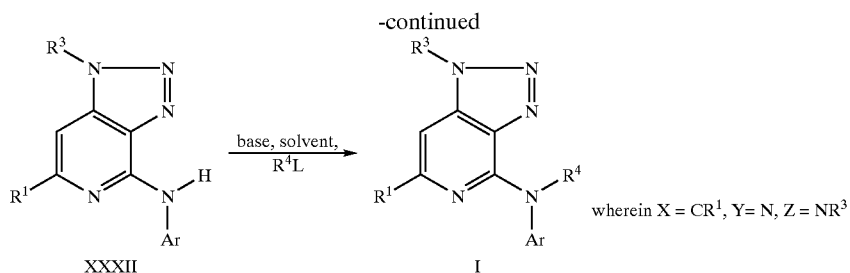

Treatment of compounds of Formula (XXI) with an aliphatic or aromatic amine in the appropriate organic solvent but not limited to, alkyl alcohols such as methanol, ethanol, propanol, butanol, alkyl alkanoates such as ethyl acetate, alkanenitriles such as acetonitrile, dialkyl formamides such as DMF gives the corresponding ammonium salt, which upon treatment with $POCl_3$ at temperatures from 25 to 120° C., give compounds of Formula (XXVIII). Treatment of compounds of Formula (XXVIII) with appropriate primary amines in an organic solvent such as but not limited to, alkyl alcohols such as methanol, ethanol, propanol, butanol, alkyl alkanoates such as ethyl acetate, alkanenitriles such as acetonitrile, dialkyl formamides such as DMF, dialkylsulfoxides at temperatures from 25 to 120° C. to give (XXIX). This was converted to (XXIII) by treatment with $POCl_3$ at temperatures from 25 to 120° C. Compounds of Formula (XXIII) could be coupled with $Ar-NH_2$ with or without the presence of solvent at temperatures from 25 to 200° C. to give product (XXX). These could be converted to intermediates (XXXI) by reduction of the nitro group under a variety of reducing conditions, such as those used for the conversion of (IV) to (V) in Scheme 1. The final cyclizaton was carried out as described for the conversion of (VI) to (VII) in Scheme 1.

Compounds of general formula (II) may be prepared according to the procedures outlined in Scheme 9.

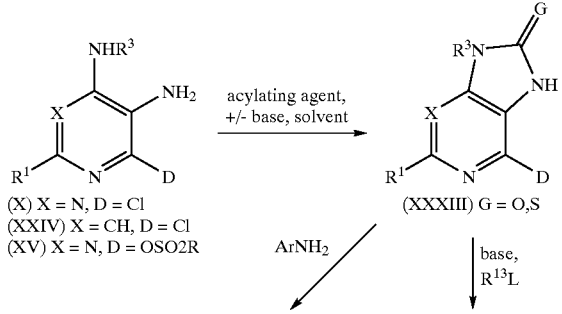

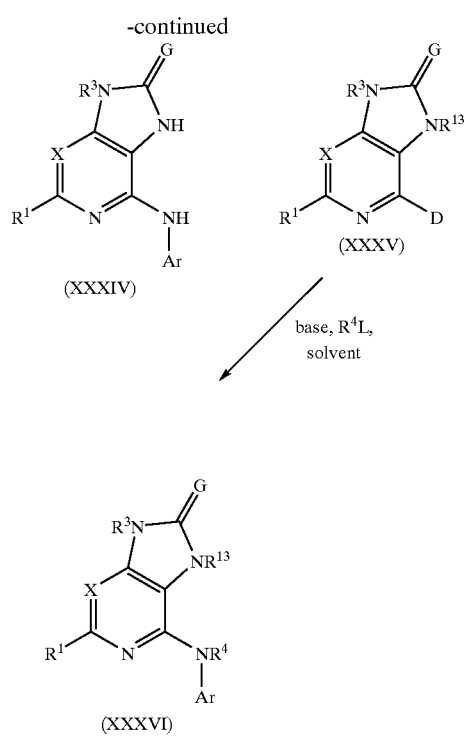

Intermediates of formula (X), (XV) or (XXIV) may be converted to compounds of formula (XXXIII) by treatment with an acylating agent in the presence or absence of a base in an inert solvent at reaction temperatures ranging from −78° C. to 200° C. Acylating agents include, but are not limited to, phosgene, thiophosgene, diphosgene, triphosgene, carbonyl diimidazole, thiocarbonyl diimidazole, dialkylcarbonates (such as diethyl carbonate) or $R^aR^bN(C=G)OR^c$ (where G=O, S; $R^a$, $R^b$, and $R^c$ are independently C1–C8 alkyl). Bases include, but are not limited to, alkali metal alkoxides, akali metal hydrides, trialkyl amines, pyridine, 4-dimethylaminopyridine, alkali metal dialkyl amides or alkali metal bis(trimethylsilyl) amides. Inert solvents include, but are not limited to, halocarbons, alkanenitriles, dialkylformamides, dialkylacetamides, dialkyl ethers, cyclic ethers such as tetrahydrofuran or dioxane, or alkyl alcohols. Intermediates of (XXXIII) may be converted to compounds of formula (XXXIV) (Formula (II) where $R^4$=H) by reaction with $ArNH_2$, using the conditions described for the conversion of compound (V) to (VI) in Scheme 1.

Compounds of Formula (XXXV) may be prepared from compounds of structure (XXXIII) by reaction with $R^{13}L$ (where L is a leaving group such as halide, alkanesulfonate or arylsulfonate) in the presence or absence of a base in an inert solvent. Bases and inert solvents may be the same as those listed above for the preparation of (XXXIII). Intermediates of Formula (XXXV) can be reacted with $ArNH_2$ to give compounds of formula (XXXVI) (Formula (II), where $R^4$=H) using the conditions described for the conversion of compound (V) to (VI) in Scheme 1. Compounds of Formula (XXXVI) may be converted to compounds of (XXXVII) (Formula (II), where $R^4$ does not equal H) by treatment with $R^4L$ (where L is a leaving group such as halide, alkanesulfonate or arylsulfonate) in the presence or absence of a base in an inert solvent. Bases and inert solvents may be the same as those listed above for the preparation of (XXXIII).

As illustrated in Scheme 10, treatment of compounds of Formula (XXI) with an aliphatic or aromatic amine in an appropriate organic solvent (such as but not limited to, alkyl alcohols such as methanol, ethanol, propanol, butanol, alkyl alkanoates such as ethyl acetate, alkanenitriles such as acetonitrile, dialkyl formamides such as DMF, dialkylsulfoxides) at temperatures from 25 to 120° C. provides compounds of Formula (XXIX). These can be converted to (XXIII) by treatment with $POCl_3$ at temperatures from 25 to 120° C. Compounds of Formula (XXIII) can be converted to intermediates (XXIV) by reduction of the nitro group under a variety of reducing conditions, such as those used for the conversion of (IV) to (V) in Scheme 1. Diazotization and cyclization of (XXIV) can provide chlorotriazolopyridine (XXV) as was described for the conversion of of (VI) to (VII) in Scheme I. The chloro group can then be displaced by addition of $Ar-NH_2$ in the presence of an acid such as but not limited to HCl, $H_2SO_4$, AcOH, methanesulfonic acid, p-toluenesulfonic acid in inert solvents such as toluene, xylenes at temperatures ranging from 0° to 200° C. to afford product I. Salts of I are prepared by combining the free base with appropriate acid in a suitable organic solvent.

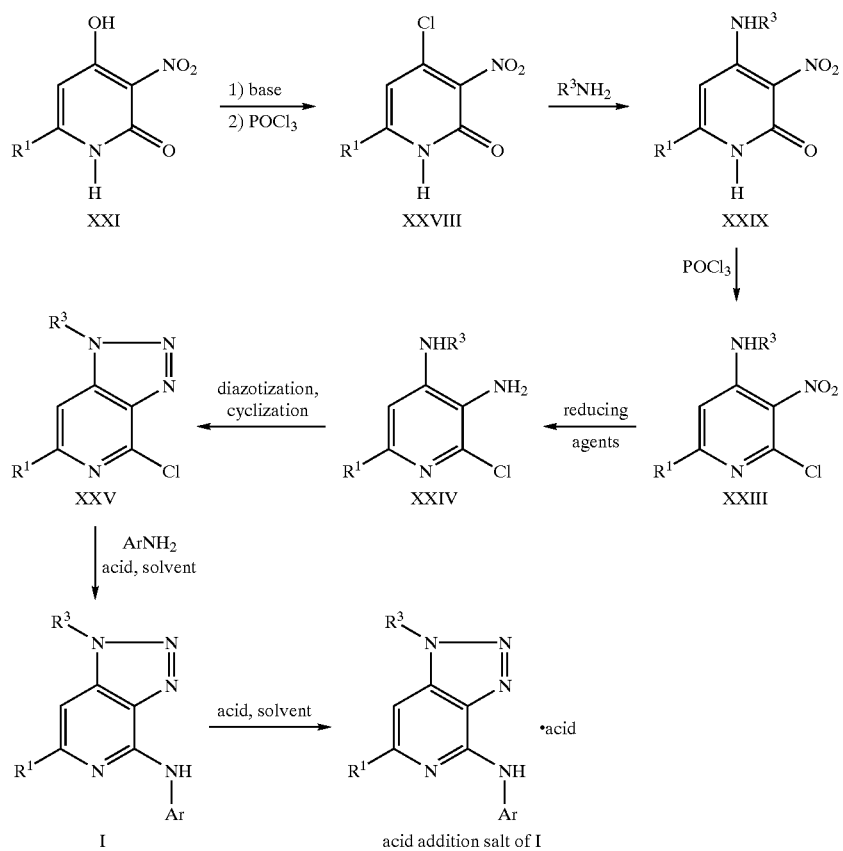

Scheme 10 alkanoates such as ethyl acetate, alkanenitriles such as acetonitrile, dialkyl formamides such as DMF) gives the corresponding ammonium salt, which upon treatment with $POCl_3$ at temperatures from 25 to 120° C., give compounds of Formula (XXVIII). Treatment of compounds of Formula (XXVIII) with appropriate primary amines $R^3NH_2$ in an organic solvent (such as but not limited to, alkyl alcohols such as methanol, ethanol, propanol, butanol, alkyl alkanoates such as ethyl acetate, alkanenitriles such as wherein $X=CR^1$, $Y=N$, $Z=NR^3$ As shown in Scheme 11, reaction of a 4-amino-3-nitropyridone of formula (XXIX) with a reducing agent, such as $Na_2S_2O_4$ affords the corresponding 4-amino-3-aminopyridone of formula (XXXVII). This transformation can be effected under a variety of reducing conditions, such as catalytic hydrogenation, reducing metal reaction (Fe, Sn, Zn), hydride reaction ($NaBH_4$, $LiAlH_4$) etc., which are known to those skilled in the art. The 4-amino-3-aminopyridone can be converted to the triazolopyridone of formula (XXXVIII) by treatment with an alkali metal nitrite, such as $NaNO_2$, under acidic conditions. The resulting triazolopyridone can be converted to the corresponding halo-triazolopyridine of formula (XXXIX)(X=Cl, Br), by treatment with a halogenating agent such as $POCl_3$, $PBr_3$, $POBr_3$. Alternatively X can be an appropriate leaving group resulting from treatment of the triazolopyridone with triflic, tosic or mesyl anhydride in the presence of a base. The triazolopyridine can be coupled with arylamines $ArNH_2$ under acidic, basic or thermal catalysis to compounds of Formula I.

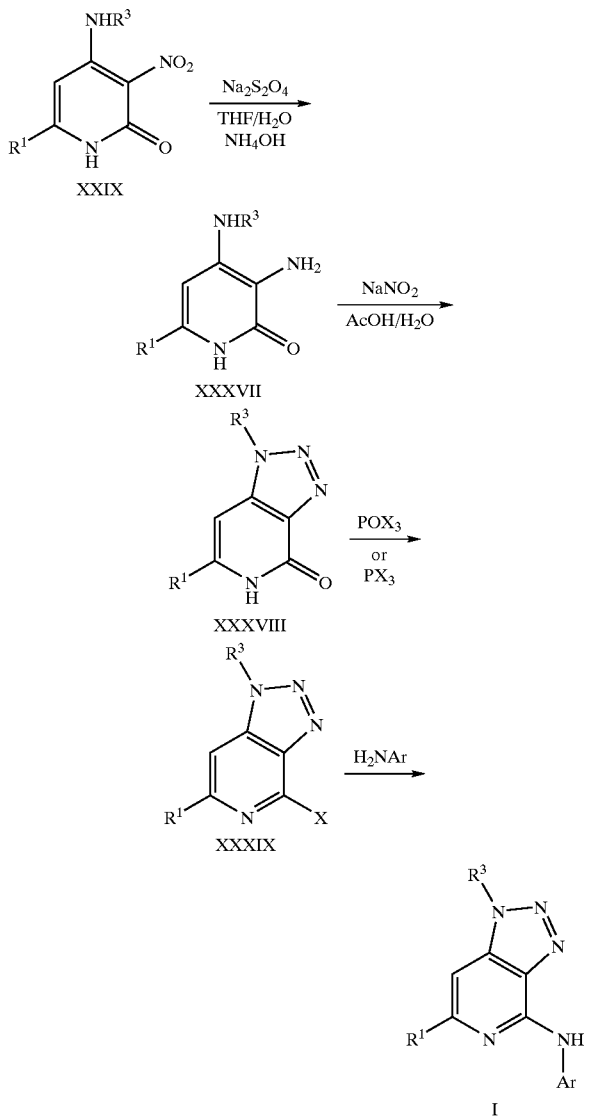

Scheme 11

EXAMPLE 1

N-[2-bromo-4-(1-methylethyl)phenyl]-5-methyl-3-propyl-3H-1,2,3-triazolo[4,5-d]pyrimidin-7-amine Part A 4,6-Dihydroxy-2-methylpyrimidine (60 g) was added in portions to fuming nitric acid (120 mL) at 0° C. while cooling the reaction flask. After completion of addtion, the reaction was stirred an additional 1 h at 0° C. followed by another 1 h at room temperature. The reaction mixture was then poured over ice (200 g) and the ice was allowed to melt. A light pink solid was isolated by filteration and washed with cold water (100 mL). The solid was dried in a vacuum oven overnight to yield 4,6-dihydroxy-2-methyl-5-nitropyrimidine (72.5 g).

Part B

The product of Part A was added portionwise to phosphorous oxychloride (400 mL) under a nitrogen atmosphere followed by dropwise addition of N,N-diethylaniline (80 mL). The reaction mixture was refluxed for 2½ h with stirring, cooled to room temperature, poured over ice (2.0 Kg) and stirred for 1 hr. The aqueous layer was extracted with diethyl ether (4×500 mL) and the extracts combined. The combined extracts were washed with brine (500 mL), dried over anhydrous magnesium sulfate, filtered and stripped down to afford 4,6-dichloro-2-methyl-5-nitropyrimidine as a yellow solid (68.8 g) which has an unpleasant odor.

Part C

The product of Part B (42 g) was added to acetic acid (77 mL) and methanol (350 mL). To this mixture was added iron powder (42 g) in portions, stirred for 2 h at 60–65° C., cooled to room temperature, and filtered. The filterate was stripped to a brown solid, which was extracted with ethyl acetate (2×500 mL), washed with 1N NaOH (250 mL), and brine (500 mL). The organic layer was dried over anhydrous magnesium sulfate, filtered and stripped down to yield 5-amino-4,6-dichloro-2-methylpyrimidine as a pale yellow solid (25.4 g).

Part D

The product of Part C (14.2 g) and 2-bromo-4-isopropylaniline (17.1 g) were dissolved in 2-ethoxyethanol (60 mL) and refluxed at 135° C. for 30 h. The reaction mixture was cooled, removed the solvent, extracted the residue with dichloromethane, washed with water, dried over anhydrous magnesium sulfate. Filtered the extract, removed the solvent and residue was purified by flash column chromatography on a silica gel using methanol+ $CH_2Cl_2$ (1:100) to yield 5-amino-4-(2-bromo-4-isopropylphenyl)-amino-6-chloro-2-methylpyrimidine as a cream colored solid (16.05 g).

Part E

The product of Part D (12.5 g) was dissolved in dichloromethane (125 mL) and 50% aqueous acetic acid (125 mL). To this stirred mixture was added sodium nitrite (2.55 g) in water (10 mL) dropwise at room temperature. After completion of addition, the reaction was stirred for an additional 15 mins. The organic layer was separated, washed with water, dried with anhydrous magnesium sulfate, and stripped down to a residue. The residue was purified by flash column chromatography ($CH_2Cl_2$) to afford light brown oil. The oil was crystallized from 1:1 hexane+pentane (15 mL) to yield 3-[2-bromo-4-(1-methylethyl)phenyl]-7-chloro-5-methyl-3H-1,2,3-triazolo[4,5-d]pyrimidine as an off-white solid (12.15 g).

Part F

The product of Part E (0.65 g) was dissolved in dichloromethane (20 mL) and then added 1.0 g of 1-propylamine at room temperature. The reaction mixture was stirred at room temperature for 1 h, washed with water, dried with anhydrous magnesium sulfate, and stripped down to a white solid. The crude solid was recrystallized from 2-propanol (2 mL) to furnish 3-[2-bromo-4-(1-methylethyl)phenyl]-5-methyl-N-propyl-3H-1,2,3-triazolo[4,5-d]pyrimidin-7-amine as a white needles (0.58 g; mp 156–157° C.). Elemental analysis for $C_{17}H_{21}BrN_6$: Theory C, 52.45; H, 5.45; N, 21.59; Found: C, 52.47; H, 5.33; N, 21.46.

Part G
Rearrangement of Product F

The product of Part F (0.40 g) was dissolved in dry DMF (10 mL) and added NaH (0.103 g, 60% in oil) at room temperature under a nitrogen atmosphere. The mixture was stirred at room temperature for 14 h and partitioned between ethyl acetate (25 mL) and water (25 mL). The organic layer was washed with brine, dried, and stripped in vacuum to a solid. The solid was recrystallized from 2-propanol (0.5 mL) to afford the title compound as a white crystalline solid (0.35 g; mp 80–81° C.). Elemental analysis for $C_{17}H_{21}BrN_6$: Theory C, 52.45; H, 5.45; N, 21.59. Found: C, 52.19; H, 5.37; N, 21.48.

EXAMPLE 2

N-[2-bromo-4-(1-methylethyl)phenyl]-N-ethyl-5-methyl-3-propyl-3H-1,2,3-triazolo[4,5-d]pyrimidin-7-amine The title compound from Example 1 (0.30 g) was dissolved in dry DMF (10 mL) and added NaH (62 mg; 60% in oil) at room temperature under a nitrogen atmosphere. The reaction mixture was stirred for 5 mins., and then added EtI (0.2 mL) and continued for an additional 24 h. The reaction mixture was partitioned between ethyl acetate (25 mL) and water (25 mL), washed the organic layer with brine, dried, and stripped in vacuum to yield a.pale yellow oil. The sample was purified by flash column chromatography (1:100 MeOH+CH$_2$Cl$_2$) to afford the title compound as a colorlesss oil (0.16 g). Elemental analysis for $C_{19}H_{25}BrN_6$: Theory C, 54.68; H, 6.05 Found: C, 54.66; H, 6.02.

EXAMPLE 3

N-[2-bromo-4-(1-methylethyl)phenyl]-3-butyl-N-ethyl-5-methyl-3H-1,2,3-triazolo[4,5-d]pyrimidin-7-amine Part A The product of Part E from Example 1 was treated with 1-butylamine in the same manner as outlined in Part F to afford 3-[2-bromo-4-(1-methylethyl)phenyl]-N-butyl-5-methyl-3H-1,2,3-triazolo[4,5-d]pyrimidin-7-amine as a white solid (mp 149–151° C.). Elemental analysis for $C_{18}H_{23}BrN_6$: Theory C, 53.60; H, 5.76; N, 20.84. Found: C, 53.46; H, 5.62; N, 20.80.

Part B

The product of Part A from Example 3 (0.34 g) was dissolved in dry DMF (10 mL) and added NaH (67 mg; 60% in oil) at room temperature under a nitrogen atmosphere. The reaction mixture was stirred for 24 h, then added EtI (0.1 mL) and continued for another 24 hrs. The title compound was isolated in the same way as described in Example 2 to afford colorless oil (0.21 g). Elemental analysis for $C_2OH_{27}BrN_6$: Theory C, 55.69; H, 6.32; N, 19.48. Found: C, 55.61; H, 6.19; N, 19.23.

EXAMPLE 4

N-[2-bromo-4-(1-methylethyl)phenyl]-3-(cyclopropylmethyl)-N-ethyl-5-methyl-3H-1,2,3-triazolo[4,5-d]pyrimidin-7-amine Part A The product of Part E from Example 1 was reacted with aminomethylcyclopropane in the same way as outlined in Part F to furnish 3-[2-bromo-4-(1-methylethyl)phenyl]-N-(cyclopropyl-methyl)-5-methyl-3H-1,2,3-triazolo[4,5-d]pyrimidin-7-amine as a white needles (mp 166–167° C.). Elemental analysis for $C_{18}H_{21}BrN_6$: Theory C, 53.87; H, 5.27; N, 20.94. Found: C, 54.11; H, 5.32; N, 21.08.

Part B

Using the procedure for Part G in Example 1, the product of Part A in Example 4 was rearranged to yield the title compound as a white crystalline solid (mp 100–101° C.). Elemental analysis for $C_{18}H_{21}BrN_6$: Theory C, 53.87; H, 5.27; N, 20.94. Found: C, 53.93; H, 5.28; N, 20.78.

Part C

Using the procedure for Example 2, the product of Part B from above was alkylated to furnish the title compound as a colorless oil. Elemental analysis for $C_{20}H_{25}BrN_6$: Theory C, 55.95; H, 5.88; N, 19.57. Found: C, 56.11; H, 6.04; N, 19.23.

EXAMPLE 5

N-[2-bromo-4-(1-methyl)ethylphenyl]-5-methyl-3-[(1-methoxymethyl)-2-methoxyethyl)-3H-1,2,3-triazolo[4,5-d]pyrimidin-7-amine Part A Serinol (3.42 g) was added to a solution of trityl chloride (8.36 g) and triethylamine in 75 mL of dry DMF. After stirring at room temperature overnight, the reaction was poured into water and extracted twice with toluene. The combined organic layers were dried over potassium carbonate and concentrated to dryness. Recrystallization from boiling 1:1 benzene/hexane (two crops) afforded N-triphenylmethylserinol (7.59 g).

Part B

Methyl iodide (2.60 mL) was added to a suspension of N-triphenylmethylserinol (6.34 g) and powdered sodium hydroxide (7.60 g) in 95 mL of dry DMSO. After stirring overnight, more methyl iodide was added (0.35 mL). After stirring for an additional 24 h, the reaction was added to water and extracted with toluene, toluene/ether, and then ether. The combined organic layers were dried over potassium carbonate and concentrated to afford 1,3-dimethoxy-2-triphenylmethylaminopropane (7.00 g) as a thick viscous oil.

Part C

To a solution of the product of Part B (1.45 g) in methanol (32 mL) was added 1 M HCl in ether (8.4 mL). After stirring overnight, the reaction was added to hexane and extracted with 1:1 methanol/water. The methanol/water layer was washed twice with hexane and concentrated to dryness to afford 1,3-dimethoxy-2-aminopropane hydrochloride (600 mg) as a waxy solid.

Part D

The product of Part C (576 mg), 3-[2-bromo-4-(1-methyl)ethylphenyl]-7-chloro-5-methyl-3H-1,2,3-triazolo[4,5-d]pyrimidine (0.733 g, from Example 1, Part E) and triethylamine (0.56 mL) were stirred overnight at room temperature. The reaction mixture was added to aqueous sodium dihydrogen phosphate and extracted three times with dichloromethane. The combined organic layers were dried over magnesium sulfate and concentrated. Recrystallization from ether/hexane and then boiling methanol afforded N-(1-methoxymethyl-2-methoxyethyl)-3-[2-bromo-4-(1-methyl) ethylphenyl]-5-methyl-3H-1,2,3-triazolo[4,5-d]pyrimidin-7-amine (855 mg) as crystals melting 156.0–158.5°. Calculated for C19H25N602Br: C, 50.79%; H, 5.62%; N, 18.70%. Found: C, 50.48%; H, 5.65%; N, 18.41%.

Part E

The product of Part D (449 mg), dry t-butanol (8 mL) and 1 M potassium t-butoxide (2 mL) were heated at reflux for 2 h. The reaction mixture was added to saturated aqueous ammonium chloride and extracted with dichloromethane. The combined organic layers were dried over magnesium sulfate and concentrated to dryness. The residue crystallized after partial evaporation of a dichloromethane/ether/hexane solution, affording the title compound (403 mg) as an amorphorus white solid melting 53.5–60.0°. Calculated for C19H25N6O2Br: C, 50.79%; H, 5.62%; N, 18.70%. Found: C, 50.92%; H, 5.62%; N, 18.77%.

EXAMPLE 6

N-[2-bromo-4-(1-methylethyl)phenyl]-3-(2-methoxyethyl)-5-methyl-3H-1,2,3-triazolo[4,5-d]pyrimidin-7-amine Part A The product of Part E from Example 1 was reacted with 2-methoxyethylamine in the same way as outlined in Part F to furnish 3-[2-bromo-4-(1-methylethyl)phenyl]-N-(2-methoxyethyl)-5-methyl-3H-1,2,3-triazolo[4,5-d]pyrimidin-7-amine as a white solid (mp 134–136° C.). Elemental analysis for $C_{17}H_{21}BrN_6O$: Theory C, 50.38; H, 5.22; N, 20.74. Found: C, 50.37; H, 5.32; N, 20.52.

Part B

Using the procedure for Part G in Example 1, the product of Part A in Example 6 was rearranged to yield the title compound as a white crystalline solid (mp 94–95° C.). Elemental analysis for $C_{17}H_{21}BrN_6O$: Theory C, 50.38; H, 5.22; N, 20.74. Found: C, 50.40; H, 5.31; N, 20.65.

EXAMPLE 7

N-[2-bromo-4-(1-methylethyl)phenyl]-N-ethyl-3-(2-methoxyethyl)-5-methyl-3H-1,2,3-triazolo[4,5-d]pyrimidin-7-amine Using the procedure for Example 2, the product of Part B in Example 6 was alkylated to furnish the title compound as a colorless oil. Elemental analysis for $C_{19}H_{25}BrN_6O$: Theory C, 52.66; H, 5.81; N, 19.39. Found: C, 52.85; H, 5.96; N, 19.02.

EXAMPLE 8

N-[2-bromo-4-(1-methylethyl)phenyl]-N-ethyl-3-(3-methoxypropyl)-5-methyl-3H-1,2,3-triazolo[4,5-d]pyrimidin-7-amine Part A The product of Part E from Example 1 was treated with 3-methoxyethylamine in the same manner as outlined in Part F to afford 3-[2-bromo-4-(1-methylethyl)phenyl]-N-ethyl-N-(3-methoxypropyl)-5-methyl-3H-1,2,3-triazolo[4,5-d]pyrimidin-7-amine as a white solid (mp 109–110° C.). Elemental analysis for $C_{18}H_{23}BrN_6O$: Theory C, 51.56; H, 5.54; N, 20.04. Found: C, 51.57; H, 5.40; N, 20.23.

Part B

The product of Part A from Example 8 was rearranged and alkylated in the same way as outlined in Part B of Example 3 to furnish the title compound as a colorless oil. Elemental analysis for $C_{20}H_{27}BrN_6O$: Theory C, 53.69; H, 6.08; N, 18.79. Found: C, 53.63; H, 5.98; N, 18.59.

EXAMPLE 9

(+/−)-N-[2-bromo-4-(1-methylethyl)phenyl]-3-[1-(1-methoxymethyl)propyl]-5-methyl-3H-1,2,3-triazolo[4,5-d]pyrimidin-7-amine Part A The product of Part E (0.72 g) from Example 1 was dissolved in a mixture of ethanol (10 mL) and triethylamine (0.21 g) and added 2-amino-1-methoxybutane (0.23 g). The reaction mixture was refluxed for 8 h, removed the solvent, partitioned between ethyl acetate (25 mL) and water (25 mL), washed the organic layer with brine, dried and stripped down to a residue. The residue was purified by flash column chromatography (1:100 MeOH+CH$_2$Cl$_2$) to afford (+/−)-3-[2-bromo-4-(1-methylethyl)phenyl]-N-[1-(1-methoxymethyl)propyl]-5-methyl-3H-1,2,3-triazolo[4,5-d]pyrimidin-7-amine as a white solid (mp 132–134° C.). Elemental analysis for $C_{19}H_{25}BrN_6O$: Theory C, 52.66; H, 5.81; N, 19.39. Found: C, 52.52; H, 5.72; N, 19.46.

Part B

The product of Part A from Example 9 was rearranged in a manner similar to Part G of Example 1 to furnish the title compound as a white crystalline solid (mp 115–116° C.). Elemental analysis for $C_{19}H_{25}BrN_6O$: Theory C, 52.66; H, 5.81; N, 19.39. Found: C, 52.61; H, 5.70; N, 19.41.

EXAMPLE 10

(+/−)-N-[2-bromo-4-(1-methylethyl)phenyl]-N-ethyl-3-[1-(1-methoxymethyl)propyl]-5-methyl-3H-1,2,3-triazolo[4,5-d]pyrimidin-7-amine Using the procedure for Example 2, the product of Part B in Example 9 was alkylated to afford the title compound as a colorless oil. Elemental analysis for $C_{21}H_{29}BrN_6O$: Theory C, 54.66; H, 6.35; N, 18.21. Found: C, 54.76; H, 6.86; N, 17.85.

EXAMPLE 11

(S)-N-[2-bromo-4-(1-methylethyl)phenyl]-3-[1-(1-methoxymethyl)-2-phenylethyl]-5-methyl-3H-1,2,3-triazolo[4,5-d]pyrimidin-7-amine Part A The product of Part E from Example 1 was treated with S-(+)-2-amino-1-methoxy-3-phenylpropane hydrochloride in the same manner as outlined in Part A of Example 9 to afford (S)-3-[2-bromo-4-(1-methylethyl)phenyl]-N-[1-(1-methoxymethyl)-2-phenylethyl]-5-methyl-3H-1,2,3-triazolo[4,5-d]pyrimidin-7-amine as a white solid (mp 67–69° C.). Elemental analysis for $C_{24}H_{27}BrN_6O$: Theory C, 58.18; H, 5.49; N, 16.96. Found: C, 57.79; H, 5.39; N, 16.77.

Part B

The product of Part A from Example 11 was rearranged in the same way as outlined in Part G of Example 1 to furnish the title compound as a colorless oil. Elemental analysis for $C_{24}H_{27}BrN_6O$: Theory C, 58.18; H, 5.49; N, 16.96. Found: C, 57.94; H, 5.49; N, 16.43.

EXAMPLE 12

(S)-methyl 7-[2-bromo-4-(1-methylethyl)phenyl]-5-methyl-a-[2-(methylthio)ethyl]-3H-1,2,3-triazolo[4,5-d]pyrimidine-3-acetate Part A The product of Part E from Example 1 was treated with L-methionine methyl ester hydrochloride in the same manner as outlined in Part A of Example 9 to afford (S)-methyl 3-[2-bromo-4-(1-methylethyl)phenyl]-5-methyl-a-[2-(methylthio)ethyl]-3H-1,2,3-triazolo[4,5-d]pyrimidine-7-acetate as a white solid (mp 135–137 ° C.). Elemental analysis for $C_{20}H_{25}BrN_6O_2S$: Theory C, 48.68; H, 5.12; N, 17.03. Found: C, 48.73; H, 5.21; N, 16.90.

Part B

The product of Part A from Example 12 was rearranged in the same way as described in Part G of Example 1 to furnish the title compound as a colorless oil. Elemental analysis for $C_{20}H_{25}BrN_6O_2S$: Theory C, 48.68; H, 5.12; N, 17.03. Found: C, 48.55; H, 5.19; N, 16.82.

EXAMPLE 13

(+/−)-N-[2-bromo-4-(1-methylethyl)phenyl]-3-[1-ethylpentyl]-5-methyl-3H-1,2,3-triazolo[4,5-d]pyrimidin-7-amine Part A The product of Part E from Example 1 was reacted with 3-aminoheptane in the same way as outlined in Part F to yield 3-[2-bromo-4-(1-methylethyl)phenyl]-N-[1-ethylpentyl]-5-methyl-3H-1,2,3-triazolo[4,5-d]pyrimidin-7-amine as a white crystalline solid (mp 137–138° C.). Elemental analysis for $C_{21}H_{29}BrN_6$: Theory C, 56.63; H, 6.56; N, 18.87. Found: C, 56.53; H, 6.54; N, 18.79.

Part B

Using the procedure for Part G in Example 1, the product of Part A in Example 13 was rearranged to yield the title compound as a colorless oil. Elemental analysis for $C_{21}H_{29}BrN_6$: Theory C, 56.63; H, 6.56; N, 18.87. Found: C, 56.78; H, 6.58; N, 18.79.

EXAMPLE 14

(+/−)-N-[2-bromo-4-(1-methylethyl)phenyl]-N-ethyl-3-[1-ethylpentyl]-5-methyl-3H-1,2,3-triazolo[4,5-d]pyrimidin-7-amine Using the procedure for Example 2, the product of Part B in Example 13 was alkylated to furnish the title compound as a colorless oil. Mass spec. (ESI): 473.4

EXAMPLE 15

N-[2-bromo-4-(1-methylethyl)phenyl]-3-[1-propylbutyl]-5-methyl-3H-1,2,3-triazolo[4,5-d]pyrimidin-7-amine Part A The product of Part E from Example 1 was reacted with 4-aminoheptane in the same manner as outlined in Part A of Example 9 to yield 3-[2-bromo-4-(1-methylethyl)phenyl]-N-[1-propylbutyl]-5-methyl-3H-1,2,3-triazolo[4,5-d]pyrimidin-7-amine as a white crystalline solid (mp 162–163° C.). Elemental analysis for $C_{21}H_{29}BrN_6$: Theory C, 56.63, H: 6.56, N: 18.87. Found: C: 56.64, H: 6.56, N; 18.81.

Part B

Using the procedure for Part G in Example 1, the product of Part A in Example 15 was rearranged to yield the title compound as a white crystalline solid (mp 69–70° C.). Elemental analysis for $C_{21}H_{29}BrN_6$: Theory C, 56.63; H, 6.56; N, 18.87. Found: C, 56.69; H, 6.48; N, 18.97.

EXAMPLE 16

N-[2-bromo-4-(1-methylethyl)phenyl]-3-[1-butylpentyl]-5-methyl-3H-1,2,3-triazolo[4,5-d]pyrimidin-7-amine Part A The product of Part E from Example 1 was reacted with 5-aminononane in a manner similar to Part A of Example 9 to yield 3-[2-bromo-4-(1-methylethyl)phenyl]-N-[1-butylpentyl]-5-methyl-3H-1,2,3-triazolo[4,5-d]pyrimidin-7-amine as a white crystalline solid (mp 132–133° C.). Elemental analysis for $C_{23}H_{33}BrN_6$: Theory C, 58.35; H, 7.04; N, 17.75. Found: C, 58.19; H, 7.00; N, 17.97.

Part B

Using the procedure for Part G in Example 1, the product of Part A in Example 16 was rearranged to yield the title compound as a colorless oil. Elemental analysis for $C_{23}H_{33}BrN_6$: Theory C, 58.35; H, 7.04; N, 17.75. Found: C, 58.58; H, 7.12; N, 17.47.

EXAMPLE 17

(+/−)-N-[2-bromo-4-(1-methylethyl)phenyl]-3-[1-ethylbutyl]-5-methyl-3H-1,2,3-triazolo[4,5-d]pyrimidin-7-amine Part A The product of Part E from Example 1 was reacted with 3-aminohexane in a manner similar to Part A of Example 9 to yield 3-[2-bromo-4-(1-methylethyl)phenyl]-N-[1-ethylbutyl]-5-methyl-3H-1,2,3-triazolo[4,5-d]pyrimidin-7-amine as a white crystalline solid (mp 154–155° C.). Elemental analysis for $C_{20}H_{27}BrN_6$: Theory C, 55.69; H, 6.32; N, 19.48. Found: C, 55.57; H, 6.31; N, 19.41.

Part B

Using the procedure for Part G in Example 1, the product of Part A in Example 17 was rearranged to yield the title compound as a white crystalline solid (87–88° C.). Elemental analysis for $C_{20}H_{27}BrN_6$: Theory C, 55.69; H, 6.32; N, 19.48. Found: C, 55.70; H, 6.36; N, 19.40.

EXAMPLE 18

(+/−)-7-[2-bromo-4-(1-methylethyl)phenyl]-5-methyl-a-propyl-3H-1,2,3-triazolo[4,5-d]pyrimidine-3-ethanol Part A The product of Part E from Example 1 was treated with DL-2-amino-1-pentanol in a manner similar to Part A of Example 9 to furnish 3-[2-bromo-4-(1-methylethyl)phenyl]-5-methyl-a-propyl-3H-1,2,3-triazolo[4,5-d]pyrimidine-7-ethanol as a white crystalline solid (mp 154–155° C.). Elemental analysis for $C_{19}H_{25}BrN_6O$: Theory C, 52.66; H, 5.83; N, 19.39. Found: C, 52.54; H, 5.64; N, 19.12.

Part B

Using the procedure for Part G in Example 1, the product of Part A in Example18 was rearranged to afford the title compound as a colorless oil. Elemental analysis for $C_{19}H_{25}BrN_6O$: Theory C, 52.66; H, 5.83; N, 19.39. Found: C, 52.46; H, 5.83; N, 19.18.

EXAMPLE 19

N-[2-bromo-4-(1-methylethyl)phenyl]-3-[1-ethylpropyl]-5-methyl-3H-1,2,3-triazolo[4,5-d]pyrimidin-7-amine Part A The product of Part E from Example 1 was reacted with 3-aminopentane in the same manner as outlined in Part A of Example 9 to yield 3-[2-bromo-4-(1-methylethyl)phenyl]-N-[1-ethylpropyl]-5-methyl-3H-1,2,3-triazolo[4,5-d]pyrimidin-7-amine as a white crystalline solid (mp 171–172° C.). Elemental analysis for $C_{19}H_{25}BrN_6$: Theory C, 54.68; H, 6.05; N, 20.14. Found: C, 54.54; H, 5.73; N, 20.18.

Part B

Using the procedure for Part G in Example 1, the product of Part A in Example 19 was rearranged to yield the title compound as a white crystalline solid (mp 117–118° C.). Elemental analysis for $C_{21}H_{29}BrN_6$: Theory C, 56.63; H, 6.56; N, 18.87. Found: C, 54.86; H, 5.93; N, 20.17.

EXAMPLE 20

N-[2-bromo-4-(1-methylethyl)phenyl]-N-ethyl-3-[1-ethylpropyl]-5-methyl-3H-1,2,3-triazolo[4,5-d]pyrimidin-7-amine Using the procedure for Example 2, the product of Part B in Example 19 was alkylated to afford the title compound as a colorless oil. Elemental analysis for $C_{21}H_{29}BrN_6$: Theory C, 56.63; H, 6.56; N, 18.87. Found: C, 56.63; H, 6.33; N, 18.78.

EXAMPLE 21

N-(2-bromo-4,6-dimethylphenyl)-5-methyl-3-[1-propylbutyl]-3H-1,2,3-triazolo[4,5-d]pyrimidin-7-amine Part A The product of Part D (9 g) from Example 1 was dissolved in ethanol (100 mL) and N,N-diisopropylethylamine (8 g). To this mixture 4-aminoheptane (7.65 g) was added and refluxed for 7 days. The ethanol was stripped off in vacuum, the residue was partitioned between ethyl acetate (250 mL) and water (150 mL). The ethyl acetate layer was washed with brine (100 mL), dried and stripped in vacuum to a pale yellow solid. Recrystallized from 2-propanol (20 mL) to yield 5-amino-4-chloro-6-(4-heptyl)amino-2-methylpyrimidine as a white crystalline solid (12.5 g; mp162–163° C.). Elemental analysis for $C_{12}H_{21}ClN_4$: Theory C, 56.13; H, 8.24; N, 21.82. Found: C, 55.94; H, 8.22; N, 21.78.

Part B

Using the procedure for Part E in Example 1, the product of Part A in Example 21 was cyclized to yield 7-chloro-5-methyl-3-[1-propylbutyl]-3H-1,2,3-triazolo[4,5-d]pyrimidine as a pale yellow solid (mp 92–93° C.). Elemental analysis for $C_{12}H_{18}ClN_5$: Theory C, 53.83; H, 6.79; N, 26.16. Found: C, 53.81; H, 6.60; N, 25.98.

Part C

The product of Part B (0.27 g) from above was combined with 4-bromo-2,6-dimethylaniline (0.2 g) and heated at 150° C. for 4 h. The reaction mixture was partitioned between dichloromethane (20 mL) and water (20 mL), washed the organic layer with water, dried and stripped in vacuum to a residue. The residue was purified by flash column chromatography (1:100 MeOH+$CH_2Cl_2$) to afford the title compound as an off-white solid (0.26 g; mp 141–142° C.). Elemental analysis for $C_{20}H_{27}BrN_6$: Theory C, 55.69; H, 6.32; N, 19.48. Found: C, 56.05; H, 6.26; N, 19.71.

EXAMPLE 22

5-methyl-N-[4-(1-methylethyl)-2-(methylthio)phenyl]-3-[1-propylbutyl]-3H-1,2,3-triazolo[4,5-d]pyrimidin-7-amine The product of Part B from Example 21 was treated with 4-isopropyl-2-methylthioaniline in a manner similar to Part C in Example 21, to yield the title compound as a pale yellow oil. Elemental analysis for $C_{22}H_{32}N_6S$: Theory C, 64.04; H, 7.83; N, 20.37. Found: C, 64.12; H, 7.54; N, 20.41.

EXAMPLE 23

N-[2-bromo-4-(trifluromethyl)phenyl)]-5-methyl-3-[1-propylbutyl]-3H-1,2,3-triazolo[4,5-d]pyrimidin-7-amine The product of Part B from Example 21 was combined with 2-bromo-4-trifluromethylaniline in a manner similar to Part C in Example 21, to yield the title compound as a white crystalline solid (mp 84–85° C.). Elemental analysis for $C_{19}H_{22}BrF_3N_6$: Theory C, 48.42; H, 4.70; N, 17.83. Found: C, 48.58; H, 4.50; N, 17.78.

EXAMPLE 24

N-[2-bromo-4,6-(dimethoxy)phenyl)]-5-methyl-3-[1-propylbutyl]-3H-1,2,3-triazolo[4,5-d]pyrimidin-7-amine The product of Part B from Example 21 was combined with 2-bromo-4,6-dimethoxyaniline in a manner similar to Part C in Example 21, to yield the title compound as a white crystalline solid (mp 146–147° C.). Elemental analysis for $C_{20}H_{27}BrN_6O_2$: Theory C, 51.84; H, 5.87; N, 18.14. Found: C, 51.95; H, 5.68; N, 18.15.

EXAMPLE 25

N-[2,6-dimethyl-4-(methylthio)phenyl)]-5-methyl-3-[1-propylbutyl]-3H-1,2,3-triazolo[4,5-d]pyrimidin-7-amine The product of Part B from Example 21 was combined with 2,6-dimethyl-4-methylthioaniline in a manner similar to Part C in Example 21, to yield the title compound as a cream colored solid (mp 139–140° C.). Elemental analysis for $C_{21}H_{30}N_6S$: Theory C, 63.28; H, 7.60; N, 21.09. Found: C, 62.98; H, 7.32; N, 21.38.

EXAMPLE 26

N-(4-acetyl-2-bromophenyl)-3-[1-ethylpropyl]-5-methyl-3H-1,2,3-triazolo[4,5-d]pyrimidin-7-amine Part A The product of Part D from Example 1 was treated with 3-aminopentane in a manner similar to Part A of Example 21, to yield 5-amino-4-chloro-2-methyl-6-(3-pentyl)aminopyrimidine as a white crystalline solid (mp 155–156° C.). Elemental analysis for $C_{10}H_{17}ClN_4$: Theory C, 52.51; H, 7.49; N, 24.50. Found: C, 52.43; H, 7.31; N, 24.59.

Part B

The product of Part A from above was cyclized in a manner similar to Part E of Example 1 to yield 7-chloro-5-methyl-3H-1,2,3-triazolo[4,5-d]pyrimidine as a white crystalline solid (mp 96–97 ° C.). Elemental analysis for $C_{10}H_{14}ClN_5$: Theory C, 50.11; H, 5.90; N, 29.22. Found: C, 50.40; H, 5.78; N, 29.53.

Part C

The product of Part B from above was combined with 4-acetyl-2-bromoaniline in a manner similar to Part C in Example 21, to yield the title compound as a pale yellow solid (mp 153–154° C.). Elemental analysis for $C_{18}H_{21}BrN_6O$: Theory C, 51.81; H, 5.07; N, 20.14. Found: C, 51.86; H, 5.87; N, 19.84.

EXAMPLE 27

(+/−)-N-(4-acetyl-2-bromophenyl)-3-[1-(1-methoxymethyl)propyl]-5-methyl-3H-1,2,3-triazolo[4,5-d]pyrimidin-7-amine Part A The product of Part D from Example 1 was treated with 2-amino-1-methoxybutane in a manner similar to Part A of Example 21, to yield 5-amino- 4-chloro-6-(1-methoxy-2-butyl)amino-2-methylpyrimidine as an orange yellow solid (mp 128–130° C.).

Part B

The product of Part A from above was cyclized in a manner similar to Part E of Example 1 to yield 7-chloro-3-[1-(1-methoxymethyl)propyl]-5-methyl-3H-1,2,3-triazolo[4,5-d]pyrimidine as an off-white crystalline solid (mp 66–87° C.). Elemental analysis for $C_{10}H_{14}ClN_5O$: Theory C, 46.97; H, 5.53; N, 27.39. Found: C, 47.22; H, 5.43; N, 27.47.

Part C

The product of Part B from above was combined with 4-acetyl-2-bromoaniline in a manner similar to Part C in Example 21, to yield the title compound as a pale yellow solid (mp 133–134° C.). Elemental analysis for $C_{18}H_{21}BrN_6O_2$: Theory C, 49.89; H, 4.90. Found: C, 50.13; H, 4.99.

EXAMPLE 28

(+/−)-N-(4-bromo-2,6-dimethylphenyl)-3-[1-(1-methoxymethyl)propyl]-5-methyl-3H-1,2,3-triazolo[4,5-d]pyrimidin-7-amine The product of Part B from Example 27 was combined with 4-bromo-2,6-dimethylaniline in a manner similar to Part C in Example 21, to yield the title compound as a white crystalline solid (mp 137–138° C.). Elemental analysis for $C_{18}H_{23}BrN_6O_2$: Theory C, 51.56; H, 5.54; N, 20.04. Found: C, 51.75; H, 5.43; N, 19.99.

EXAMPLE 29

(+/−)-N-[2,6-dimethyl-4-(methylthio)phenyl]-3-[1-(1-methoxymethyl)propyl]-5-methyl-3H-1,2,3-triazolo[4,5-d]pyrimidin-7-amine The product of Part B from Example 27 was combined with 2,6-dimethyl-4-methylthioaniline in a manner similar to Part C in Example 21, to yield the title compound as a white crystalline solid (mp 128–129° C.). Elemental analysis for $C_{19}H_{26}BrN_6OS$: Theory C, 59.04; H, 6.78. Found: C, 58.49; H, 6.48.

EXAMPLE 30

(+/−)-N-(2-bromo-4,6-dimethoxyphenyl)-3-[1-(1-methoxymethyl)propyl]-5-methyl-3H-1,2,3-triazolo[4,5-d]pyrimidin-7-amine The product of Part B from Example 27 was treated with 2-bromo-4,6-dimethoxyaniline in a manner similar to Part C in Example 21, to yield the title compound as a white crystalline solid (mp 154–155° C.). Elemental analysis for $C_{18}H_{23}BrN_6O_3$: Theory C, 47.90; H, 5.14; N, 18.62. Found: C, 48.28; H, 5.20; N, 18.91.

EXAMPLE 31

(+/−)-N-(2-chloro-4,6-dimethoxyphenyl)-3-[1-(1-methoxymethyl)propyl]-5-methyl-3H-1,2,3-triazolo[4,5-d]pyrimidin-7-amine The product of Part B from Example 27 was treated with 2-chloro-4,6-dimethoxyaniline in a manner similar to Part C in Example 21, to yield the title compound as a white crystalline solid (mp 149–150° C.). Elemental analysis for $C_{18}H_{23}ClN_6O_3$: Theory C, 53.14; H, 5.70; N, 20.66. Found: C, 53.36; H, 5.72; N, 20.49.

EXAMPLE 32

(+/−)-3-[1-(1-methoxymethyl)propyl]-5-methyl-N-(2,4,6-trimethylphenyl)-3H-1,2,3-triazolo[4,5-d]pyrimidin-7-amine Part A 4,6-Dichloro-2-methyl-5-nitropyrimidine (10 g, 48 mmol) dissolved in DMSO/water (480 ml/48 ml) followed by addition of 2,4,6-trimethylaniline (7.43 ml, 52.8 mmol) dropwise via syringe over 30 minutes. The reaction was stirred at room temperature for 18 h and filtered. The solid was washed with water until the filtrant volume reached 600 ml. A 150 ml aliquat was removed, diluted with 1.5 liters water, 100 ml saturated brine, and extracted with 4×100 ml methylene chloride. This procedure was repeated until the remainder of the filtrant had been worked up. The combined organic extracts were dried over anhydrous magnesium sulfate, filtered and concentrated in-vacuo. The crude solid was chromatographed on silica gel (350 g, 97/3 methylene chloride/methanol) to give the desired yellow crystalline product, 10.53 g (76%). $^1$H NMR ($CDCl_3$, 300 MHz) d 12.23 (bs, 1H), 10.60 (s, 1H), 6.95 (s, 2H), 2.34 (2, 3H), 2.33 (s, 3H), 2.16 (s, 6H)

Part B

The product from Part A (3.1 g, 11 mmol) was suspended in phosphorous oxychloride (25 ml) and heated to just under reflux for 1 h, to give a dark homogeneous reaction. The reaction was pipetted slowly and cautiously onto 700 ml ice/water, stirred 30 minutes at room temperature, diluted with 200 ml methylene chloride and transferred to a separatory funnel. The aqueous layer was extracted and reextracted with 3×50 ml methylene chloride. The combined organic extracts were dried over anhydrous magnesium sulfate, filtered and concentrated in-vacuo to constant weight to afford 3.18 g (97%) of the product as a bright yellow solid. $^1$H NMR ($CDCl_3$, 300 MHz) d 8.79 (bs, 1H), 6.96 (s, 2H), 2.42 (s, 3H), 2.33 (s, 3H), 2.15 (s, 6H).

Part C

The product from Part B (2.73 g, 8.9 mmol) was suspended in 60 ml methanol, followed by addition of acetic acid (3.4 ml), cooling to 0° C. in an ice/acetone bath, and addition of iron (1.84 g). The heterogeneous reaction was stirred 5 minutes at 0° C., then refluxed 3. h, cooled, and filtered through celite. The celite pad was washed with 500 ml ethyl acetate. The dark filtrate was concentrated in-vacuo to near dryness, redissolved in ethyl acetate/water and extracted. The aqueous layer was reextracted several times with ethyl acetate. The combined organic extracts were dried over anhydrous magnesium sulfate, filtered and concentrated in-vacuo. Chromatography on silica gel (300 g, 1/1 ethyl acetate/hexanes) gave the product 2.18 g (88%) as an off-white solid. $^1$H NMR ($CDCl_3$, 300 MHz) d 6.93 (s, 2H), 6.25 (bs, 1H), 3.13 (bs, 2H), 2.36 (s, 3H), 2.31 (s, 3H), 2.17 (s, 6H).

Part D

The product from Part C (1.28 g, 4.60 mmol) was dissolved in methylene chloride (20 ml), followed by addition of 50% aq. acetic acid (14 ml) and sodium nitrite (338 mg, 4.89 mmol) in water (1 ml). The reaction was stirred for 3 hours at room temperature, transferred to a separatory funnel, diluted with 100 ml water and 30 ml methylene chloride and extracted. The aqueous layer was reextracted with 3×30 ml methylene chloride. The combined organic layers were washed with brine, dried over anhydrous magnesium sulfate, filtered and concentrated in vacuo. Chromatography on silica gel (200 g, 2/8 ethyl acetate/hexanes) gave the product 1.32 g (88%) as an off-white crystalline solid, mp 186–188° C. CI-HRMS calcd. for $C_{14}H_{15}N_5Cl_1$ (M+H): 288.1016. Found: 288.1008.

Part E

The product from Part D (425 mg, 1.48 mmol) was treated with triethylamine (0.247 ml, 1.78 mmol) and 2-amino-1-methoxy butane (0.183 ml, 1.78 mmol) in ethanol (10 ml) at reflux for 2 h. The reaction was concentrated directly to dryness in vacuo. Chromatography on silica gel (150 g, 1/2 hexanes/ethyl acetate) afforded the purified product, 392 mg (75%) as a crystalline solid, mp 156–157.5° C. Anal. Calcd. for $C_{19}H_{26}N_6O_1$: C, 64.38; H, 7.39; N, 23.71. Found: C, 64.27; H, 7.47; N, 23.62.

Part F

The product from Part E (250 mg, 0.70 mmol) was treated with sodium hydride (42 mg, 1.40 mmol, 80%) in dry dimethylformamide (5 ml). The reaction was stirred 72 hours at room temperature, and 24 h at 50° C., followed by dilution with 100 ml water and extraction with 3×30 ml ethyl acetate. The combined organics were dried over anhydrous magnesium sulfate, filtered, and concentrated to dryness. Chromatography on silica gel (50 g, 1/2 hexanes/ethyl acetate) afforded the purified product, 239 mg (96%) as a crystalline solid, mp 144.5–147° C. Anal. Calcd. for $C_{19}H_{26}N_6O_1$: C, 64.38; H, 7.39; N, 23.71. Found: C, 64.32; H, 7.33; N, 23.78.

EXAMPLE 33

(+/−)-N-ethyl-3-[1-(1-methoxy-methyl)propyl]-5-methyl-N-(2,4,6-trimethylphenyl)-3H-1,2,3-triazolo[4,5-d]pyrimidin-7-amine The product from Example 32, Part F (125 mg, 0.35 mmol) was treated with sodium hydride (13 mg, 0.42 mmol, 80%) and ethyl iodide (42 ml, 0.42 mmol) in dry dimethylformamide (3 ml) and stirred at room temperature for 48 h. The reaction was diluted with 50 ml water, and extracted with 4×30 ml methylene chloride. The combined organic extracts were dried over anhydrous magnesium sulfate, filtered, and concentrated in vacuo to dryness. Chromatography on silica gel (50 g, 3/2 hexanes/ethyl acetate) afforded the desired product, 111 mg (80%) as a clear viscous oil. CI-HRMS calcd. for $C_{21}H_{31}N_6O_1$ (M+H): 383.2559. Found: 383.2567.

EXAMPLE 34

3-[1-(1-ethyl)propyl]-5-methyl-N-(2,4,6-trimethylphenyl)-3H-1,2,3-triazolo[4,5-d]pyrimidin-7-amine Part A
The product from Example 32, Part D (500 mg, 1.74 mmol) was treated with triethylamine (0.29 ml, 2.09 mmol) and 3-aminopentane (0.243 ml, 2.09 mmol) in ethanol (10 ml) at reflux for 2 h. The reaction was concentrated directly to dryness in vacuo. Chromatography on silica gel (100 g, 8/2 hexanes/ethyl acetate) afforded the purified product, 462 mg (79%) as a crystalline solid, mp 184.5–186.5° C. Anal. Calcd. for $C_{19}H_{26}N_6$: C, 67.43; H, 7.74; N, 24.83. Found: C, 67.11; H, 7.59; N, 24.57.

Part B
The product from Part A (300 mg, 0.89 mmol) was treated with sodium hydride (53 mg, 1.78 mmol, 80%) in dry dimethylformamide (5 ml). The reaction was stirred 72 hours at 50° C., followed by dilution with 125 ml water and extraction with 3×40 ml ethyl acetate. The combined organics were dried over anhydrous magnesium sulfate, filtered, and concentrated to dryness. Chromatography on silica gel (75 g, 8/2 hexanes/ethyl acetate) afforded the purified product, 239 mg (80%) as a crystalline solid, mp 160–162° C. Anal. Calcd. for $C_{19}H_{26}N_6$: C, 67.43; H, 7.74; N, 24.83. Found: C, 67.07; H, 7.85; N, 24.51.

EXAMPLE 35

(+/−)-3-[1-(1-ethyl)butyl]-5-methyl-N-(2,4,6-trimethylphenyl)-3H-1,2,3-triazolo[4,5-d]pyrimidin-7-amine Part A
The product from Example 32, Part D (525 mg, 1.82 mmol) was treated with triethylamine (0.305 ml, 3.64 mmol) and 3-aminohexane (0.219 ml, 3.64 mmol) in ethanol (8 ml) at 50° C. for 18 hours. The reaction was concentrated directly to dryness in vacuo. Chromatography on silica gel (140 g, 8/2 hexanes/ethyl acetate) afforded the purified product, 450 mg (70%) as a crystalline solid, mp 170.5–172° C. Anal. Calcd. for $C_{20}H_{28}N_6$: C, 68.15; H, 8.02; N, 23.84. Found: C, 68.10; H, 7.80; N, 23.94.

Part B
The product from Part A (300 mg, 0.85 mmol) was treated with sodium hydride (64 mg, 2.13 mmol, 80%) in dry dimethylformamide (5 ml). The reaction was stirred 24 hours at room temperature, and 24 hours at 50° C., followed by dilution with 125 ml water and extraction with 4×30 ml ethyl acetate. The combined organics were dried over anhydrous magnesium sulfate, filtered, and concentrated to dryness. Chromatography on silica gel (60 g, 8/2 hexanes/ethyl acetate) afforded the purified product, 266 mg (89%) as a crystalline solid, mp 156–157.5° C. Anal. Calcd. for $C_{19}H_{26}N_6$: C, 68.15; H, 8.01; N, 23.84. Found: C, 68.51; H, 8.10; N, 23.94.

EXAMPLE 36

(+/−)-3-[1-(1-ethyl)pentyl]-5-methyl-N-(2,4,6-trimethylphenyl)-3H-1,2,3-triazolo[4,5-d]pyrimidine-7-amine Part A
The product from Example 32, Part D (500 mg, 1.74 mmol) was treated with triethylamine (0.290 ml, 4.35 mmol) and 3-aminoheptane (0.343 ml, 4.35 mmol) in ethanol (8 ml) at 50° C. for 18 h. The reaction was concentrated directly to dryness in vacuo. Chromatography on silica gel (125 g, 8/2 hexanes/ethyl acetate) afforded the purified product, 465 mg (73%) as a crystalline solid, mp 141.5–142.5° C. Anal. Calcd. for $C_{21}H_{30}N_6$: C, 68.82; H, 8.25; N, 22.93. Found: C, 69.11; H, 8.10; N, 23.04.

Part B
The product from Part A (300 mg, 0.82 mmol) was treated with sodium hydride (49 mg, 1.64 mmol, 80%) in dry dimethylformamide (5 ml). The reaction was stirred 24 hours at 50° C., followed by dilution with 125 ml water and extraction with 4×30 ml ethyl acetate. The combined organics were dried over anhydrous magnesium sulfate, filtered, and concentrated to dryness. Chromatography on silica gel (75 g, 8/2 hexanes/ethyl acetate) afforded the purified product, 236 mg (79%) as a crystalline solid, mp 129–130.5° C. Anal. Calcd. for $C_{21}H_{30}N_6$: C, 68.82; H, 8.25; N, 22.93. Found: C, 68.73; H, 8.23; N, 22.90.

EXAMPLE 37

5-methyl-3-[1-(1-propyl)butyl]-N-(2,4,6-trimethylphenyl)-3H-1,2,3-triazolo[4,5-d]pyrimidin-7-amine Part A
The product from Example 32, Part D (255 mg, 0.87 mmol) was treated with triethylamine (0.145 ml, 1.74 mmol) and 4-aminoheptane (0.120 ml, 1.74 mmol) in ethanol (5 ml) at 50° C. for 18 hours. The reaction was concentrated directly to dryness in vacuo. Chromatography on silica gel (60 g, 8/2 hexanes/ethyl acetate) afforded the purified product, 233 mg (73%) as a crystalline solid, mp 145–146.5° C. Anal. Calcd. for $C_{21}H_{30}N_6$: C, 68.82; H, 8.25; N, 22.93. Found: C, 69.09; H, 8.21; N, 23.04.

Part B
The product from Part A (230 mg, 0.63 mmol) was treated with sodium hydride (47 mg, 1.58 mmol, 80%) in dry dimethylformamide (5 ml). The reaction was stirred 24 hours at room temperature, and 24 h at 50° C., followed by dilution with 125 ml water and extraction with 4×30 ml ethyl acetate. The combined organics were dried over anhydrous magnesium sulfate, filtered, and concentrated to dryness. Chromatography on silica gel (60 g, 8/2 hexanes/ethyl acetate) afforded the purified product, 211 mg (92%) as a crystalline solid, mp 143–144.5° C. Anal. Calcd. for $C_{21}H_{30}N_6$: C, 68.82; H, 8.25; N, 22.93. Found: C, 69.08; H, 8.10; N, 23.03.

EXAMPLE 38

3-(2-methoxyethyl)-5-methyl-N-(2,4,6-trimethylphenyl)-3H-1,2,3-triazolo[4,5-d]pyrimidin-7-amine Part A The product from Example 32, Part D (1.07 g, 3.70 mmol) was treated with triethylamine (0.620 ml, 4.44 mmol) and 2-methoxyethylamine (0.386 ml, 4.44 mmol) in ethanol (20 ml) at reflux for 3 h. The reaction was concentrated directly to dryness in vacuo. Chromatography on silica gel (150 g, 1/1 hexanes/ethyl acetate) afforded the purified product, 1.18 g (97%) as a crystalline solid, mp 141.5–143.5° C. Anal. Calcd. for $C_{17}H_{22}N_6O_1$: C, 62.56; H, 6.79; N, 25.75. Found: C, 62.54; H, 6.78; N, 25.70.

Part B

The product from Part A (325 mg, 1.00 mmol) was treated with sodium hydride (60 mg, 2.00 mmol, 80%) in dry dimethylformamide (5 ml). The reaction was stirred 72 hours at room temperature, and 24 hours at 50° C., followed by dilution with 125 ml water and extraction with 4×30 ml ethyl acetate. The combined organics were dried over anhydrous magnesium sulfate, filtered, and concentrated to dryness. Chromatography on silica gel (50 g, 1/2 hexanes/ethyl acetate) afforded the purified product, 321 mg (99%) as a crystalline solid, mp 171.5–173.5° C. Anal. Calcd. for $C_{17}H_{22}N_6O_1$: C, 62.56; H, 6.79. Found: C, 62.24; H, 6.89.

EXAMPLE 39

N-ethyl-3-(2-methoxyethyl)-5-methyl-N-(2,4,6-trimethylphenyl)-3H-1,2,3-triazolo[4,5-d]pyrimidin-7-amine The product from Example 38, Part B (150 mg, 0.46 mmol) was treated with sodium hydride (17 mg, 0.55 mmol, 80%) and ethyl iodide (55 ml, 0.69 mmol) in dry dimethylformamide (3 ml) and stirred at room temperature for 48 h. The reaction was diluted with 50 ml water, and extracted with 4×30 ml methylene chloride. The combined organic extracts were dried over anydrous magnesium sulfate, filtered, and concentrated in vacuo to dryness. Chromatography on silica gel (50 g, 1/1 hexanes/ethyl acetate) afforded the desired product, 144 mg (88%) as a clear viscous oil. CI-HRMS calcd. for $C_{19}H_{27}N_6O_1$ (M+H): 355.2246. Found: 355.2240.

EXAMPLE 40

N-(2-Methyl-4-bromophenyl)-3-[1-(1-propyl)butyl]-5-methyl-3H-1,2,3-triazolo[4,5-d]pyrimidin-7-amine Part A 4,6-Dichloro-2-methyl-5-nitropyrimidine (5.2 g, 25 mmol) dissolved in DMSO (480 ml) followed by addition of 2-methyl-4-bromoaniline (4.65 g, 25 mmol) dropwise via syringe over 30 minutes. The reaction was stirred at RT for 18 h, followed by addition of 800 ml water. The resulting precipitate was filtered and dried to constant weight affording 7.02 g (83%) of the desired pyrimidone as a yellow solid.

Part B

The product from Part A (6.95 g, 20.5 mmol) was treated with phosphorous oxychloride (120 ml) and brought to reflux for 20 minutes. The reaction was cooled, and slowly quenched on 3 L of ice/water. The resultant precipitate was filtered and dried. Chromatography on silica gel (500 g, 8/2 hexanes/ethyl acetate) gave the purified product, 5.4 g (74%), as a yellow solid.

Part C

The product from Part B (5.4 g, 15.2 mmol) was suspended in 120 ml methanol, followed by addition of acetic acid (6.8 ml), cooling to 0° C. in an ice/acetone bath, and addition of iron (4.23 g) under the same conditions described in Example 32, Part C. The resultant brown solid was used directly in the next reaction.

Part D

The product from Part C (15.2 mmol) was dissolved in methylene chloride (100 ml), followed by addition of 50% aq. acetic acid (50 ml) and sodium nitrite (1.15 g, 16.70 mmol) in water (5ml) under the same conditions described in Example 32, Part D. Chromatography of the crude product on silica gel (400 g, 2/8 ethyl acetate/hexanes) gave the product 3.15 g (62% from Part C) as an off-white crystalline solid, mp 145–147.5° C.

Part E

The product from Part D (600 mg, 1.78 mmol) was treated with triethylamine (300 ml, 2.14 mmol) and 4-aminoheptane (246 ml, 2.14 mmol) in ethanol (10 ml) at 50° C. for 18 h. The reaction was concentrated directly to dryness in vacuo. Chromatography on silica gel (125 g, 8/2 hexanes/ethyl acetate) afforded the purified product, 600 mg (81%) as a crystalline solid, mp 155–156° C. Anal. Calcd. for $C_{19}H_{25}N_6Br_1$: C, 54.68; H, 6.05; N. 20.14. Found: C, 54.36; H, 5.71; N, 20.24.

Part F

The product from Part E (350 mg, 0.84 mmol) was treated with sodium hydride (63 mg, 2.10 mmol, 80%) in dry dimethylformamide (5 ml). The reaction was stirred 24 h at room temperature, and 24 h at 50° C., followed by dilution with 125 ml water and extraction with 4×30 ml ethyl acetate. The combined organics were dried over anhydrous magnesium sulfate, filtered, and concentrated to dryness. Chromatography on silica gel (60 g, 8/2 hexanes/ethyl acetate) afforded the purified product, 333 mg (95%) as a crystalline solid, mp 126.5–128° C. Anal. Calcd. for $C_{19}H_{25}N_6Br_1$: C, 54.68; H, 6.05; N, 20.14. Found: C, 54.90; H, 6.04; N, 20.40.

EXAMPLE 41

(+/−)-3-[1-(1-ethyl)butyl]-5-methyl-N-(2-methyl-4-bromophenyl)-3H-1,2,3-triazolo[4,5-d]pyrimidin-7-amine Part A The product from Example 40, Part D (600 mg, 1.78 mmol) was treated with triethylamine (0.300 ml, 2.14 mmol) and 3-aminohexane (0.214 ml, 2.14 mmol) in ethanol (10 ml) at 50° C. for 18 h. The reaction was concentrated directly to dryness in vacuo. Chromatography on silica gel (75 g, 8/2 hexanes/ethyl acetate) afforded the purified product, 616 mg (86%) as a crystalline solid, mp 117.5–119.5° C. Anal. Calcd. for $C_{18}H_{23}N_6Br_1$: C, 53.60; H, 5.76; N, 20.84. Found: C, 53.53; H, 5.72; N, 20.95.

Part B

The product from Part A (450 mg, 1.12 mmol) was treated with sodium hydride (84 mg, 2.80 mmol, 80%) in dry dimethylformamide (10 ml). The reaction was stirred 72 hours at room temperature, followed by dilution with 125 ml water and extraction with 4×30 ml ethyl acetate. The combined organics were dried over anhydrous magnesium sulfate, filtered, and concentrated to dryness. Chromatography on silica gel (75 g, 8/2 hexanes/ethyl acetate) afforded the purified product, 425 mg (94%) as a crystalline solid, mp 99–101° C.

EXAMPLE 42

(+/−)-N-(4-bromo-2-methylphenyl)-3-[1-(1-methoxymethyl)propyl]-5-methyl-3H-1,2,3-triazolo[4,5-d]pyrimidin-7-amine Part A The product from Example 40, Part D (800 mg, 2.37 mmol) was treated with triethylamine (0.400 ml, 2.84 mmol) and 2-amino-1-methoxybutane (0.341 ml, 2.84 mmol) in ethanol (20 ml) at room temperature for 48 h. The reaction was concentrated directly to dryness in vacuo. Chromatography on silica gel (150 g, 8/2 hexanes/ethyl acetate) afforded the purified product, 697 mg (72%) as a crystalline solid, mp 144.5–146° C. Anal. Calcd. for $C_{17}H_{21}N_6Br_1O_1$: C, 50.38; H, 5.22; N, 20.74. Found: C, 50.35; H, 5.23; N, 20.58.

Part B

The product from Part A (550 mg, 1.36 mmol) was treated with sodium hydride (102 mg, 3.40 mmol, 80%) in dry dimethylformamide (8 ml). The reaction was stirred 72 h at room temperature, followed by dilution with 125 ml water and extraction with 4×30 ml ethyl acetate. The combined organics were dried over anhydrous magnesium sulfate, filtered, and concentrated to dryness. Chromatography on silica gel (75 g, 8/2 hexanes/ethyl acetate) afforded the purified product, 520 mg (94%) as a crystalline solid.

EXAMPLE 43

(+/−)-3-[1-(1-ethyl)pentyl]-5-methyl-N-[(2,4,6-trimethyl)-3-pyridyl-]-3H-1,2,3-triazolo[4,5-d]pyrimidin-7-amine Part A To 2,4-dichloro-2-methyl-5-nitropyrimidine (10.10 g, 48.60 mmol) in dry tetrahydrofuran (200 ml) and triethylamine (6.8 ml, 48.6 mmol) was added 3-amino-2,4,6-trimethylpyridine (3.30 g, 24.3 mmol) in tetrahydrofuran (30 ml) via canulation over 10 minutes at room temperature. The reaction was stirred 72 h, diluted with 1 L of water, and extracted with 4×200 ml ethyl acetate. The combined organic extracts were dried over anhydrous magnesium sulfate, filtered, and concentrated to dryness in vacuo. Chromatography on silica gel (300 g, 1/1 ethyl acetate/hexanes) afforded the purified product, 4.8 g (64%) as a white solid. $^1$H NMR (300 MHz, CDCl3) d 8.79 (bs, 1H), 6.97 (s, 1H), 2.54 (s, 3H), 2.43 (s, 3H), 2.40 (s, 3H), 2.17 (s, 3H).

Part B

The product from Part A (4.8 g, 15.60 mmol) was treated with iron (4.36 g, 78.00 mmol) in methanol (110 ml) and acetic acid (6 ml) under the same reaction conditions described in Example 32, Part C. Chromatography on silica gel (250 g, 9/1 methylene chloride/methanol) afforded the purified reduction product, 3.1 g, (72%) as a white solid. $^1$H NMR (300 MHz, CDCl3) d 6.94 (s, 1H), 6.26 (bs, 1H), 3.36 (bs, 1H), 2.52 (s, 3H), 2.41 (s, 3H), 2.35 (s, 3H), 2.16 (s, 3H).

Part C

The product from Part B (2.1 g, 7.56 mmol) was treated with sodium nitrite (574 mg, 8.32 mmol) in methylene chloride (44 ml) and 50% aq. acetic acid (25 ml) under the same reactions conditions described in Example 32, Part D. Chromatography on silica gel (125 g, 1/1 ethyl acetate/hexanes) afforded the purified cyclized product, 1.7 g (78%) as a white solid, mp 204.5–206° C. Anal. Calcd. for $C_{13}H_{13}N_6Cl_1$; C, 54.08; H, 4.55; N, 29.11. Found: C, 53.94; H, 4.43; N, 28.79.

Part D

The product from Part C (300 mg, 1.04 mmol) was treated with triethylamine (175 ml, 1.25 mmol) and 3-aminoheptane (243 ml, 1.25 mmol) in ethanol (10 ml) at reflux for 2.5 hours. The reaction was concentrated directly to dryness in vacuo. Chromatography on silica gel (20 g, 1/2 hexanes/ethyl acetate) afforded the purified product, 356 mg (93%) as a crystalline solid, mp 122–130° C. Anal. Calcd. for $C_{20}H_{29}N_7$; C, 65.37; H, 7.95; N, 26.68. Found: C, 65.35; H, 7.95; N, 26.82.

Part E

The product from Part D (160 mg, 0.44 mmol) was treated with sodium hydride (27 mg, 0.88 mmol, 80%) in dry dimethylformamide (4 ml). The reaction was stirred 24 hours at room temperature, and 100 hours at 50° C., followed by dilution with 100 ml water and extraction with 3×30 ml ethyl acetate. The combined organics were dried over anhydrous magnesium sulfate, filtered, and concentrated to dryness. Preparative HPLC [(25–65%) acetonitrile:trifluoroacetic acid/water:trifluoroacetic acid, Dynamax C18 column] afforded the purified product, 60 mg (38%) as an amorphous foam. CI-HRMS calcd. for $C_{20}H_{29}N_7$ (M+H): 368.2545. Found: 368.2563.

EXAMPLE 44

(+/−)-N-ethyl-3-[1-(1-ethyl)pentyl]-5-methyl-N-[(2,4,6-trimethyl)-3-pyridyl-]-3H-1,2,3-triazolo[4,5-d]pyrimidin-7-amine The product from Example 43, Part E (29 mg, 0.08 mmol) was treated with sodium hydride (3 mg, 0.1 mmol, 80%) and ethyl iodide (9.6 ml, 0.12 mmol) in dry dimethylformamide (1 ml) and stirred at room temperature for 168 h. The reaction was diluted with 10 ml water, and extracted with 4×5 ml ethyl acetate. The combined organic extracts were dried over anhydrous magnesium sulfate, filtered, and concentrated in vacuo to dryness. Chromatography on silica gel (10 g, 1/1 hexanes/ethyl acetate) afforded the desired product, 19.7 mg (63%) as a clear viscous oil. CI-HRMS calcd. for $C_{22}H_{33}N_7$ (M+H): 396.2876. Found: 396.2876.

EXAMPLE 45

(+/−)-3-[1-(1-ethyl)butyl]-5-methyl-N-[(2,4,6-trimethyl)3-pyridyl-]-3H-1,2,3-triazolo[4,5-d]pyrimidin-7-amine Part A The product from Example 43, Part C (546 mg, 1.89 mmol) was treated with triethylamine (0.316 ml, 2.27 mmol) and 3-aminohexane (0.210 mg, 2.07 mmol) in ethanol (15 ml) at reflux for 2.5 h. The reaction was concentrated directly to dryness in vacuo. Chromatography on silica gel (50 g, ethyl acetate) afforded the purified product, 530 mg (79%) as a crystalline solid, mp 155.5–158° C. Anal. Calcd. for $C_{19}H_{27}N_7$; C, 64.56; H, 7.71; N, 27.74. Found: C, 64.59; H, 7.62; N, 27.91.

Part B

The product from Part A (400 mg, 1.13 mmol) was treated with sodium hydride (94 mg, 3.11 mmol, 80%) in dry dimethylformamide (12 ml). The reaction was stirred 72 h at 50° C., followed by dilution with 100 ml water and extraction with 4×30 ml ethyl acetate. The combined organics were dried over anhydrous magnesium sulfate, filtered, and concentrated to dryness. Chromatography on silica gel (50 g, 1/3 hexanes/ethyl acetate) afforded the purified product, 355 mg (89%) as a crystalline solid, mp 132–140.5° C. Anal. Calcd. for $C_{19}H_{27}N_7$: C, 64.56; H, 7.71; N, 27.74. Found: C, 64.52; H, 7.58; N, 27.97.

EXAMPLE 46

N-ethyl-3-[1-(1-ethyl)butyl]-5-methyl-N-[(2,4,6-trimethyl)-3-pyridyl-]-3H-1,2,3-triazolo[4,5-d]pyrimidin-7-amine The product from Example 45, Part B (250 mg, 0.71 mmol) was treated with sodium hydride (26 mg, 0.85 mmol, 80%) and ethyl iodide (0.85 ml, 1.07 mmol) in dry dimethylformamide (7 ml) and stirred at room temperature for 15 h. The reaction was diluted with 150 ml water, and extracted with 3×30 ml ethyl acetate. The combined organic extracts were dried over anhydrous magnesium sulfate, filtered, and concentrated in vacuo to dryness. Chromatography on silica gel (20 g, 1/3 hexanes/ethyl acetate) afforded the desired product, 221 mg (81%) as a clear viscous oil.

EXAMPLE 47

3-[1-(1-propyl)butyl]-5-methyl-N-[(2,4,6-trimethyl)-3-pyridyl-]-3H-1,2,3-triazolo[4,5-d]pyrimidin-7-amine Part A The product from Example 43, Part C (700 mg, 2.42 mmol) was treated with triethylamine (0.405 ml, 2.91 mmol) and 4-aminoheptane (335 mg, 2.91 mmol) in ethanol (20 ml) at reflux for 2.5 h. The reaction was concentrated directly to dryness in vacuo. Chromatography on silica gel (50 g, 1/3 hexanes/ethyl acetate) afforded the purified product, 845 mg (96%) as a crystalline solid, mp 135.5–137.5° C. Anal. Calcd. for $C_{20}H_{29}N_7$: C, 65.37; H, 7.95; N, 26.68. Found: C, 65.71; H, 7.70; N, 26.95.

Part B

The product from Part A (600 mg, 1.63 mmol) was treated with sodium hydride (147.5 mg, 4.89 mmol, 80%) in dry dimethylformamide (15 ml). The reaction was stirred 15 h at 50° C., followed by dilution with 200 ml water and extraction with 5×30 ml ethyl acetate. The combined organics were dried over anhydrous magnesium sulfate, filtered, and concentrated to dryness. Chromatography on silica gel (50 g, 1/3 hexanes/ethyl acetate) afforded the purified product, 560 mg (93%) as a crystalline solid, mp 128–130° C. CI-HRMS calcd. for $C_{20}H_{29}N_7$ (M+H): 368.2561. Found: 368.2563.

EXAMPLE 48

N-ethyl-3-[1-(1-propyl)butyl]-5-methyl-N-[(2,4,6-trimethyl)-3-pyridyl-]-3H-1,2,3-triazolo[4,5-d]pyrimidin-7-amine The product from Example 47, Part B (400 mg, 1.09 mmol) was treated with sodium hydride (40 mg, 1.31 mmol, 80%) and ethyl iodide (0.130 ml, 1.63 mmol) in dry dimethylformamide (10 ml) and stirred at room temperature for 15 hours. The reaction was diluted with 150 ml water, and extracted with 3×30 ml ethyl acetate. The combined organic extracts were dried over anhydrous magnesium sulfate, filtered, and concentrated in vacuo to dryness. Chromatography on silica gel (20 g, 1/3 hexanes/ethyl acetate) afforded the desired product, 373 mg (87%) as a clear viscous oil.

EXAMPLE 49

(+/−)-3-[1-(1-methoxymethyl)propyl]-5-methyl-N-[(2,4,6-trimethyl)-3-pyridyl-]-3H-1,2,3-triazolo[4,5-d]pyrimidin-7-amine Part A The product from Example 43, Part C (700 mg, 2.42 mmol) was treated with triethylamine (0.405 ml, 2.91 mmol) and 2-aminomethoxybutane (0.350 ml, 2.91 mmol) in ethanol (20 ml) at reflux for 2.5 h. The reaction was concentrated directly to dryness in vacuo. Chromatography on silica gel (50 g, 1/1 hexanes/tetrahydrofuran) afforded the purified product, 845 mg (98%) as a crystalline solid, mp 132–136.5° C. Anal. Calcd. for $C_{18}H_{25}N_7O_1$; C, 60.82; H, 7.1; N, 27.58. Found: C, 61.13; H, 6.89; N, 27.54.

Part B

The product from Part A (600 mg, 1.68 mmol) was treated with sodium hydride (151.2 mg, 5.04 mmol, 80%) in dry dimethylformamide (15 ml). The reaction was stirred 15 hours at 50° C., followed by dilution with 100 ml water and extraction with 4×30 ml ethyl acetate. The combined organics were dried over anhydrous magnesium sulfate, filtered, and concentrated to dryness. Chromatography on silica gel (50 g, 1/1 hexanes/tetrahydrofuran) afforded the purified product, 500 mg (83%) as a crystalline solid, mp 141.5–144° C. Anal. Calcd. for $C_{18}H_{25}N_7O_1$; C, 60.82; H, 7.1; N, 27.58. Found: C, 60.94; H, 6.95; N, 27.46.

EXAMPLE 50

(+/−)-N-ethyl-3-[1-(1-methoxy methyl)propyl]-5-methyl-N-[(2,4,6-trimethyl)-3-pyridyl-]-3H-1,2,3-triazolo[4,5-d]pyrimidin-7-amine The product from Example 49, Part B (350 mg, 0.99 mmol) was treated with sodium hydride (36 mg, 1.19 mmol, 80%) and ethyl iodide (0.119 ml, 1.49 mmol) in dry dimethylformamide (10 ml) and stirred at room temperature for 15 h. The reaction was diluted with 150 ml water, and extracted with 3×30 ml ethyl acetate. The combined organic extracts were dried over anhydrous magnesium sulfate, filtered, and concentrated in vacuo to dryness. Chromatography on silica gel (20 g, 1/1 hexanes/tetrahydrofuran) afforded the desired product, 338 mg (89%) as a clear viscous oil.

EXAMPLE 51

N-(2,4-dibromophenyl)-5-methyl-3-(1-propyl)butyl-3H-1,2,3-triazolo[4,5-d]pyrimidin-7-amine Part A 4-Aminoheptane (2.5 g) was added to a solution of 4,6-ditosyloxy-2-methyl-5-nitropyrimidine (10.5 g) and N,N-diisopropylethylamine (3.8 mL) in dichloromethane (219 mL). The reaction was stirred under nitrogen for 5 h at room temperature and then extracted with water. The organic layer was dried over anhydrous magnesium sulfate and concentrated to yield N-(1-propyl)butyl-2-methyl-5-nitro-4-tosyloxypyrimidin-6-amine as a pale yellow solid (9.1 g)

Part B

The product of part A (9.0 g), anhydrous toluene (200 mL), N,N-diisopropylethylamine (3.8 mL) and 2,4-dibromoaniline (5.5 g) were heated at 65° C. for 16 h under nitrogen. The reaction was added to saturated aqueous $NH_4Cl$ and extracted with dichloromethane (3 times). The combined organic layers were dried over anhydrous magnesium sulfate and concentrated to yield N-4-(2,4-dibromophenyl)-N-[6-(1-propyl)butyl]-2-methyl-5-nitro-pyrimidin-4,6-diamine as a yellow solid (6.5 g).

Part C

The product of part B (6.5 g), 1,4-dioxane (65 mL), water (65 mL), sodium dithionite (18.0 g) and 40% ammonium hydroxide (6.5 mL) were stirred for 3 h at room temperature. The reaction mixture was added to saturated aqueous $NH_4Cl$ and extracted with ethyl acetate (3 times). The combined organic layers were dried over anhydrous magnesium sulfate and concentrated. The residue was purified by flash column chromatography on silica gel using EtOAc/hexane (2:8) to yield N-[4-(2,4-dibromophenyl)]-N-[6-(1-propyl)butyl]-2-methyl-5-aminopyrimidin-4,6-diamine as a pale yellow solid (5.1 g).

Part D

The product of part C (5.0 g) was dissolved in a 2:1:1 mixture of dichloromethane, acetic acid and water. To this solution was added sodium nitrite (0.9 g) and the resulting solution was stirred for 2 h at room temperature. The reaction was added to an equal volume of water and extracted with dichloromethane (3 times). The combined organic layers were washed with saturated aqueous NaHCO$_3$, then were dried over anhydrous magnesium sulfate and concentrated. The residue was purified by flash column chromatography on silica gel using ethyl acetate/hexane (2:8) to yield N-(1-propyl)butyl-3-(2,4-dibromophenyl)-5-methyl-3H-1,2,3-triazolo[4,5-d]pyrimidin-7-amine as a white solid (3.9 g). A small amount of the title compound, N-(2,4-dibromophenyl)-5-methyl-3-(1-propyl)butyl-3H-1,2,3-triazolo[4,5-d]pyrimidin-7-amine (0.18 g) was also isolated from the chromatography.

Part E

Sodium hydride (0.24 g) was added to a solution of the product of part D (3.9 g) in anhydrous DMF (82 mL). The resulting solution was stirred for 16 h under nitrogen and the partitioned between ethyl acetate and water. The organic layer was washed with brine, dried over anhydrous magnesium sulfate and concentrated. The resulting solid was recrystallized from boiling 2-propanol to afford the title compound as a white crystalline solid (3.6 g).

EXAMPLE 52

N-[4-acetyl-2-bromophenyl]-5-methyl-3-(1-propyl)butyl-3H-1,2,3-triazolo[4,5-d]pyrimidin-7-amine Bis(triphenylphosphine)palladium dichloride (11.9 mg), tetrakis(triphenylphosphine)palladium (19.6 mg) and 1-ethoxyvinyltributyltin (299 mg) were added to the product of Part E, from Example 51 (0.33 g) dissolved in toluene (5 mL). The reaction was heated to reflux and stirred overnight. The solvent was then removed under vacuum and the residue partitioned between ether and aqueous saturated NaF. The mixture was then filtered and separated. The organic layer was then washed with 1N HCl, dried over anhydrous magnesium sulfate and concentrated. The residue was purified by flash column chromatography on silica gel using ethyl acetate/hexane (2:8) to yield the title compound.

EXAMPLE 53

N-[2-bromo-4-(1-methylethyl)phenyl]-3-[1-(N,N-dimethylamino-methyl)butyl]-5-methyl-3H-1,2,3-triazolo[4,5-d]pyrimidin-7-amine Part A A solution of N-CBZ-d, 1-norvaline (TCI America) in THF (0.5 M) is treated in sequence with 1-hydroxybenzotriazole hydrate (1.2 eq), dimethylamine hydrochloride (1.3 eq), triethylamine (1.4 eq), and dicyclohexylcarbodiimide (1.2 eq). After stirring overnight, the mixture is filtered, which is followed by aqueous workup and chromatography, to afford N,N-dimethyl-N'-CBZ-d, 1-norvalinamide, as an oil (TLC Rf=0.10, 30:70 ethyl acetate-hexane).

Part B

A solution of the CBZ compound from Part A above is dissolved in methanol (1 M), and 5% Pd on carbon is added. The mixture is submitted to hydrogenation in the usual Parr shaker apparatus (50 PSI, overnight). The resulting mixture is filtered through celite and evaporated to afford sufficiently pure product, N,N-dimethyl-d,1-norvalinamide, as an oil (TLC baseline in 30:70 ethyl acetate-hexane).

Part C

The amine from Part B is elaborated to title compound by using the procedure outlined in Example 32 or 51. Spectral data. $^1$H NMR (300 MHz, CDCl3): d 8.61 (1H, d, J=8.4 Hz), 8.20 (1H, br s), 7.48 (1H, d, J=1.8 Hz), 7.26 (1H, dd, J=8.4, 1.8 Hz), 5.08–4.98 (1H, m), 3.27 (1H, dd, J=12.6, 9.7 Hz), 2.91 (1H, heptet, J=7.0 Hz), 2.68 (3H, s), 2.67 (1H, dd, J=1.2.6 Hz), 2.22 (6H, s), 2.21–2.11 (1H, m), 1.99–1.89 (1H, m), 1.29–1.19 (1H, m), 1.27 (6H, d, J=7.0 Hz), 1.16–1.05 (1H, m), 0.88 (3H, t, J=7.1 Hz). MS(NH$_3$-CI): m/e 464 (3), 463 (25), 462 (100), 461 (29), 460 (98).

The compounds of Examples 54–208 can be made by the methods exemplified in Examples 1–53.

TABLE 1

3H-1,2,3-triazolo[4,5-d]pyrimidines:

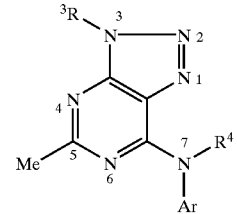

| No. | Ar | R$^3$ | R$^4$ |
|---|---|---|---|
| 54 | 2-Br-4-i-Pr-Ph | C(Me)$_2$CH$_2$—OCH$_3$ | H |
| 55 | 2-Br-4-i-Pr-Ph | cyclopentyl | H |
| 56 | 2-Br-4,6-(OMe)$_2$-Ph | CH(Bz)CH$_2$—OCH$_3$ | H |
| 57 | 2-Cl-4,6-(OMe)$_2$-Ph | CH(Bz)CH$_2$—OCH$_3$ | H |
| 58 | 4-i-Pr-2-SMe-Ph | CH(Bz)CH$_2$—OCH$_3$ | H |
| 59 | 4-i-Pr-2-SO$_2$Me-Ph | CH(Bz)CH$_2$—OCH$_3$ | H |
| 60 | 4-(COMe)-2-Br-Ph | CH(Bz)CH$_2$—OCH$_3$ | H |
| 61 | 2-Br-4-CF$_3$-Ph | CH(Bz)CH$_2$—OCH$_3$ | H |
| 62 | 4-Br-2,6-(Me)$_2$-Ph | CH(Bz)CH$_2$—OCH$_3$ | H |
| 63 | 2,6-(Me)$_2$-4-SO$_2$Me-Ph | CH(Bz)CH$_2$—OCH$_3$ | H |
| 64 | 2,4,6-(Me)$_3$Ph | CH(Bz)CH$_2$—OCH$_3$ | H |
| 65 | 2,6-(Me)$_2$-4-CF$_3$-Ph | CH(Bz)CH$_2$—OCH$_3$ | H |
| 66 | 2-Br-4,6-(Me)$_2$-Ph | CH(Bz)CH$_2$—OCH$_3$ | H |
| 67 | 4-Br-2-Me-Ph | CH(Bz)CH$_2$—OCH$_3$ | H |
| 68 | 4-N(Et)$_2$-2-Me-Ph | CH(Bz)CH$_2$—OCH$_3$ | H |
| 69 | 4-I-2-Me-Ph | CH(Bz)CH$_2$—OCH$_3$ | H |
| 70 | 2-I-4-i-Pr-Ph | CH(Bz)CH$_2$—OCH$_3$ | H |
| 71 | 2-Br-4-SMe-Ph | CH(Bz)CH$_2$—OCH$_3$ | H |
| 72 | 2-Br-4-SO$_2$Me-Ph | CH(Bz)CH$_2$—OCH$_3$ | H |
| 73 | 2-Br-4-N(Me)$_2$-6-OMe-Ph | CH(Bz)CH$_2$—OCH$_3$ | H |
| 74 | 2-Br-4,6-(OMe)$_2$-Ph | CH(Et)Bu$^n$ | H |
| 75 | 2-Cl-4,6-(OMe)$_2$-Ph | CH(Et)Bu$^n$ | H |
| 76 | 4-i-Pr-2-SMe-Ph | CH(Et)Bu$^n$ | H |
| 77 | 4-i-Pr-2-SO$_2$Me-Ph | CH(Et)Bu$^n$ | H |
| 78 | 4-(COMe)-2-Br-Ph | CH(Et)Bu$^n$ | H |
| 79 | 2-Br-4-CF$_3$-Ph | CH(Et)Bu$^n$ | H |
| 80 | 4-Br-2,6-(Me)$_2$-Ph | CH(Et)Bu$^n$ | H |
| 81 | 2,6-(Me)$_2$-4-SO$_2$Me-Ph | CH(Et)Bu$^n$ | H |
| 82 | 2,6-(Me)$_2$-4-SMe-Ph | CH(Et)Bu$^n$ | H |
| 83 | 2,6-(Me)$_2$-4-CF$_3$-Ph | CH(Et)Bu$^n$ | H |
| 84 | 2-Br-4,6-(Me)$_2$-Ph | CH(Et)Bu$^n$ | H |
| 85 | 4-Br-2-Me-Ph | CH(Et)Bu$^n$ | H |
| 86 | 4-N(Et)$_2$-2-Me-Ph | CH(Et)Bu$^n$ | H |
| 87 | 4-I-2-Me-Ph | CH(Et)Bu$^n$ | H |
| 88 | 2-I-4-i-Pr-Ph | CH(Et)Bu$^n$ | H |
| 89 | 2-Br-4-SO$_2$Me-Ph | CH(Et)Bu$^n$ | H |
| 90 | 2-Br-4-N(Me)$_2$-6-OMe-Ph | CH(Et)Bu$^n$ | H |
| 91 | 2,4-[SMe]$_2$-Ph | CH(Et)Bu$^n$ | H |
| 92 | 2,4-[SO$_2$Me]$_2$-Ph | CH(Et)Bu$^n$ | H |
| 93 | 2-Br-4,6-(OMe)$_2$-Ph | CH(Et)Pr$^n$ | H |
| 94 | 2-Cl-4,6-(OMe)$_2$-Ph | CH(Et)Pr$^n$ | H |
| 95 | 4-i-Pr-2-SMe-Ph | CH(Et)Pr$^n$ | H |
| 96 | 4-i-Pr-2-SO$_2$Me-Ph | CH(Et)Pr$^n$ | H |
| 97 | 4-(COMe)-2-Br-Ph | CH(Et)Pr$^n$ | H |
| 98 | 4-Br-2-CF$_3$-Ph | CH(Et)Pr$^n$ | H |
| 99 | 4-Br-2,6-(Me)$_2$-Ph | CH(Et)Pr$^n$ | H |
| 100 | 2,6-(Me)$_2$-4-SMe-Ph | CH(Et)Pr$^n$ | H |
| 101 | 2,6-(Me)$_2$-4-SO$_2$Me-Ph | CH(Et)Pr$^n$ | H |

TABLE 1-continued 3H-1,2,3-triazolo[4,5-d]pyrimidines:

| No. | Ar | $R^3$ | $R^4$ |
|---|---|---|---|
| 102 | 2,6-(Me)$_2$-4-CF$_3$-Ph | CH(Et)Pr$^n$ | H |
| 103 | 2-Br-4,6-(Me)$_2$-Ph | CH(Et)Pr$^n$ | H |
| 104 | 4-N(Et)$_2$-2-Me-Ph | CH(Et)Pr$^n$ | H |
| 105 | 2-I-4-i-Pr-Ph | CH(Et)Pr$^n$ | H |
| 106 | 2-Br-4-SMe-Ph | CH(Et)Pr$^n$ | H |
| 107 | 2-Br-4-SO$_2$Me-Ph | CH(Et)Pr$^n$ | H |
| 108 | 2-Br-4,6-(OMe)$_2$-Ph | CH(C$_2$H$_5$)$_2$ | H |
| 108 | (m.p. 163–165° C.) | | |
| 109 | 2-Cl-4,6-(OMe)$_2$-Ph | CH(C$_2$H$_5$)$_2$ | H |
| 109 | (m.p. 166–167° C.) | | |
| 110 | 4-i-Pr-2-SMe-Ph | CH(C$_2$H$_5$)$_2$ | H |
| 110 | (m.p. 89–90° C.) | | |
| 111 | 4-i-Pr-2-SO$_2$Me-Ph | CH(C$_2$H$_5$)$_2$ | H |
| 112 | 4-(COMe)-2-Br-Ph | CH(C$_2$H$_5$)$_2$ | H |
| 113 | 2-Br-4-CF$_3$-Ph | CH(C$_2$H$_5$)$_2$ | H |
| 114 | 4-Br-2,6-(Me)$_2$-Ph | CH(C$_2$H$_5$)$_2$ | H |
| 114 | (m.p. 160–162° C.) | | |
| 115 | 2,6-(Me)$_2$-4-SMe-Ph | CH(C$_2$H$_5$)$_2$ | H |
| 116 | 2,6-(Me)$_2$-4-SO$_2$Me-Ph | CH(C$_2$H$_5$)$_2$ | H |
| 117 | 2,6-(Me)$_2$-4-CF$_3$-Ph | CH(C$_2$H$_5$)$_2$ | H |
| 118 | 2-Br-4,6-(Me)$_2$-Ph | CH(C$_2$H$_5$)$_2$ | H |
| 119 | 4-N(Et)$_2$-2-Me-Ph | CH(C$_2$H$_5$)$_2$ | H |
| 120 | 4-I-2-Me-Ph | CH(C$_2$H$_5$)$_2$ | H |
| 121 | 2-I-4-i-Pr-Ph | CH(C$_2$H$_5$)$_2$ | H |
| 122 | 2-Br-4-SMe-Ph | CH(C$_2$H$_5$)$_2$ | H |
| 123 | 2-Br-4-SO$_2$Me-Ph | CH(C$_2$H$_5$)$_2$ | H |
| 124 | 2-Br-4-N(Me)$_2$-6-OMe-Ph | CH(C$_2$H$_5$)$_2$ | H |
| 125 | 2,4-[S(O)$_2$Me]$_2$-Ph | CH(C$_2$H$_5$)$_2$ | H |
| 126 | 2-Cl-4,6-(OMe)$_2$-Ph | CH(n-C$_3$H$_7$)$_2$ | H |
| 127 | 4-i-Pr-2-S(O)$_2$Me-Ph | CH(n-C$_3$H$_7$)$_2$ | H |
| 128 | 4-(COMe)-2-Br-Ph | CH(n-C$_3$H$_7$)$_2$ | H |
| 129 | 4-Br-2-CF$_3$-Ph | CH(n-C$_3$H$_7$)$_2$ | H |
| 130 | 4-Br-2,6-(Me)$_2$-Ph | CH(n-C$_3$H$_7$)$_2$ | H |
| 131 | 2,6-(Me)$_2$-4-S(O)$_n$Me-Ph | CH(n-C$_3$H$_7$)$_2$ | H |
| 132 | 2,6-(Me)$_2$-4-CF$_3$-Ph | CH(n-C$_3$H$_7$)$_2$ | H |
| 133 | 2-Br-4,6-(Me)$_2$-Ph | CH(n-C$_3$H$_7$)$_2$ | H |
| 134 | 4-Cl-2-Me-Ph | CH(n-C$_3$H$_7$)$_2$ | H |
| 135 | 4-N(Et)$_2$-2-Me-Ph | CH(n-C$_3$H$_7$)$_2$ | H |
| 136 | 4-I-2-Me-Ph | CH(n-C$_3$H$_7$)$_2$ | H |
| 137 | 2-I-4-i-Pr-Ph | CH(n-C$_3$H$_7$)$_2$ | H |
| 138 | 2-Br-4-N(Me)$_2$-6-OMe-Ph | CH(n-C$_3$H$_7$)$_2$ | H |
| 139 | 2,4-[SMe]$_2$-Ph | CH(n-C$_3$H$_7$)$_2$ | H |
| 140 | 2,4-[S(O)Me]$_2$-Ph | CH(n-C$_3$H$_7$)$_2$ | H |
| 141 | 2,4-[S(O)$_2$Me]$_2$-Ph | CH(n-C$_3$H$_7$)$_2$ | H |
| 142 | 4-i-Pr-2-S(O)$_n$Me-Ph | CH(Et)CH$_2$—OCH$_3$ | H |
| 143 | 2-Br-4-CF$_3$-Ph | CH(Et)CH$_2$—OCH$_3$ | H |
| 144 | 2,6-(Me)$_2$-4-S(O)Me-Ph | CH(Et)CH$_2$—OCH$_3$ | H |
| 145 | 2,6-(Me)$_2$-4-S(O)$_2$Me-Ph | CH(Et)CH$_2$—OCH$_3$ | H |
| 146 | 2,6-(Me)$_2$-4-CF$_3$-Ph | CH(Et)CH$_2$—OCH$_3$ | H |
| 147 | 2,6-(Et)$_2$-4-Br-Ph | CH(Et)CH$_2$—OCH$_3$ | H |
| 148 | 2-Br-4,6-(Me)$_2$-Ph | CH(Et)CH$_2$—OCH$_3$ | H |
| 148 | (m.p. 156-157° C.) | | |
| 149 | 4-Cl-2-Me-Ph | CH(Et)CH$_2$—OCH$_3$ | H |
| 150 | 4-N(Et)$_2$-2-Me-Ph | CH(Et)CH$_2$—OCH$_3$ | H |
| 151 | 4-I-2-Me-Ph | CH(Et)CH$_2$—OCH$_3$ | H |
| 151 | (m.p. 122-123° C.) | | |
| 152 | 2-I-4-i-Pr-Ph | CH(Et)CH$_2$—OCH$_3$ | H |
| 153 | 2-Br-4-SMe-Ph | CH(Et)CH$_2$—OCH$_3$ | H |
| 154 | 2-Br-4-S(O)$_2$Me-Ph | CH(Et)CH$_2$—OCH$_3$ | H |
| 155 | 2-Br-4-NMe$_2$-Ph | CH(Et)CH$_2$—OCH$_3$ | H |
| 156 | 2-Me-4-NMe$_2$-Ph | CH(Et)CH$_2$—OCH$_3$ | H |
| 156 | (m.p. 159–162° C.) | | |
| 157 | 2,6-(Me)$_2$-4-NMe$_2$-Ph | CH(Et)CH$_2$—OCH$_3$ | H |
| 158 | 2-Br-4-OMe-Ph | CH(Et)CH$_2$—OCH$_3$ | H |
| 159 | 2-N(Me)$_2$-4-Me-Ph | CH(Et)CH$_2$—OCH$_3$ | H |
| 160 | 2-MeS-4,6-(Me)$_2$-Ph | CH(Et)CH$_2$—OCH$_3$ | H |
| 161 | 2-MeS(O)-4,6-(Me)$_2$-Ph | CH(Et)CH$_2$—OCH$_3$ | H |
| 162 | 2-MeS(O)$_2$-4,6-(Me)$_2$-Ph | CH(Et)CH$_2$—OCH$_3$ | H |
| 163 | 2-(CH$_3$CO)-4,6-(Me)$_2$-Ph | CH(Et)CH$_2$—OCH$_3$ | H |
| 164 | 2-Br-4-NMe$_2$-Ph | CH(Et)CH$_2$—OCH$_3$ | Et |
| 165 | 2-Me-4-NMe$_2$-Ph | CH(Et)CH$_2$—OCH$_3$ | Et |
| 166 | 2,6-(Me)$_2$-4-NMe$_2$-Ph | CH(Et)CH$_2$—OCH$_3$ | Et |
| 167 | 2-Br-4-OMe-Ph | CH(Et)CH$_2$—OCH$_3$ | Et |
| 168 | 2-N(Me)$_2$-4-Me-Ph | CH(Et)CH$_2$—OCH$_3$ | Et |
| 169 | 2-MeS-4,6-(Me)$_2$-Ph | CH(Et)CH$_2$—OCH$_3$ | Et |
| 170 | 2-MeS(O)-4,6-(Me)$_2$-Ph | CH(Et)CH$_2$—OCH$_3$ | Et |
| 171 | 2-MeS(O)$_2$-4,6-(Me)$_2$-Ph | CH(Et)CH$_2$—OCH$_3$ | Et |
| 172 | 2-(CH$_3$CO)-4,6-(Me)$_2$-Ph | CH(Et)CH$_2$—OCH$_3$ | Et |
| 173 | 2-Br-4-NMe$_2$-Ph | CH(CH$_2$—OCH$_3$)$_2$ | H |
| 174 | 2-Me-4-NMe$_2$-Ph | CH(CH$_2$—OCH$_3$)$_2$ | H |
| 175 | 2,6-(Me)$_2$-4-NMe$_2$-Ph | CH(CH$_2$—OCH$_3$)$_2$ | H |
| 176 | 2-Br-4-OMe-Ph | CH(CH$_2$—OCH$_3$)$_2$ | H |
| 177 | 2-N(Me)$_2$-4-Me-Ph | CH(CH$_2$—OCH$_3$)$_2$ | H |
| 178 | 2-MeS-4,6-(Me)$_2$-Ph | CH(CH$_2$—OCH$_3$)$_2$ | H |
| 179 | 2-MeS(O)-4,6-(Me)$_2$-Ph | CH(CH$_2$—OCH$_3$)$_2$ | H |
| 180 | 2-MeS(O)$_2$-4,6-(Me)$_2$-Ph | CH(CH$_2$—OCH$_3$)$_2$ | H |
| 181 | 2-(CH$_3$CO)-4,6-(Me)$_2$-Ph | CH(CH$_2$—OCH$_3$)$_2$ | H |
| 182 | 2-Br-4-NMe$_2$-Ph | CH(CH$_2$—OCH$_3$)$_2$ | Et |
| 183 | 2-Me-4-NMe$_2$-Ph | CH(CH$_2$—OCH$_3$)$_2$ | Et |
| 184 | 2,6-(Me)$_2$-4-NMe$_2$-Ph | CH(CH$_2$—OCH$_3$)$_2$ | Et |
| 185 | 2-Br-4-OMe-Ph | CH(CH$_2$—OCH$_3$)$_2$ | Et |
| 186 | 2-N(Me)$_2$-4-Me-Ph | CH(CH$_2$—OCH$_3$)$_2$ | Et |
| 187 | 2-MeS-4,6-(Me)$_2$-Ph | CH(CH$_2$—OCH$_3$)$_2$ | Et |
| 188 | 2-MeS(O)-4,6-(Me)$_2$-Ph | CH(CH$_2$—OCH$_3$)$_2$ | Et |
| 189 | 2-MeS(O)$_2$-4,6-(Me)$_2$-Ph | CH(CH$_2$—OCH$_3$)$_2$ | Et |
| 190 | 2-(CH$_3$CO)-4,6-(Me)$_2$-Ph | CH(CH$_2$—OCH$_3$)$_2$ | Et |
| 191 | 2-Br-4-NMe$_2$-Ph | CH(CH$_2$—CH$_2$—CH$_3$)$_2$ | H |
| 192 | 2-Me-4-NMe$_2$-Ph | CH(CH$_2$—CH$_2$—CH$_3$)$_2$ | H |
| 193 | 2,6-(Me)$_2$-4-NMe$_2$-Ph | CH(CH$_2$—CH$_2$—CH$_3$)$_2$ | H |
| 194 | 2-Br-4-OMe-Ph | CH(CH$_2$—CH$_2$—CH$_3$)$_2$ | H |
| 195 | 2-N(Me)$_2$-4-Me-Ph | CH(CH$_2$—CH$_2$—CH$_3$)$_2$ | H |
| 196 | 2-MeS-4,6-(Me)$_2$-Ph | CH(CH$_2$—CH$_2$—CH$_3$) | H |
| 197 | 2-MeS(O)-4,6-(Me)$_2$-Ph | CH(CH$_2$—CH$_2$—CH$_3$)$_2$ | H |
| 198 | 2-MeS(O)$_2$-4,6-(Me)$_2$-Ph | CH(CH$_2$—CH$_2$—CH$_3$)$_2$ | H |
| 199 | 2-(CH$_3$CO)-4,6-(Me)$_2$-Ph | CH(CH$_2$—CH$_2$—CH$_3$)$_2$ | H |
| 200 | 2-Br-4-NMe$_2$-Ph | CH(CH$_2$—CH$_2$—CH$_3$)$_2$ | Et |
| 201 | 2-Me-4-NMe$_2$-Ph | CH(CH$_2$—CH$_2$—CH$_3$)$_2$ | Et |
| 202 | 2,6-(Me)$_2$-4-NMe$_2$-Ph | CH(CH$_2$—CH$_2$—CH$_3$)$_2$ | Et |
| 203 | 2-Br-4-OMe-Ph | CH(CH$_2$—CH$_2$—CH$_3$)$_2$ | Et |
| 204 | 2-N(Me)$_2$-4-Me-Ph | CH(CH$_2$—CH$_2$—CH$_3$)$_2$ | Et |
| 205 | 2-MeS-4,6-(Me)$_2$-Ph | CH(CH$_2$—CH$_2$—CH$_3$) | Et |
| 206 | 2-MeS(O)-4,6-(Me)$_2$-Ph | CH(CH$_2$—CH$_2$—CH$_3$)$_2$ | Et |
| 207 | 2-MeS(O)$_2$-4,6-(Me)$_2$-Ph | CH(CH$_2$—CH$_2$—CH$_3$)$_2$ | Et |
| 208 | 2-(CH$_3$CO)-4,6-(Me)$_2$-Ph | CH(CH$_2$—CH$_2$—CH$_3$)$_2$ | Et |

EXAMPLE 209

N-[2-bromo-4-(1-methylethyl)phenyl]-2-methyl-9-(1-propylbutyl)-9H-purin-6-amine

Part A

The product of Part A (0.74 g) from Example 21 was treated with triethyl orthoformate (7.68 g) and con. H$_2$SO$_4$ (3 drops) and heated to 100° C. for 4 h. The excess triethyl orthoformate was removed in vacuum, and the residue was purified by flash column chromatography to yield 6-chloro-2-methyl-9-(1-propylbutyl)-9H-purine as a colorless liquid (0.32 g).

Part B

The product of Part A from above was combined with 2-bromo-4-isopropylaniline in a manner similar to Part C of Example 21 to afford the title compound as a brown oil. Elemental analysis for $C_{22}H_{30}BrN_5$: Theory C, 59.46; H, 6.80; N, 15.76. Found: C, 59.56; H, 6.83; N, 15.67.

EXAMPLE 210

(+/−)-N-[2-bromo-4-(1-methylethyl)phenyl]-9-(1-ethylpentyl)-2-methyl-9H-purin-6-amine Part A The product of Part D from Example 1 was treated with 3-aminoheptane in a manner similar to Part A of Example 21, to yield 5-amino-4-chloro-6-(3-heptyl)amino-2-methylpyrimidine as a white crystalline solid (mp 116–117° C.). Elemental analysis for $C_{12}H_{21}ClN_4$: Theory C, 56.13; H, 8.24; N, 21.82. Found: C, 56.16; H, 8.26; N, 21.82.

Part B

The product of Part A from above was treated with triethyl orthoformate in a manner similar to Part A of Example 209 to yield 6-chloro-9-(1-ethylpentyl)-2-methyl-9H-purine as a pale yellow liquid.

Part C

The product of Part B from above was combined with 2-bromo-4-isopropylaniline in a manner similar to Part C of Example 21 to afford the title compound as a colorless oil. Elemental analysis for $C_{22}H_{30}BrN_5$: Theory C, 59.46; H, 6.80; N, 15.76. Found: C, 59.30; H, 6.82; N, 15.50.

EXAMPLE 211

(+/−)-N-[2-bromo-4-(trifluromethyl)phenyl]-9-[1-(methoxymethyl)propyl]-2-methyl-9H-purin-6-amine Part A The product of Part A from Example 27 was treated with triethyl orthoformate in a manner similar to Part A of Example 209 to yield 6-chloro-9-[1-(methoxymethyl)propyl]-2-methyl-9H-purine as a white crystalline solid (mp 105–106° C.). Elemental analysis for $C_{11}H_{15}ClN_4O$: Theory C, 51.87; H, 5.95; N, 22.00. Found: C, 51.85; H, 5.81; N, 21.96.

Part B

The product of Part A from above was combined with 2-bromo-4-trifluromethylaniline in a manner similar to Part C of Example 21 to afford the title compound as a off-white solid (mp 123–124° C.). Elemental analysis for $C_{18}H_{19}BrF_3N_5O$: Theory C, 47.18; H, 4.19; N, 15.28. Found: C, 47.28; H, 3.97; N, 15.50.

The compounds of Examples 212–217 can be made by methods exemplified in Examples 209–211.

TABLE 2

9H-imidazo[4,5-d]pyrimidines:

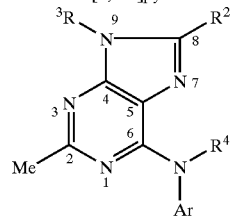

| Ex. No. | Ar | $R^2$ | $R^3$ | $R^4$ |
|---|---|---|---|---|
| 212 | 2-Br-4-i-Pr-Ph | Me | $CH(n-C_3H_7)_2$ | H |
| 213 | 2,4,6-$(Me)_3$-Ph | Me | $CH(n-C_3H_7)_2$ | H |
| 214 | 4-Br-2,6-$(Me)_2$-Ph | Me | $CH(n-C_3H_7)_2$ | H |
| 215 | 2-Br-4-i-Pr-Ph | Me | $CH(Et)CH_2OCH_3$ | H |
| 216 | 2,4,6-$(Me)_3$-Ph | Me | $CH(Et)CH_2OCH_3$ | H |
| 217 | 4-Br-2,6-$(Me)_2$-Ph | Me | $CH(Et)CH_2OCH_3$ | H |

EXAMPLE 218

N-[2-bromo-4-(1-methylethyl)phenyl]-N-ethyl-5-methyl-[1,2,3]thiadiazolo[5,4-d]pyrimidin-7-amine Part A The product of Part E (1.1 g) from Example 1 was dissolved in ethanol (15 mL) and added thiourea (0.27 g). The reaction mixture was refluxed for 1 h, removed the solvent in vacuum, partitioned between $CH_2Cl_2$ and water, washed with brine, dried and stripped down to a residue. The residue was purified by flash column chromatography ($CH_2Cl_2$) to furnish the title compound as a white crystalline solid (1.01 g, mp 81–82° C.). Elemental analysis for $C_{14}H_{14}BrN_5S$: Theory C, 46.16; H, 3.87; N, 19.23; S, 8.80. Found: C, 46.15; H, 3.85; N, 19.09; S, 8.60.

Part B

Using the procedure for Example 2, the product of Part A was alkylated to afford the title compound as a pale yellow oil. Elemental analysis for $C_{16}H_{18}BrN_5S$: Theory C, 48.98; H, 4.62; N, 17.85. Found: C, 49.23; H, 4.71; N, 17.72.

The compounds of Examples 219 and 220 can be made by the method of Example 218.

TABLE 3

[1,2,3]-Thiadiazolo[5,4-d]pyrimidines:

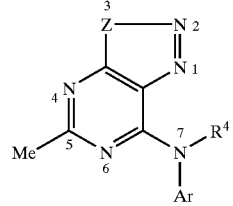

| Ex. No. | Ar | Z | $R^4$ |
|---|---|---|---|
| 219 | 2-Br-4-i-Pr-Ph | S | $n-C_3H_7$ |
| 220 | 2-Br-4-i-Pr-Ph | S | $CH_2-CH=CH_2$ |

EXAMPLE 221

N-[2-bromo-4-(1-methylethyl)phenyl]-1-(1-ethylpropyl)-6-methyl-1H-1,2,3-triazolo[4,5-c]pyridin-4-amine Part A 2,4-Dihydroxy-6-methyl-3-nitropyridine was added to phosphorous oxychloride in a manner similar to Part B of Example 1 to afford 2,4-dichloro-3-nitro-6-methylpyridine as a pale yellow solid (mp 69–70° C.).

Part B

The product of Part A (10.35 g) from above was dissolved in ethanol (100 mL) and then added triethylamine (5.05 g) followed by 3-aminopentane at room temperature under nitrogen atmosphere. The reaction mixture was stirred at room temperature for 4 days, ethanol was removed in vacuum, the residue was partitioned between ethyl acetate (150 mL) and water (150 mL). The organic layer was washed with brine, dried, stripped down to a residue and purified by flash column chromatography to furnish 2-chloro-6-methyl-3-nitro-4-(3-pentyl)aminopyridine as a pale yellow solid (2.8 g; 84–85° C.). Elemental analysis for $C_{11}H_{16}ClN_3O_2$: Theory C, 51.27; H, 6.27; N, 16.30. Found: C, 51.28; H, 6.09; N, 16.07.

Part C

The product of Part B from above was reduced in a manner similar to Part C of Example 1 to afford 3-amino-2-chloro-6-methyl-4-(3-pentyl)aminopyridine as a cream colored solid (mp 165–166° C.). Elemental analysis for $C_{11}H_{18}ClN_3$: Theory C, 58.01; H, 7.98; N, 18.45. Found: C, 57.86; H, 7.83; N, 18.44.

Part D

The product of Part C from above was cyclized in a manner similar to Part E of Example 1 to afford 4-chloro-1-(1-ethylpropyl)-6-methyl-1H-1,2,3-triazolo[4,5-c]pyridine as a light pink solid (mp 78–79° C.).

Part E

The product of Part D from above was combined with 2-bromo-4-isopropylaniline in a manner similar to Part C in Example 21, to yield the title compound as a cream colored solid (mp 144–145° C.). Elemental analysis for $C_{20}H_{26}BrN_5$: Theory C, 57.69; H, 6.29; N, 16.82. Found: C, 57.82; H, 6.29; N, 16.90.

EXAMPLE 222

N-(2-bromo-4,6-dimethoxyphenyl)-1-(1-ethylpropyl)-6-methyl-1H-1,2,3-triazolo[4,5-c]pyridin-4-amine The product of Part D from Example 221 was combined with 2-bromo-4,6-dimethoxyaniline in a manner similar to Part C in Example 21, to yield the title compound as a off-white solid (mp 166–167° C.). Elemental analysis for $C_{19}H_{24}BrN_5O_2$: Theory C, 52.54; H, 5.58; N, 16.12. Found: C, 52.63; H, 5.53; N, 16.16.

EXAMPLE 223

N-(2-chloro-4,6-dimethoxyphenyl)-1-(1-ethylpropyl)-6-methyl-1H-1,2,3-triazolo[4,5-c]pyridin-4-amine The product of Part D from Example 221 was combined with 2-chloro-4,6-dimethoxyaniline in a manner similar to Part C in Example 21, to yield the title compound as an off-white solid (mp 168–169° C.).

EXAMPLE 224

N-(2-bromo-4,6-dimethoxyphenyl)-6-methyl-1-(1-propylbutyl)-1H-1,2,3-triazolo[4,5-c]pyridin-4-amine Part A The product of Part A from Example 221, was treated with 4-aminoheptane in the same manner as outlined in Part B of Example 221 to furnish 2-chloro-4-(4-heptyl)amino-6-methyl-3-nitropyridine as an yellow oil. Elemental analysis for $C_{13}H_{20}ClN_3O_2$: Theory C, 54.64; H, 7.05; N, 14.70. Found: C, 54.93; H, 7.03; N, 14.62.

Part B

The product of Part A from above was reduced in a manner similar to Part C of Example 1 to afford 3-amino-2-chloro-4-(4-heptyl)amino-6-methylpyridine as a cream colored solid (mp 139–140° C.).

Part C

The product of Part B from above was cyclized in a manner similar to Part E of Example 1 to afford 4-chloro-6-methyl-1-(1-propylbutyl)-1H-1,2,3-triazolo[4,5-c]pyridine as an orange yellow solid (mp 90–91° C.).

Part D

The product of Part C from above was combined with 2-bromo-4,6-dimethoxyaniline in a manner similar to Part C in Example 21, to yield the title compound as a brick red colored solid (mp 140–141° C.). Elemental analysis for $C_{21}H_{28}BrN_5O_2$: Theory C, 54.55; H, 6.10; N, 15.15. Found: C, 54.83; H, 5.95; N, 15.11.

EXAMPLE 225

N-(2-chloro-4,6-dimethoxyphenyl)-6-methyl-1-(1-propylbutyl)-1H-1,2,3-triazolo[4,5-c]pyridin-4-amine The product of Part C from Example 224 was combined with 2-chloro-4,6-dimethoxyaniline in a manner similar to Part C in Example 21, to yield the title compound as a brick red colored solid (mp 157–158° C.). Elemental analysis for $C_{21}H_{28}ClN_5O_2$: Theory C, 60.35; H, 6.75; N, 16.76. Found: C, 60.43; H, 6.74; N, 16.99.

EXAMPLE 226

(+/−)-N-[2-bromo-4-(1-methylethyl)phenyl]-1-(1-ethylpentyl)-6-methyl-1H-1,2,3-triazolo[4,5-c]pyridin-4-amine Part A The product of Part A from Example 221, was treated with 3-aminoheptane in the same manner as outlined in Part B of Example 221 to furnish 2-chloro-4-(3-heptyl)amino-6-methyl-3-nitropyridine as an yellow solid (mp 48–49° C.). Elemental analysis for $C_{13}H_{20}ClN_3O_2$: Theory C, 54.64; H, 7.05; N, 14.70. Found: C, 54.79; H, 6.95; N, 14.67.

Part B

The product of Part A from above was reduced in a manner similar to Part C of Example 1 to afford 3-amino-2-chloro-4-(3-heptyl)amino-6-methylpyridine as a cream colored solid (mp 139–140° C.).

Part C

The product of Part B from above was cyclized in a manner similar to Part E of Example 1 to afford 4-chloro-1-(1-ethylpropyl)-6-methyl-1H-1,2,3-triazolo[4,5-c]pyridine as a colored liquid. Elemental analysis for $C_{13}H_{19}ClN_4$: Theory C, 58.53; H, 7.19; N, 21.00. Found: C, 58.69; H, 7.06; N, 20.76.

Part D

The product of Part C from above was combined with 2-bromo-4-isopropylaniline in a manner similar to Part C in Example 21, to yield the title compound as a light pink colored solid (mp 73–74° C.). Elemental analysis for $C_{22}H_{30}BrN_5$: Theory C, 59.46; H, 6.80; N, 15.76, Found: C, 59.56; H, 6.70; N, 15.70.

EXAMPLE 227

(+/−)-N-(2-bromo-4,6-dimethoxyphenyl)-1-(1-ethylpentyl)-6-methyl-1H-1,2,3-triazolo[4,5-c]pyridin-4-amine The product of Part C from Example 226 was combined with 2-bromo-4,6-dimethoxyaniline in a manner similar to Part C in Example 21, to yield the title compound as a brick red colored solid (mp 127–128° C.). Elemental analysis for $C_{21}H_{28}BrN_5O_2$: Theory C, 54.55; H, 6.10; N, 15.15. Found: C, 54.78; H, 5.84; N, 14.92.

EXAMPLE 228

(+/−)-N-(2-chloro-4,6-dimethoxyphenyl)-1-(1-ethylpentyl)-6-methyl-1H-1,2,3-triazolo[4,5-c]pyridin-4-amine The product of Part C from Example 226 was combined with 2-chloro-4,6-dimethoxyaniline in a manner similar to Part C in Example 21, to yield the title compound as a brick red colored solid (mp 155–156° C.). Elemental analysis for $C_{21}H_{28}ClN_5O_2$: Theory C, 60.35; H, 6.75; N, 16.76. Found: C, 60.36; H, 6.65; N, 16.84.

EXAMPLE 229

N-[2-bromo-4-(1-methylethyl)phenyl]-6-methyl-1-(1-propylbutyl)-1H-1,2,3-triazolo[4,5-c]pyridin-4-amine Part A 4-Chloro-6-methyl-3-nitropyridone 4-Hydroxy-6-methyl-3-nitropyridone (4.0 g, 23, 52 mmol) was treated with cyclohexylamine (2.8 mL, 24.46 mmol) in MeOH (50 mL) until all dissolved. The MeOH was stripped in vacuo and the resulting salt was dried and treated with $POCl_3$ (30 mL) at 25° C. for 30 h. The reaction was then poured into ice/water (400 mL) and extracted with EtOAc (2×200 mL). The combined EtOAc extracts were washed with water (100 mL), 1 N NaOH (20 mL), water (100 mL) and brine, dried ($MgSO_4$) and stripped in vacuo. The residue was washed with 20% EtOAc/hexanes (2×30 mL) to give the product (2.9 g).

Part B

6-Methyl-3-nitro-4-(1-propylbutylamino)pyridone

4-Chloro-6-methyl-3-nitropyridone (2.9 g, 15.40 mmol) was treated with 1-propylbutylamine (4 mL, 26.8 mmol) in $CH_3CN$ (30 mL) at 25° C. for 64 h and at reflux for 2 h. The reaction mixture was partitioned between EtOAc (200 mL) and water (50 mL). The EtOAc was washed with water (2×50 mL), brine, dried ($MgSO_4$) and stripped in vacuo. The residue was washed with 20% EtOAc/hexanes (2×20 mL) to give the product (3.7 g).

Part C

2-Chloro-6-methyl-3-nitro-N-(1-propyl-butyl)pyridin-4-amine

6-Methyl-3-nitro-4-(1-propylbutylamino)pyridone (3.7 g, 13.84 mmol), was treated with $POCl_3$ (14 mL) at 25° C. for 20 h. Then it was poured into ice/water (200 mL) and extracted with EtOAc (300 mL). The EtOAc was washed with water, brine, dried ($MgSO_4$) and stripped in vacuo. The residue was chromatographed on silica gel (20% EtOAc/hexanes eluting solvent) to give the product (3.3 g).

Part D

N-[2-Bromo-4-(1-methylethyl)phenyl]-6-methyl-3-nitro-N-(1-propylbutyl)pyridin-2,4-diamine 2-Chloro-6-methyl-3-nitro-N-(1-propylbuty)pyridin-4-amine (0.5 g, 1.75 mmol) and 2-bromo-4-isopropylaniline (0.74 g, 3.5 mmol) were heated at 140° C. for 4.5 h. After cooling it was dissolved in $CH_2Cl_2$ and filtered through a short column of silica gel. The filtrate was concentrated and chromatographed on silica gel (5% EtOAc/hexanes eluting solvent) to give the product (0.7 g).

Part E

N-[2-Bromo-4-(1-methylethyl)phenyl]-6-methyl-N-(1-propylbuty)pyridine-2,3,4-triamine N-[2-Bromo-4-(1-methylethyl)phenyl]-6-methyl-3-nitro-N-(1-propyl-butyl)pyridin-2,4-diamine (0.7 g, 1.51 mmol), was suspended between dioxane (30 mL) and water (30 mL) containing conc.$NH_4OH$ (1.2 mL). To that $Na_2S_2O_4$ was added (2.1 g, 12.06 mmol) and the mixture was stirred at 25° C. for 2h. Then an additional 1 g $Na_2S_2O_4$ was added followd by 10 mL dioxane and 10 mL water. After stirring for 1 h at 25° C. the mixture was patritioned between EtOAc (120 mL) and water (20 mL). The EtOAc was washed with water (100 mL), brine, dried ($MgSO_4$) and stripped in vacuo. The residue was chromatographed on silica gel (20% EtOAc/hexanes eluting solvent) to give the product (0.5 g).

Part F

N-[2-bromo-4-(1-methylethyl)phenyl]-6-methyl-1-(1-propylbutyl)-1H-1,2,3-triazolo[4,5-c]pyridin-4-amine N-[2-Bromo-4-(1-methylethyl)phenyl]-6-methyl-N-(1-propylbutyl)pyridine-2,3,4-triamine (0.5 g, 1.15 mmol), dissolved in $CH_2Cl_2$ (6 mL) and 50% AcOH (4 mL) was treated with $NaNO_2$ (0.0846 g, 1.22 mmol) at 25° C. for 16 h. The mixture was patritioned between EtOAc (100 mL) and water (20 mL) The EtOAc was washed with water (20 mL), brine, dried and stripped in vacuo. The residue was chromatographed on silica gel (20% EtOAc/hexanes eluting solvent) to give the product (0.2 g). Anal. Calcd. for $C_{22}H_{30}BrN_5$; C, 59.46; H, 6.80; N, 15.76; Br, 17.98. Found: C, 59.76; H, 6.83; N, 15.67; Br, 18.17.

EXAMPLE 231

N-[4-(1-methylethyl)-2-sulfonylmethylphenyl]-6-methyl-1-(1-propylbutyl)-1H-1,2,3-triazolo[4,5-c]pyridin-4-amine N-[4-(1-methylethyl)-2-thiomethylphenyl]-6-methyl-1-(1-propylbutyl)-1H-1,2,3-triazolo[4,5-c]pyridin-4-amine (0.15 g, 1 equiv.) (Example 231), synthesized under the same general conditions of Example 229, was dissolved in methanol (3 mL) and water (2 mL) was added, followed by $NaIO_4$ (0.114 g, 1.5 equiv.). The mixture was stirred at 25° C. for 20 h and then was extracted with EtOAc (80 mL). The EtOAc was washed with water, brine, dried and stripped in vacuo. The residue was dissolved in $CH_2Cl_2$ and a solution of KMnO₄ (0.15 g, 2.5 equiv.) in water (2 mL) was added, followed by benzyltriethylammonium chloride (0.15 g, 1.5 equiv.). The mixture was stirred at 25° C. for 20 h and then extracted with EtOAc (80 mL) and the EtOAc was washed with water, brine, dried and stripped in vecuo. The residue was chromatographed on silica gel (10% EtOAc/hexanes eluting solvent) to give the product (0.2 g). Anal. Calcd. for $C_{23}H_{33}BrN_5O_2S$: C, 62.27; H, 7.51; N, 15.79; S, 7.24. Found: C, 62.62; H, 7.38; N, 15.58 S, 7.44.

EXAMPLE 232

N-[4-(4-acetyl-2-bromophenyl]-6-methyl-1-(1-propyl-butyl)-1H-1,2,3-triazolo[4,5-c]pyridin-4-amine Part A Used the standard procedure for the coupling of the nitropyridine (0.8 g, 2.9 mmoles) and 2-Bromo-4-iodoaniline (1.7 g, 5.7 mmoles). Preabsorbed the crude material on 12 g. of silica gel before chromatographing on silica gel (5% EtOAc/hexane eluen) to give an orange solid, 1.47 g. of the desired product.

Part B

To the coupled 2-Bromo-4-iodoanilinonitropyridine (0.60 g, 1.1 mmoles) in a dried flask, under nitrogen, was added Bis(triphenylphosphine)palladium(II)chloride (18 mg, 0.026 mmoles) and anhydrous toluene (5 mL). Added 1-Ethoxyvinyltributyltin (0.46 ml, 1.36 mmoles) and stirred at reflux temperature for 1½ hours. Dissolved into ethyl acetate then filtered off the insolubles through celite. Washed the solids 2× with ethyl acetate. Concentrated in-vacuo the filtrates to near dryness. Stirred the residue with 70 ml 1M hydrochloric acid for ½ hour. Added some ethyl acetate and separated the layers., extracted the water layer with 2×20 ml ethyl acetate. Concentrated the combined organics to near dryness. Stirred the residue in a saturated potassium fluoride (20 ml) for ½ hour. Separated the layers. Extracted the water layer with 2×20 ml ethyl acetate. Washed the combined extracts with 10 ml water and 20 ml brine. Chromatographed the crude material on silica gel to give a solid, 0.37 g (73%) of the desired product.

Part C

Using the product obtained from Part B (0.70 g, 1.5 mmoles), 10 ml tetrahydrofuran, 10 ml water, 0.70 ml ammonium hydroxide solution (38–40%) and sodium dithionite (2.1 g, 12 mmoles) followed the standard procedure to reduce the nitroanilinopyridine. obtained the crude solid, 0.65 g, which was of sufficient purity for further reaction.

Part D

Followed the standard procedure to cyclize the product obtained in Part C (0.63 g, 1.45 mmoles), using 10 ml methylene chloride, 10 ml acetic acid/water (50%), and sodium nitrite (0.18 g, 2.59 mmoles) in 1 ml water. Chromatographed on silica gel (10% ethyl acetate/hexane) to give a white solid, 0.31 g, (48%) of desired product, mp 165–166° C. Anal. Calcd. for $C_{21}H_{26}BrN_5O$: C, 56.76; H, 5.91; N, 15.76; Br, 17.98. Found: C, 56.75; H, 5.76; N, 15.71; Br, 17.72. Obtained the isomer of the desired product, a white solid, 90 mg, mp 133–136° C. Anal. Calcd: Found: C, 57.11; H, 5.82; N, 15.69; Br, 18.23.

The rest of the examples shown in Table 4 were prepared by following the general procedure outlined in Example 229.

TABLE 4

1H-1,2,3-triazolo[4,5-c]pyridines:

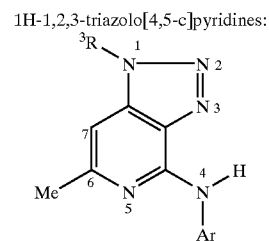

| Ex. No. | R³ | Ar | Mp ° C. |
|---|---|---|---|
| 233 | CH(Et)CH₂—OCH₃ | 2-Br-4-i-Pr-Ph | 121–123 |
| 234 | CH(Et)CH₂—OCH₃ | 4-i-Pr-2-SMe-Ph | 97–100 |
| 235 | CH(i-C₃H₇)₂ | 2-Br-4-(iC₃H₇)Ph | 96—96 |
| 236 | CH(i-C₃H₇)₂ | 4-(i-C₃H₇)-2-SMe-Ph | |
| 237 | CH(C₂H₅)₂ | 4-(i-C₃H₇)-2-SMe-Ph | |
| 238 | CH(n-C₃H₇)₂ | 2-Br-4-I-Ph | 161–164 |
| 239 | CH(n-C₃H₇)₂ | 2,4-(Br)₂-Ph | 125–127 |
| 240 | CH(Et)CH₂—OCH₃ | 2,4,6-Me₃-Ph | |
| 241 | i-Pr | 2-Br-4-i-Pr-Ph | |
| 242 | i-Pr | 4-i-Pr-2-SMe-Ph | |
| 243 | c-Pr | 2-Br-4-i-Pr-Ph | |
| 244 | c-Pr | 4-i-Pr-2-SMe-Ph | |
| 245 | i-Pr | 2,4-(Br)₂-Ph | |
| 246 | c-Pr | 2,4-(Br)₂-Ph | |
| 247 | CH(Et)CH₂—OCH₃ | 2,4-(Br)₂-Ph | |
| 248 | CH(Et)₂ | 2,4-(Br)₂-Ph | |
| 249 | CH(Et)CH₂—OCH₃ | 2-COMe-4-Br-Ph | |
| 250 | CH(Et)₂ | 4-COMe-2-Br-Ph | |
| 251 | CH(Et)₂ | 2-Br-4-SO₂Me-Ph | |
| 252 | CH(Et)₂ | 2,4,6-Me₃-Ph | |
| 253 | CH(CH₂CN)₂ | 2-Br-4-(i-C₃H₇)Ph | |
| 254 | CH(Et)CH₂CN | 2-Br-4-(i-C₃H₇)Ph | |
| 255 | CH(Et)CH₂CONMe₂ | 2-Br-4-(i-C₃H₇)Ph | |
| 256 | CH(CH₂CN)₂ | 2-Br-4,6-(OMe)₂Ph | |
| 257 | CH(Et)CH₂CN | 2-Br-4,6-(OMe)₂Ph | |
| 258 | CH(Et)CH₂CONMe₂ | 2-Br-4,6-(OMe)₂Ph | |

EXAMPLE 259

N-(2-chloro-4,6-dimethylphenyl)-1-[1-methoxymethyl-(2-methoxyethyl]-6-methyl-1H-1,2,3-triazolo[4,5-c]pyridin-4-amine Part A Serinol (24 g) was added to a solution of trityl chloride (65 g) and triethylamine (51.0 g) in 600 mL of dry DMF. After stirring at room temperature for 48 h, the reaction was poured into water and extracted several times with diethyl ether. The combined organic layers were dried over anhydrous magnesium sulfate and concentrated to dryness to afford N-triphenylmethylserinol (71.0 g).

Part B

Methyl iodide (90 mL) was added to a suspension of N-triphenylmethylserinol (37.0 g) and powdered sodium hydroxide (45.0 g) in 400 mL of dry DMSO. After stirring at room temperature for 24–36 h, the reaction was added to water (800 mL) and extracted with diethyl ether (3×500 mL). The combined organic layers was washed with water (4×250 mL), dried over anhydrous magnesium sulfate and concentrated to afford 1,3-dimethoxy-2-triphenylmethylaminopropane (36.0 g) as a thick viscous oil.

Part C

To a solution of the product of Part B (36.0 g) in methanol (400 mL) was added 1 M HCl in ether (350 mL). After stirring overnight, the reaction was poured over water (800 mL) extracted with hexane (3×250 mL). The methanol/water layer was concentrated to dryness to afford 1,3-dimethoxy-2-aminopropane hydrochloride (14.0 g) as a waxy solid.

Part D

4-Chloro-6-methyl-3-nitro-2-pyridone

4-Hydroxy-6-methyl-3-nitro-2-pyridone (50.0 g) was treated with cyclohexylamine (40 g) in MeOH (300 mL) and heated until all dissolved. The MeOH was stripped in vacuum and the resulting salt was dried and treated with POlC₃ (360 mL) at 25° C. for 48 h. The excess POCl₃ was removed under vacuum and the residue was poured into ice/water (1000 mL) and extracted with EtOAc (4×250 mL). The combined EtOAc extracts were washed with aq. NaHCO₃, brine (3*100 mL), dried (MgSO₄) and stripped in vacuum. The residue was washed with 20% EtOAc/hexanes (2×100 mL) to afford the product as a yellow solid (41.3 g; mp 225° C.).

Part E

4-[1-methoxymethyl-(2-methoxyethyl]amino-6-methyl-3-nitro-2-pyridone

4-Chloro-6-methyl-3-nitro-2-pyridone (12.12 g; from part D) was treated with 1,3-dimethoxy-2-aminopropane hydrochloride (10.0 g; from part C) in CH₃CN (200 mL) and diisopropylethylamine (20.0 g) at 25° C. for 24 h and at reflux for 3 h. The reaction mixture was partitioned between EtOAc (200 mL) and water (50 mL). The EtOAc was washed with water (2×50 mL), brine, dried (MgSO₄) and stripped in vacuum to give the product as a yellow solid (9.4 g; m.p.172–173° C.).

Part F

2-Chloro-N-[1-methoxymethyl-(2-methoxyethyl]-6-methyl-3-nitro-pyridin-4-amine

4-[1-methoxymethyl-(2-methoxyethyl]amino-6-methyl-3-nitro-2-pyridone (9.4 g from part E), was treated with POCl₃ (55 mL) at 25° C. for 24 h. The excess POCl₃ was removed under vacuum, and the residue was poured into ice/water (200 mL) and extracted with CH₂Cl₂ (3×150 mL). The combined CH₂Cl₂ extract was washed with water, dried (MgSO₄) and stripped in vacuum to give the product as a yellow solid (9.0 g; m.p. 85–87° C.).

Part G

2-Chloro-4-l[1-methoxymethyl-(2-methoxyethyl]amino-6-methylpyridin-3-amine

The product of Part F (9.0 g) was added to acetic acid (80 mL) and methanol (400 mL). To this mixture was added iron powder (9.0 g) in portions, stirred for 5 h at 60–65° C., cooled to room temperature, and filtered through celite. The filtrate was stripped to a brown solid, which was extracted with ethyl acetate (2×150 mL), washed with NaHCO₃ (100 mL), and brine (100 mL). The organic layer was dried over anhydrous magnesium sulfate, filtered and stripped down to yield the product as a pale yellow solid (5.6 g; m.p. 100° C.).

Part H

4-Chloro-1-[1-methoxymethyl-(2-methoxyethyl]-6-methyl-1H-1,2,3-triazolo[4,5-c]pyridine The product of Part G (5.4 g) was dissolved in dichloromethane (100 mL) and 50% aqueous acetic acid (100 mL). To this stirred mixture was added sodium nitrite (1.7 g) in water (10 mL) dropwise at room temperature. After completion of addition, the reaction was stirred for an additional 15 mins. The organic layer was separated, washed with water, dried with anhydrous magnesium sulfate, and stripped down to a residue. The residue was purified by flash column chromatography (CH₂Cl₂) to afford the product as a pale yellow solid (5.4 g; m.p. 49–50° C.).

Part I

N-(2-chloro-4,6-dimethylphenyl)-1-[1-methoxymethyl-(2-methoxyethyl]6-methyl-1H-1,2,3-triazolo[4,5-c]pyridin-4-amine The product of Part H (2.0 g) from above was combined with 2-chloro-4,6-dimethylaniline (1.4 g) in the presence of p-toluenesulfonic acid (1.7 g) in toluene (25.0 mL) at 110° C. for 4 h. The reaction mixture was partitioned between EtOAC (50 mL) and aq. NaHCO₃ (50 mL), washed the organic layer with brine, dried and stripped in vacuum to a residue. The residue was purified by flash column chromatography (1:100::MeOH: CH₂Cl₂) to afford the title compound as white solid (1.7 g; mp 83–84° C.) after crystallization from ether/pentane. Elemental analysis for C₁₉H₂₄ClN₅O₂: Theory C, 58.53; H, 6.20; N, 17.96; Cl, 9.09. Found: C, 58.69; H, 6.32; N, 17.97; Cl, 9.18.

Part J

Mesylate salt of N-(2-chloro-4,6-dimethylphenyl)-1-[1-methoxymethyl-(2-methoxyethyl]-6-methyl-1H-1,2,3-triazolo[4,5-c]pyridin-4-amine The product of Part I (850 mg) was dissolved in dichloromethane (5.0 mL) and then added methanesulfonic acid (250 mg). The solvent was removed and the residue was crystallized from 2-propanol (2.5 mL) to afford the mesylate salt (920 mg; m.p. 179–180° C.) as a white crystalline solid. Elemental analysis for C₂₀H₂₈ClN₅O₅S: Theory C, 49.43; H, 5.82; N, 14.41. Found: C, 49.42; H, 5.79; N, 14.37.

The compounds listed in Tables 5 and 6 were prepared by the methods exemplified in Examples 1–53 and 526.

TABLE 5

3H-1,2,3-triazolo[4,5-d]pyrimidines:

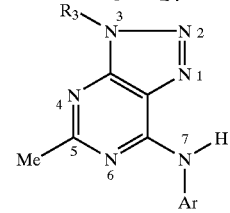

| Ex. No. | Ar | R³ | m.p. (° C.) |
|---|---|---|---|
| 260 | 2-Br-2,6-(Me)₂—Ph | CH(Et)₂ | 134–135 |
| 261 | 2-Cl-2,6-(Me)₂—Ph | CH(Et)₂ | 133–134 |
| 262 | 4-Br-2-Cl-6-Me—Ph | CH(Et)₂ | 132–133 |
| 263 | 2,4-(Cl)₂-6-Me—Ph | CH(Et)₂ | 132–133 |
| 264 | 2,4-(Br)₂-6-F—Ph | CH(Et)₂ | 186–188 |
| 265 | 4-Br-2-Me—Ph | CH(Et)₂ | 125–127 |
| 266 | 4-NMe₂-2-Me—Ph | CH(Et)₂ | 136–137 |
| 267 | 4-Cl-2-Me—Ph | CH(Et)₂ | 116–118 |
| 268 | 4-I-2-Me—Ph | CH(Et)₂ | 139–140 |
| 269 | 4-NMe₂-2,6-(Me)₂—Ph | CH(Et)₂ | 160–161 |
| 270 | 2-Cl-4-Me—Ph | CH(Et)₂ | 100–101 |
| 271 | 2-Br-4-OMe—Ph | CH(Et)₂ | 146–147 |
| 272 | 2-Br-4-NMe₂—Ph | CH(Et)₂ | 166–167 |
| 273 | 2-Me-4-CH₂OMe—Ph | CH(Et)₂ | oil |
| 274 | 2-CN-4-Me—Ph | CH(Et)₂ | 221–223 |
| 275 | 4-CN-2-Me—Ph | CH(Et)₂ | 216–218 |
| 276 | 2,4,6-Me₃—Ph | CH(nPr)Me | 140.5–142 |
| 277 | 4-Br-2,6-Me₂—Ph | CH(nPr)Me | 131–133 |
| 278 | 2-Cl-4, 6-Me₂—Ph | CH(nPr)Me | amorph. |
| 279 | 2-Cl-4,6-(OMe)₂—Ph | CH(nPr)Me | 144–145 |
| 280 | 2,4,5-Me₃—Ph | CH(nPr)Me | 110–112 |
| 281 | 4-Cl-2-Me—Ph | CH(nPr)Me | 99–101 |
| 282 | 4-Br-2-Me—Ph | CH(nPr)Me | 83–84.5 |
| 283 | 4-I-2-Me—Ph | CH(nPr)Me | 104–105 |
| 284 | 2,4-Me₂—Ph | CH(nPr)Me | 74.5–76.5 |
| 285 | 2-Br-4-CH(Me)₂—Ph | CH(nPr)Me | amorph. |
| 286 | 2-Br-4-Cl—Ph | CH(nPr)Me | 104–108 |
| 287 | 2-Br-4-NMe₂—Ph | CH(nPr)Me | Amorph. |
| 288 | 4-NMe₂-2-Me—Ph | CH(nPr)Me | amorph. |
| 289 | 2,4-(Me)₂—Ph | CH(Et)n-Pr | 88–89 |
| 290 | 4-OMe-2-Me—Ph | CH(Et)n-Pr | 111–112 |
| 291 | 2,4-(SMe)₂—Ph | CH(Et)n-Pr | 65–66 |
| 292 | 2-Br-4-CF₃—Ph | CH(Et)n-Pr | 91–92 |
| 293 | 4-Ac-2-Br—Ph | CH(Et)n-Pr | 138–139 |

TABLE 5-continued 3H-1,2,3-triazolo[4,5-d]pyrimidines:

| Ex. No. | Ar | R³ | m.p. (° C.) |
|---|---|---|---|
| 294 | 4-NMe₂-2-Me—Ph | CH(Et)n-Pr | 116.5–118 |
| 295 | 4-Cl-2-Me—Ph | CH(Et)n-Pr | amorph. |
| 296 | 4-I-2-Me—Ph | CH(Et)n-Pr | 110–111.5 |
| 297 | 2,6-Me₂-4-I—Ph | CH(Et)n-Pr | 158–160 |
| 298 | 4-Ac-2-Me—Ph | CH(Et)n-Pr | 107–110.5 |
| 299 | 2-NMe₂-4-Me—Ph | CH(Et)n-Pr | 106–107 |
| 300 | 4-NMe₂-2,6-(Me)₂—Ph | CH(Et)n-Pr | 146–148 |
| 301 | 2,4-(SMe)₂—Ph | CH(n-Pr)₂ | 105–106 |
| 302 | 4-OMe-2-Me—Ph | CH(n-Pr)₂ | 109–110 |
| 303 | 2-Br-4-N(Me)₂—Ph | CH(n-Pr)₂ | 102–103 |
| 304 | 2,4-(Me)₂—Ph | CH(n-Pr)₂ | 97–98 |
| 305 | 4-Ac-2,6-(Me)₂—Ph | CH(n-Pr)₂ | 162–164 |
| 306 | 4-Cl-2-Me—Ph | CH(n-Pr)₂ | 126–127.5 |
| 307 | 4-NMe₂-2-Me—Ph | CH(n-Pr)₂ | 129–130.5 |
| 308 | 4-I-2-Me—Ph | CH(n-Pr)₂ | 98.5–101 |
| 309 | 2-Me-4-CH₂OMe—Ph | CH(n-Pr)₂ | oil |
| 310 | 4-Br-2,6-Me₂—Ph | CH(Et)CH₂OMe | 140–141 |
| 311 | 4-Br-2,6-Me₂—Ph | CH(Et)CH₂OMe | 139–140 |
| 312 | 2-Cl-4,6-(Me)₂—Ph | CH(Et)CH₂OMe | 141–142 |
| 313 | 4-Br-2-Cl-6-Me—Ph | CH(Et)CH₂OMe | 121–122 |
| 314 | 2,4-(Cl)₂-6-Me—Ph | CH(Et)CH₂OMe | 109–110 |
| 315 | 2,4-(Br)₂-6-F—Ph | CH(Et)CH₂OMe | 147–148 |
| 316 | 2-Br-3,4,6-(Me)₃—Ph | CH(Et)CH₂OMe | 166–167 |
| 317 | 3-Br-2,4,6-(Me)₃—Ph | CH(Et)CH₂OMe | 147–148 |
| 318 | 4-Br-2,6-(F)₂—Ph | CH(Et)CH₂OMe | 148–149 |
| 319 | 2-Br-4-Cl-6-F—Ph | CH(Et)CH₂OMe | 139–140 |
| 320 | 2-Br-4,6-(F)₂—Ph | CH(Et)CH₂OMe | 124–125 |
| 321 | 4-CN-2,6-(Cl)₂—Ph | CH(Et)CH₂OMe | 180–181 |
| 322 | 2,4-(SMe)₂—Ph | CH(Et)CH₂OMe | 75–77 |
| 323 | 2-Br-4-N(Me)₂—Ph | CH(Et)CH₂OMe | 110–112 |
| 324 | 2-Cl-4-CN-6-Me—Ph | CH(Et)CH₂OMe | 145–146 |
| 325 | 2-Cl-4-CN—Ph | CH(Et)CH₂OMe | 140 |
| 326 | 2,4,5-(Me)₃—Ph | CH(Et)CH₂OMe | 108–109 |
| 327 | 2,4-(Me)₂—Ph | CH(Et)CH₂OMe | 104–105 |
| 328 | 4-Br-2,6-(Et)₂—Ph | CH(Et)CH₂OMe | 151–152 |
| 329 | 4-Br-2,6-(Cl)₂—Ph | CH(Et)CH₂OMe | 109–110 |
| 330 | 2-Br-4,6-(Cl)₂—Ph | CH(Et)CH₂OMe | 113–114 |
| 331 | 2,6-(Br)₂-4-Cl—Ph | CH(Et)CH₂OMe | 153–154 |
| 332 | 4-Br-2-Me-6-NO₂—Ph | CH(Et)CH₂OMe | 150–151 |
| 333 | 4-OMe-2-Me—Ph | CH(Et)CH₂OMe | 128–129 |
| 334 | 2,5-Cl₂-4-NMe₂—Ph | CH(Et)CH₂OMe | 84–85 |
| 335 | 2,4-Cl₂—Ph | CH(Et)CH₂OMe | 114–116 |
| 336 | 2-Br-4-Cl—Ph | CH(Et)CH₂OMe | 133.5–135 |
| 337 | 4-Cl-2-Me—Ph | CH(Et)CH₂OMe | amorph. |
| 338 | 4-I-2,6-Me₂—Ph | CH(Et)CH₂OMe | 148.5–150 |
| 339 | 4-NMe₂-2,6-(Me)₂—Ph | CH(Et)CH₂OMe | 144–146 |
| 340 | 2-Cl-4-Me—Ph | CH(Et)CH₂OMe | 88–89 |
| 341 | 2-Br-4-OMe—Ph | CH(Et)CH₂OMe | 118–120 |
| 342 | 2-Me-4-CH₂OMe—Ph | CH(Et)CH₂OMe | oil |
| 343 | 2,4,6-Me₃—Ph | CH(Et)CH₂OEt | 127–130 |
| 344 | 2-Cl-4,6-Me₂—Ph | CH(Et)CH₂OEt | 61–62 |
| 345 | 4-Br-2,6-Me₂—Ph | CH(Et)CH₂OEt | 104–107 |
| 346 | 2,4-Me₂—Ph | CH(Et)CH₂OEt | oil |
| 347 | 2-Br-4-Me—Ph | CH(Et)CH₂OEt | 100–102 |
| 348 | 2,4,6-Me₃—Ph | CH(Et)CH₂OEt | 94–96.5 |
| 349 | 2,4,6-Me₃—Ph | CH(C₃H₇)CH₂OMe | 136–138 |
| 350 | 2-Cl-4,6-Me₂—Ph | CH(C₃H₇)CH₂OMe | amorph. |
| 351 | 4-Br-2,6-Me₂—Ph | CH(C₃H₇)CH₂OMe | 139–140.5 |
| 352 | 2,4-Me₂—Ph | CH(C₃H₇)CH₂OMe | oil |
| 353 | 2-Br-4-Me—Ph | CH(C₃H₇)CH₂OMe | 100.5–102 |
| 354 | 2,4,5-Me₃—Ph | CH(C₃H₇)CH₂OMe | 122–124 |
| 355 | 2,4,6-Me₃—Ph | CH(CHMe₂)CH₂OMe | 94–96.5 |
| 356 | 2-Cl-4,6-Me₂—Ph | CH(CHMe₂)CH₂OMe | 155–156 |
| 357 | 4-Br-2,6-Me₂—Ph | CH(CHMe₂)CH₂OMe | 156–159 |
| 358 | 2,4-Me₂—Ph | CH(CHMe₂)CH₂OMe | 99–103 |
| 359 | 2-Br-4-Me—Ph | CH(CHMe₂)CH₂OMe | 93–95 |
| 360 | 2,4,5-Me₃—Ph | CH(CHMe₂)CH₂OMe | 130–131 |
| 361 | 2,4,6-Me₃—Ph | CH(sec-Bu)CH₂OMe | 168–170.5 |
| 362 | 2-Cl-4,6-Me₂—Ph | CH(sec-Bu)CH₂OMe | 136–139 |
| 363 | 4-Br-2,6-Me₂—Ph | CH(sec-Bu)CH₂OMe | 139–142 |
| 364 | 2,4-Me₂—Ph | CH(sec-Bu)CH₂OMe | 85–87 |
| 365 | 2-Br-4-Me—Ph | CH(sec-Bu)CH₂OMe | 78.5–80 |
| 366 | 2,4,5-Me₃—Ph | CH(sec-Bu)CH₂OMe | 150–153 |
| 367 | 2,4,6-Me₃—Ph | CH(isoBu)CH₂OMe | 126.6–129 |
| 368 | 2-Cl-4,6-Me₂—Ph | CH(isoBu)CH₂OMe | 103–10 |
| 369 | 4-Br-2,6-Me₂—Ph | CH(isoBu)CH₂OMe | 127.5–130 |
| 370 | 2,4-Me₂—Ph | CH(isoBu)CH₂OMe | amorph. |
| 371 | 2-Br-4-Me—Ph | CH(isoBu)CH₂OMe | 99–100.5 |
| 372 | 2,4,5-Me₃—Ph | CH(isoBu)CH₂OMe | 134–138 |
| 373 | 2-Cl-4,6-Me₂—Ph | CH(CH₂OMe)₂ | 98–99 |
| 374 | 4-Br-2,6-Me₂—Ph | CH(CH₂OMe)₂ | 115–116 |
| 375 | 4-OMe-2-Ph—Ph | CH(CH₂OMe)₂ | 55–57 |
| 376 | 3-Br-2,4,6-Me₃—Ph | CH(CH₂OMe)₂ | 151–152 |
| 377 | 4-Br-2,6-Et₂—Ph | CH(CH₂OMe)₂ | 154–155 |
| 378 | 2,4,6-(Me)₃—Ph | CH(CH₂OMe)₂ | 136–137 |
| 379 | 4-Br-2-Me—Ph | CH(CH₂OMe)₂ | 104–108 |
| 380 | 2-Br-4-Cl—Ph | CH(CH₂OMe)₂ | 123–125 |
| 381 | 2,4-Cl₂—Ph | CH(CH₂OMe)₂ | 87.5–90 |
| 382 | 4-NMe₂-2-Me—Ph | CH(CH₂OMe)₂ | 159–162 |
| 383 | 4-Cl-2-Me—Ph | CH(CH₂OMe)₂ | 100–102 |
| 384 | 4-I-2-Me—Ph | CH(CH₂OMe)₂ | 116–117.5 |
| 385 | 2,6-Me₂-4-I—Ph | CH(CH₂OMe)₂ | amorph. |
| 386 | 2-NMe₂-4-Me—Ph | CH(CH₂OMe)₂ | 100–102 |
| 387 | 2-Br-4-Me—Ph | CH(CH₂OMe)₂ | 106–108 |
| 388 | 2-Cl-4-Me—Ph | CH(CH₂OMe)₂ | 114–115 |
| 389 | 4-NMe₂-2,6-(Me)₂—Ph | CH(CH₂OMe)₂ | 71–73 |
| 390 | 2-Br-4-OMe—Ph | CH(CH₂OMe)₂ | 127–128 |
| 391 | 2-Br-4-NMe₂—Ph | CH(CH₂OMe)₂ | 139–141 |
| 392 | 2-Me-4-CH₂OMe—Ph | CH(CH₂OMe)₂ | oil |
| 393 | 2,4,6-Me₃—Ph | CH(Et)CH₂Ph | amorph. |
| 394 | 2,4,6-Me₃—Ph | 2-OMe-6-Me—Ph | 202–205 |
| 395 | 2,4,6-Me₃—Ph | CH(Et)CH₂OH | amorph. |
| 396 | 2,4,6-Me₃—Ph | CH(Me)isoBu | 126–127 |
| 397 | 2,4,6-Me₃—Ph | CH(Me)isoPr | 161–162 |
| 398 | 2,4,6-Me₃—Ph | cyclopentyl | 174–175 |
| 399 | 2,4,6-Me₃—Ph | cyclohexyl | 198–199 |
| 400 | 2,4,6-Me₃—Ph | 4-methylcyclohexyl | 178–180 |

Note: (+), (−), (R) or (S) denotes respective isomers

TABLE 6

3H-1,2,3-triazolo[4,5-d]pyrimidines:

| Ex. No. | Ar | R$^1$ | m.p. (° C.) |
|---|---|---|---|
| 401 | 2,4,6-Me$_3$—Ph | H | 146–147 |
| 402 | 4-Br-2,6-Me$_2$—Ph | H | 139–140 |
| 403 | 2,4,6-Me$_3$—Ph | CF$_3$ | 176–177 |
| 404 | 4-Br-2,6-Me$_2$—Ph | CF$_3$ | 183–184 |
| 405 | 2-Cl-4,6-Me$_2$—Ph | CF$_3$ | 174–175 |
| 406 | 2,4-Cl$_2$-6-Me—Ph | CF$_3$ | 160–161 |
| 407 | 2-Cl-4,6-Me$_2$—Ph | C$_2$H$_5$ | 111–112 |
| 408 | 2-Cl-4,6-Me$_2$—Ph | MeOCH$_2$ | 87–88 |

EXAMPLE 409

6-[N-(2-chloro-4,6-dimethylphenyl)]-9-[(1-methoxymethyl)propyl]-2-methyl-9H-purin-6,8-diamine Part A 2-methyl-4-chloro-6-(1-methoxymethyl) propylamino-5-aminopyridine (450 mg, 1.84 mmol) was reacted with cyanogen bromide (234 mg, 2.2 mmol) in refluxing methanol for 24 h. The solvent was removed in vacuo and the resulting crude oil was taken up in ethyl acetate and washed 3 times with saturated aqueous NaHCO$_3$. The organic layer was dried then stripped in vacuo and the crude product was chromatographed on silica gel (20 g, ethyl acetate neat) providing 240 mg (48%) of 8-amino-6-chloro-9-[(1-methoxymethyl)propyl-2-methyl-9H-purine.

Part B

The product from part B (50 mg, 0.20 mmol) was treated with 2-chloro-4,6-dimethylaniline (30 mg, 0.20 mmol) in refluxing 1.0 N HCl for 24 h. The reaction was cooled then poured into saturated aqueous NaHCO$_3$ and extracted (3 times 50 ml) with ethyl acetate. The organic fractions were combine, dried and stripped in vacuo. The resulting crude product was chromatographed on silica gel (20 g, ethyl acetate neat) providing 55 mg (71%) of the title compound. Anal. Calcd. for C$_{19}$H$_{25}$N$_6$OCl: C, 58.76; H, 6.44; N, 21.65. Found: C, 58.50; H, 6.32; N, 21.72.

The compounds of Table 7 can be made by the methods exemplified in Examples 209–211 and 409.

TABLE 7

9H-imidazo[4,5-d]pyrimidines:

| Ex. No. | Ar | R$^2$ | R$^3$ | m.p. (° C.) |
|---|---|---|---|---|
| 410 | 2,4,6-(Me)$_3$—Ph | H | CH(Et)CH$_2$OCH$_3$ | 212–213 |
| 411 | 2,4,6-(Me)$_3$—Ph | NH$_2$ | CH(Et)CH$_2$OCH$_3$ | oil |
| 412 | 2-Cl-4,6-(Me)$_2$—Ph | NH$_2$ | CH(CH$_2$OCH$_3$)$_2$ | oil |
| 413 | 2,4,6-(Me$_3$)—Ph | NH$_2$ | CH(CH$_2$OCH$_3$)$_2$ | oil |

EXAMPLE 414

(S)-(−)-N-(2-chloro-4,6-dimethylphenyl)-6-methyl-1-(1-methoxymethyl-3-methoxypropyl)-1H-1,2,3-triazolo[4,5-c]pyridin-4-amine Part A L-Dimethyl aspartate hydrochloride (5 g, 25.3 mmol) and triphenylmethyl chloride (7.65 g, 27.5 mmol) were suspended in dry CH$_3$CN (50 mL) at 0° C. To that Et$_3$N (4.5 mL, 32.3 mmol) was added dropwise, followed by N-methylmorpholine (2.5 mL, 27.5 mmol). The mixture was stirred at 0° C. for 1 h and at 25° C. for 30 min. Then it was partitioned between EtOAc (200 mL) and water (50 mL) and the organic extract was washed with water (50 mL), brine (50 mL), dried (MgSO$_4$) and stripped in vacuo. The product, diethyl N-triphenylmethyl aspartate, was >90% clean by NMR analysis. NMR(CDCl$_3$)d 7.16–7.51 (m, 15 H), 3.68 (s, 3H), 3.66–3.74 (m, 1H), 3.26 (s, 3H), 2.93 (d, 1H, J=9.9 Hz), 2.63–2.69 (dd, 1H, J$_1$=14.6, J$_2$=5.1 Hz), 2.48–2.55 (dd, 1H, J$_1$=14.6 Hz, J$_2$=7 Hz).

Part B (S)-Diethyl N-triphenylmethyl aspartate (~25 mmol) was dissolved in dry THF (150 mL) and cooled to 0° C. To that a 1 M solution of of LiAlH$_4$ in THF (50 mL, 50 mmol) was added dropwise and the reaction was stirred for 2 h and allowed to warm to 25° C. Then it was cooled and quenched with water (5 mL) and 1 N NaOH (4 mL), diluted with ether (200 mL) and the precipitated solids were filtered off. The filtrate was concentrated in vacuo to give the product, 2-N-triphenylamino-1,4-butane diol (>90% clean by NMR analysis). NMR(CDCl$_3$)d 7.17–7.57 (m, 15H), 3.68–3.77 (m, 1H), 3.56–3.63 (m, 1H), 3.19 (d, 1H, J=8.8 Hz), 2.76–2.86 (m, 2H), 2.2–2.7 (br, 3H), 1.54–1.63 (m, 1H), 1.36–1.54 (m, 1H).

Part C (S)-2-N-triphenylamino-1,4-butane diol (~25 mmol) dissolved in dry THF (50 mL) was added into a suspension of NaH 60% in oil (2.34 g, 58.5 mmol) in dry THF (50 mL) at 0° C., and the mixture was stirred at 9° C. for 30 min and at 25° C. for 1 h. Then it was cooled in an ice bath and CH$_3$I (3.6 mL, 58.5 mmol) was added dropwise. The reaction was stirred at 0° C. for 30 min and at 25° C. for 2 h, the excess NaH was quenched with water and the THF was stripped off. The residue was partitioned between EtOAc (200 mL) and water (50 mL) and the organic extract was washed with water (50 mL), brine (50 mL), dried (MgSO$_4$) and stripped in vacuo. The product, 2-N-triphenylamino-1,4-dimethoxy butane was >90% clean by NMR analysis. NMR(CDCl$_3$)d 7.15–7.59 (m, 15 H), 3.34–3.41 (m, 1H), 3.22–3.30 (m, 1H), 3.24 (s, 3H), 3.03 (s, 3H), 2.86 (dd, 1H, J$_1$=9.5 Hz, J$_2$=3.3 Hz), 2.65–2.75 (m, 1H), 2.4–2.46 (br, 1H), 2.30–2.35 (m, 1H), 2.57–2.8 (m, 2H).

Part D (S)-2-N-Triphenylamino-1,4-dimethoxy butane (~25 mmol) was dissolved in a mixture of CH$_2$Cl$_2$ (100 mL) and methanol (50 mL) and 1 M HCl in ether was added (50 mL). The reaction was stirred at 25° C. for 16 h, the solvent was stripped off and the residue was washed with 1:1 ether/hexane (3×50 mL). The remaining oil, 2-amino-1,4-dimethoxybutane hydrochloride, was dried under vacuum (3.87 g, 88%). NMR(CDCl$_3$)d 8.2–8.5 (br, 3H), 3.5–3.7 (m, 5H), 3.41 (s, 3H), 3.36 (s, 3H), 2.05–2.2 (m, 1H), 1.90–2.01 (m, 1H).

Part E (S)-6-Methyl-3-nitro-4-(1-methoxymethyl-3-methoxypropylamino)pyridone 1-methoxymethyl-3-methoxypropylamine (4.19 g, 22.3 mmol), and 4-chloro-6-methyl-3-nitropyridone (3.87 g, 22.3 mmol) were mixed in CH$_3$CN (70 mL) and diisopropyl-ethylamine (9.4 mL, 53.6 mmol) was added. The reaction was stirred at 25° C. for 16 h and at reflux for 2.5 h. The solvent was stripped off and the residue was dissolved in CH$_2$Cl$_2$ (150 mL) and the CH$_2$Cl$_2$ was washed with water (80 mL). The water was extracted with CH$_2$Cl$_2$ (50 mL) and the combined organic extracts were dried (MgSO$_4$) and stripped in vacuo. The residue was crystallized from EtOAc and washed with 40% EtOAc/hexanes to give the product, (4.8 g, 75%). NMR(DMSO)d 9.13 (d, 1H, J=8.8 Hz), 5.9 (s, 1H), 3.92–4.02 (m, 1H), 3.20–3.25 (m, 2H), 3.28–3.4 (m, 2H), 3.25 (s, 3H), 3.18 (s, 3H), 2.09 (s, 3H), 1.65–1.90 (m, 2H).

Part F (S)-2-Chloro-6-methyl-3-nitro-N-(1-methoxymethyl-3-methoxypropyl)pyridin-4-amine 4-[3-(1,4-dimethoxybutyl)amino]-6-methyl-3-nitropyridone (4.8 g, 16.82 mmol) was dissolved in POCl$_3$ (50 mL) and stirred at 25° C. for 40 h. Then the reaction was poured into ice/water (500 mL), allowed to react, neutralized with solid NaHCO$_3$ after EtOAc was added (150 mL) and extracted with EtOAc (2×300 mL). The EtOAc was dried (MgSO$_4$) and stripped in vacuo to give the product. NMR (CDCl$_3$)d 7.08 (d, 1H, J=7.7 Hz), 6.65 (s, 1H), 3.85–3.95 (m, 1H), 3.30–3.50 (m, 4H), 3.38 (s, 3H), 3.33 (s, 3H), 2.43 (s, 3H), 1,80–2.02 (m, 2H).

Part G (S)-3-amino-2-chloro-4-N-(1-methoxymethyl-3-methoxypropyl)-6-methyl-pyridin-4-amine 2-Chloro-6-methyl-3-nitro-N-(1-methoxymethyl-3-methoxypropyl)pyridin-4-amine (~16.82 mmol) was heated at reflux with Fe powder (10 g) in methanol (120 mL) in the presence of glacial acetic acid (10 mL) for 2 h. Then the iron was filtered through celite, the celite was washed with methanol(80 mL) and the filtrate was stripped in vacuo. The residue was dissolved in 10% HCl (120 mL) and EtOAc was added (160 mL). The mixture was neutralized with solid NaHCO$_3$ and the aqueous layer was extracted with EtOAc (2×100 mL). The combined organic extracts were washed with brine (50 mL), dried (MgSO$_4$) and stripped in vacuo (4.1 g). NMR(CDCl$_3$)d 6.4 (s, 1H), 5.2–5.35 (br s, 1H), 3.70–3.80 (m, 1H), 3.2–3.8 (m, 6H), 3.38 (s, 3H), 3.33 (s, 3H), 2.42 (s, 3H), 1.8–2.0 (m, 2H).

Part H (S)-4-chloro-1-(1-methoxymethyl-3-methoxypropyl)-6-methyl-1H-1,2,3-triazolo[4,5-c]pyridine 3-amino-2-chloro-6-methyl-4-N-(1-methoxymethyl-3-methoxypropyl)pyridin-4-amine (4.1 g, 14.98 mmol) was dissolved in a mixture of CH$_2$Cl$_2$ (40 mL) and 50% acetic acid (40 mL) and cooled to 0° C. in an ice bath. To that a solution of NaNO$_2$ (1.84 g, 26.86 mmol) in water (10 mL) was added dropwise and the reaction was stirred at 0° C. for 30 min and at 25° C. for 1.5 h. Then the acetic acid was neutralized with solid NaHCO$_3$ and water (80 mL) was added. The mixture was extracted with EtOAc (2×100 mL) and the combined organic extracts were combined and washed with brine (50 mL), dried and stripped in vacuo. The residue was chromatographed on silica gel (40% EtOAc/hexanes eluent) to give the product (4.05 g, 56% overall for the eight steps). NMR(CDCl$_3$)d 7.25 (s, 1H), 5.04–5.13 (m, 1H), 3.98 (dd, 1H, J$_1$=9.9 Hz, J$_2$=8.4 Hz), 3.84 (dd, 1H, J$_1$=10.2 Hz, J$_2$=4.4 Hz), 3.39 (dt, 1H, J$_1$=9.9 Hz, J$_2$=4.8 Hz), 3.25 (s, 3H), 3.17 (s, 3H), 2.91 (dt, 1H, J$_1$=9.5 Hz, J$_2$=4.0 Hz), 2.68 (s, 3H), 2.22–2.6 (m, 2H).

Part I (S)-4-chloro-1-(1-methoxymethyl-3-methoxypropyl)-6-methyl-1H-1,2,3-triazolo[4,5-c]pyridine (2.0 g, 7 mmol) and 2-chloro-4,6-dimethylaniline (1.094 g, 7 mmol) were dissolved in dry THF and cooled to 0° C. in an ice bath. To that a 1 M solution sodium hexamethyldisilazide (16 mL, 16 mmol) was added dropwise and the solution was stirred at 0° C. for 45 min. Then it was quenched with water (30 mL) and partitioned between EtOAc and water (20 mL). The organic extract was washed with brine (50 mL), dried (MgSO$_4$) and stripped in vacuo. The residue was purified by silica gel chromatography (40% EtOAc/hexanes eluent) and crystallized from hexanes to give the product (2.42 g, 85%), mp 108–109° C., [a]D25–32.38 (c=0.200 g/dL, CHCl$_3$) 99.6% ee by chiral HPLC. This was converted to the methylsulfonate salt, mp 98–100° C., after crystallization from ether/hexanes, [a]D25–29.00 (c=0.200 g/dL, CHCl$_3$).

EXAMPLE 414A (R,S)-N-(2-chloro-4,6-dimethylphenyl]-6-methyl-1-(1-methoxymethyl-3-methoxypropyl)-1H-1,2,3-triazolo[4,5-c]pyridin-4-amine Part A (R,S)-2-Aminobutyrolactone hydrobromide (8.0 g, 44 mmol) and triphenylmethyl chloride (12.8 g, 46 mmol) were suspended in dry CH$_3$CN (80 mL) at 25° C. To that Et$_3$N (13.6 mL, 100 mmol) was added dropwise, the reaction mixture was stirred at 25° C. for 4 h and partitioned between EtOAc (120 mL) and water (50 mL). The organic layer was washed with water (50 mL), brine (50 mL), dried (MgSO$_4$) and stripped in vacuo. The residue was recrystallized from EtOAc/hexanes to give 2-triphenylmethylamino-butyrolactone (10.5 g).

Part B

Lithium aluminum hydride (1.4 g, 36 mmol) was suspended in dry THF (50 mL) and cooled to 0° C. in an ice bath. To that a solution of 2-triphenylmethylamino-butyrolactone (11 g, 31.9 mmol) in dry THF (70 mL) was added dropwise over a period of 20 min. After the addition was over the reaction mixture was stirred at 0° C. for 1 h, at 25° C. for 3 h and quenched by the sequential addition of water (2 mL) 1 N NaOH (2 mL) and water (3 mL), and diluted with ether (150 mL). The precipitated solids were filtered off and the filtrate was concentrated in vacuo to give (R,S)-2-N-triphenylamino-1,4-butanediol. This was used in the same synthetic scheme as previously described for the chiral material (Example 414, Parts C-I) to obtain the racemic material.

The compounds listed in Table 8 were prepared by the methods exemplified in Examples 221–232, 259, 414 and 414A.

TABLE 8

1H-1,2,3-triazolo[4,5-c]pyridines:

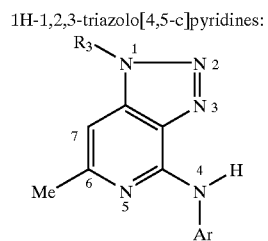

| Ex. No. | R³ | Ar | m.p. (° C.) |
|---|---|---|---|
| 415 | CH(Et)₂ | 4-Br-2,6-(Me)₂—Ph | 191–192 |
| 416 | CH(Et)₂ | 2,6-(Me)₂-4-SMe—Ph | 172–173 |
| 417 | CH(Et)₂ | 2-Cl-4,6-(Me)₂—Ph | 171–172 |
| 418 | CH(Et)₂ | 2,4-(Cl)₂-6-Me—Ph | 164–165 |
| 419 | CH(Et)₂ | 2,4-(Me)₂—Ph | 90–91 |
| 420 | CH(Et)₂ | 2-Me-4-OMe—Ph | 104–105 |
| 421 | CH(Et)₂ | 2-Br-4,6-(Me)₂—Ph | 178–179 |
| 422 | CH(Et)₂ | 4-CN-2,6-(Cl)₂—Ph | 189–190 |
| 423 | CH(Et)₂ | 3-Br-2,4,6-(Me)₃—Ph | 156–157 |
| 424 | CH(Et)₂ | 4-Br-2-SMe—Ph | 112–114 |
| 425 | CH(Et)₂ | 2-CN-4,6-Me₂—Ph | 181–183 |
| 426 | CH(Et)₂ | 2-Br-5-F-4-Me—Ph | 132–134 |
| 427 | CH(Et)₂ | 4-Br-5-F-2-Me—Ph | 115–116 |
| 428 | CH(Et)₂ | 2,4-Br₂—Ph | 164–166 |
| 429 | CH(Et)₂ | 4-Ac-2-SMe—Ph | 142–144 |
| 430 | CH(Et)₂ | 4-Br-2-Cl—Ph | 152–153 |
| 431 | CH(Et)₂ | 2,4-Cl₂—Ph | 134–135 |
| 432 | CH(Et)₂ | 2,4-Me₂-6-SMe—Ph | 135–136 |
| 433 | CH(Et)n-Pr | 2,4,6-(Me)₃—Ph | 117–118 |
| 434 | CH(Et)CH₂OMe | 4-Br-2,6-(Me)₂—Ph | 165–166 |
| 435 | CH(Et)CH₂OMe | 2-Cl-4,6-(Me)₂—Ph | 126–127 |
| 436 | CH(Et)CH₂OMe | 3-Br-2,4,6-(Me)₃—Ph | 117–118 |
| 437 | CH(Et)CH₂OMe | 2,4-(Cl)₂-6-Me—Ph | 131–134 |
| 438 | CH(Et)CH₂OMe | 2-Br-4,6-(Me)₂—Ph | 127–128 |
| 439 | CH(Et)CH₂OMe | 4-Br-2-Cl-6-Me—Ph | 136–137 |
| 440 | CH(Et)CH₂OMe | 4-Br-2,6-(Cl)₂—Ph | 119–120 |
| 441 | CH(Et)CH₂OMe | 2,4-(Me)₂—Ph | 76–77 |
| 442 | CH(Et)CH₂OMe | 4-MeO-2-Me—Ph | 76–77 |
| 443 | CH(Et)CH₂OMe | 2,4,5-(Me)₃—Ph | 94–95 |
| 444 | CH(Et)CH₂OMe | 2-Cl-4,6-(OMe)₂—Ph | 167–168 |
| 445 | CH(Et)CH₂OMe | 2,4,5-(Cl)₃—Ph | 151–152 |
| 446 | CH(Et)CH₂OMe | 2,5-(Cl)₂-4-NO₂—Ph | 157–158 |
| 447 | CH(Et)CH₂OMe | 2-CN-4,5-(OMe)₂—Ph | 162–163 |
| 448 | CH(Et)CH₂OMe | 2-Me-4,5-(OMe)₂—Ph | 118–119 |
| 449 | CH(Et)CH₂OMe | 2,6-Cl₂-4-OMe—Ph | 136–137 |
| 450 | CH(Et)CH₂OCH₃ | 4-Br-2-OMe-6-Me—Ph | 159–162 |
| 451 | CH(Et)CH₂OCH₃ | 4-Br-5-F-2-Me—Ph | 111–113 |
| 452 | CH(Et)CH₂OCH₃ | 2-CN-4,6-Me₂—Ph | 154–156 |
| 453 | CH(Et)CH₂OCH₃ | 2-OMe-4,6-Me₂—Ph | 115–116 |
| 454 | CH(Et)CH₂OCH₃ | 2-Ac-4-Cl-6-Me—Ph | 127–129 |
| 455 | CH(Et)CH₂OCH₃ | 2-Br-4,6-F₂—Ph | 138–140 |
| 456 | CH(Et)CH₂OCH₃ | 2,4,6-Me₃—Ph | 119–121 |
| 457 | CH(Et)CH₂OCH₃ | 4-Br-2-SMe—Ph | 70–73 |
| 458 | CH(Et)CH₂OCH₃ | 2,4-Br₂—Ph | 119–120 |
| 459 | CH(Et)CH₂OCH₃ | 2,4,6-Me₃—Ph | 113–115 |
| 460 | CH(Et)CH₂OCH₃ | 2,4,6-Me₃—Ph | 113–115 |
| 461 | CH(Et)CH₂OCH₃ | 2,4-Me₂-6-SMe—Ph | 104–106 |
| 462 | CH(Et)CH₂OCH₃ | 4-Br-2-Me—Ph | amorph. |
| 463 | CH(Et)CH₂OCH₃ | 4-I-2-Me—Ph | 103–105 |
| 464 | CH(Et)CH₂OCH₃ | 3-F-2,4,6-Me₃—Ph | amorph. |
| 465 | CH(Et)CH₂OCH₃ | 4-Cl-2-Me—Ph | 104–105 |
| 466 | CH(Et)CH₂OCH₃ | 4-Br-2,6-F₂—Ph | 138–140 |
| 467 | CH(Et)CH₂OCH₃ | 4-Cl-2-CN-6-Me—Ph | 177–180 |

TABLE 8-continued 1H-1,2,3-triazolo[4,5-c]pyridines:

| Ex. No. | R³ | Ar | m.p. (° C.) |
|---|---|---|---|
| 468 | CH(CH₂OMe)₂ | 2,4,6-(Me)₃—Ph | 115–116 |
| 469 | CH(CH₂OMe)₂ | 4-Br-2,6-(Me)₂—Ph | 145–146 |
| 470 | CH(CH₂OMe)₂ | 2,4-(Cl)₂-6-Me—Ph | 111–112 |
| 471 | CH(CH₂OMe)₂ | 3-Br-2,4,6-(Me)₃—Ph | 105–106 |
| 472 | CH(CH₂OMe)₂ | 2,4,5-(Me)₃—Ph | 110–111 |
| 473 | CH(CH₂OMe)₂ | 2-Br-4-CH(Me)₂—Ph | 107–108 |
| 474 | CH(CH₂OMe)₂ | 2-Br-4,6-(Me)₂—Ph | 83–84 |
| 475 | CH(CH₂OMe)₂ | 2,4-(Me)₂—Ph | 72–73 |
| 476 | CH(CH₂OMe)₂ | 4-MeO-2-Me—Ph | 65–67 |
| 477 | CH(CH₂OMe)₂ | 4-CH(Me)₂—Ph | oil |
| 478 | CH(CH₂OMe)₂ | 2,5-Cl₂-4-N(Me)₂—Ph | 110–111 |
| 479 | CH(CH₂OMe)₂ | 2-Me-4,5-(OMe)₂—Ph | 111–112 |
| 480 | CH(CH₂OMe)₂ | 4-Cl-2,5-(OMe)₂—Ph | 167–168 |
| 481 | CH(CH₂OMe)₂ | 2-Cl-4,5-(Me)₂—Ph | 169–170 |
| 482 | CH(CH₂OMe)₂ | 2,6-(Cl)₂-4-OMe—Ph | 145–146 |
| 483 | CH(CH₂OMe)₂ | 4-t-Bu-2,6-(Me)₂—Ph | 134–135 |
| 484 | CH(CH₂OMe)₂ | 4-Cl-2-Me-5-NO₂—Ph | 163–164 |
| 485 | CH(CH₂OMe)₂ | 4-Br-2-Cl-5-Me—Ph | 159–160 |
| 486 | CH(CH₂OMe)₂ | 2-Cl-4-OMe-6-Me—Ph | 117–118 |
| 487 | CH(CH₂OMe)₂ | 4-Cl-2,5-Me₂—Ph | 115–116 |
| 488 | CH(CH₂OMe)₂ | 2-Cl-4-CN-6-Me—Ph | 127–128 |
| 489 | CH(CH₂OMe)₂ | 4-Br-2,6-(Et)₂—Ph | 168–169 |
| 490 | CH(CH₂OMe)₂ | 4-Br-2-Cl-6-Me—Ph | 104–105 |
| 491 | CH(CH₂OMe)₂ | 2-Cl-4,6-(OMe)₂—Ph | 139–140 |
| 492 | CH(CH₂OMe)₂ | 2-Br-4,6-(OMe)₂—Ph | 155–156 |
| 493 | CH(CH₂OMe)₂ | 5-Cl-4-NMe₂-2-OMe—Ph | 110–111 |
| 494 | CH(CH₂OMe)₂ | 2,4-(Cl)₂-5-CF₃—Ph | 162–163 |
| 495 | CH(CH₂OMe)₂ | 4-Cl-2-OMe-5-CF₃—Ph | 161–162 |
| 496 | CH(CH₂OMe)C₂H₄OMe | 4-Cl-2-Et-6-Me—Ph | 101–103 |
| 497 | CH(CH₂OMe)C₂H₄OMe | 2-F-4,6-Me₂—Ph | 172–174 |
| 498 | CH(CH₂OMe)C₂H₄OMe | 2,4-Me₂-6-SMe—Ph | 147–148 |
| 499 | CH(CH₂OMe)C₂H₄OMe | 2-Br-4,6-Me₂—Ph | 144–147 |
| 500 | CH(CH₂OMe)C₂H₄OMe | 4-Cl-2,6-Me₂—Ph | 97–100 |
| 501 | CH(CH₂OMe)C₂H₄OMe | 4-Br-2-Et-6-Me—Ph | 111–113 |
| 502 | CH(CH₂OMe)C₂H₄OMe | 2,4,6-Me₃—Ph | 115–116 |
| 503 | CH(CH₂OMe)C₂H₄OMe | 4-Br-2,6-Me₂—Ph | amorph. |
| 504 | CH(CH₂OMe)C₂H₄OMe | 4-Br-2-OMe-6-Me—Ph | 131–133 |
| 505 | CH(CH₂OMe)C₂H₄OMe | 2-Cl-4,6-Me₂—Ph | 127–129 |
| 506 | CH(CH₂OMe)C₂H₄OMe | 2-I-4,6-Me₂—Ph | 150–152 |
| 507 | CH(CH₂OMe)C₂H₄OMe | 2-Cl-4-I-6-Me—Ph | 119–120 |
| 508 | CH(CH₂OMe)C₂H₄OMe | 3-F-2,4,6-Me₃—Ph | amorph. |
| 509 | CH(CH₂OMe)C₂H₄OMe | 2-Cl-4,6-Me₂—Ph | 127–129 |
| 510 | CH(CH₂OMe)C₂H₄OMe | 2-Cl-4,6-Me₂—Ph | 108–109 |
| 511 | CH(CH₂OMe)C₂H₄OMe | 2-Br-6-F-4-Me—Ph | 150–152 |
| 512 | CH(CH₂OMe)C₂H₄OMe | 2-Cl-5-F-4,6-Me₂—Ph | 107–108 |
| 513 | CH(CH₂OMe)C₂H₄OMe | 3-F-2,4,6-Me₃—Ph | 117–119 |
| 514 | CH(CH₂OMe)C₂H₄OMe | 3-F-2,4,6-Me₃—Ph | 117–119 |
| 515 | CH(CH₂OMe)C₂H₄OMe | 2-Cl-5-F-4,6-Me₂—Ph | 107–109 |
| 516 | CH(CH₂OMe)C₂H₄OMe | 4-Br-2,6-Me₂—Ph | — |
| 517 | CH(CH₂OMe)C₂H₄OMe | 4-Br-2,6-Me₂—Ph | amorph. |
| 518 | CH(CH₂OMe)C₂H₄OMe | 2,4,5-Me₃—Ph | oil |
| 519 | CH(CH₂OMe)C₂H₄OMe | 2,4,5-Me₃—Ph | oil |
| 520 | CH(CH₂OMe)C₃H₆OMe | 2,4,6-Me₃—Ph | 128–130 |
| 521 | CH(CH₂OMe)C₃H₆OMe | 4-Cl-2,6-Me₂—Ph | 114–115 |
| 522 | CH(Bz)CH₂OMe | 2,4,6-(Me)₃—Ph | 55–57 |
| 523 | CH(Bz)CH₂OMe | 2,4-(Cl)₂-6-Me—Ph | 64–65 |

Note: (+), (−), (R) or (S) denotes respective isomers.

The compounds listed in table 9 were prepared by the methods exemplified in Examples 209–211 using the intermediate from example 259, part G.

TABLE 9

1H-imidazo[4,5-c]pyridines:

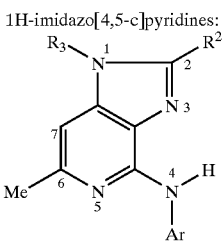

| Ex. No. | Ar | R² | R³ | m.p. (° C.) |
|---|---|---|---|---|
| 524 | 2-Cl-4,6-(Me)₂—Ph | H | CH(CH₂OCH₃)₂ | 129–130 |
| 525 | 2-Cl-4,6-(Me)₂—Ph | Me | CH(CH₂OCH₃)₂ | 156–157 |

EXAMPLE 526

This example illustrates an alternative method for making the compound of Example 32.

Part A

(+/−)-1-Methoxy-2-butanol Methanesulfonate (1)

A solution of 1-methoxy-2-butanol (52.08 g, 57.23 mL, 0.5 mol) and Et₃N (108.2 mL, 0.75 mol, 1.5 equiv) in CH₂Cl₂ (500 mL) was treated dropwise with methanesulfonyl chloride (68.73 g, 46.44 mL, 0.6 mol, 1.2 equiv) at 0° C. under N₂. The reaction mixture was warmed to 25° C. and stirred at 25° C. for an additional 4 h before being quenched with H₂O (300 mL). The two layers were separated, and the aqueuos was extracted with CH₂Cl₂ (3×100 mL). The combined CH₂Cl₂ extracts were washed with H₂O (2×200 mL) and saturated aqueuos NaCl (200 mL), dried (MgSO₄), and concentrated in vacuo. The residue was dried enough in vacuo to afforded the desired mesylate 1 (85–90.0 g, 91 g theoretical, 93–98%) as a pale-yellow oil, which was pure enough and directly used in the next reaction without further purification.

The analytically pure sample of 1 was obtained by silicon-gel column chromatography purification and 1 was obtained as a colorless oil.

Part B

(+/−)-1-Methoxy-2-butyl Azide (2)

A solution of crude mesylate 1 (90.0 g, 0.495 mol) in DMF (500 mL) was treated with NaN₃ (48.22g, 0.74 mol, 1.5 equiv) at 25° C. under N₂. The resulting reaction mixture was warmed to 55–60° C. for 6–8 h with stirring before being quenched with H₂O (500 mL). The pale-yellow solution was then extracted with EtOAc or Et₂O (4×200 mL). The combined EtOAc (or Et₂O) extracts were washed with H₂O (3×500 mL), dried (MgSO₄), and concentrated in vacuo. The residual solution was found to contain desired azide 2 (60.3 g, 64.5 g theoretical, 94%), which was found to be pure enough and directly used in the following reaction without further purification.

The analytically pure sample of 2 was obtained by SiO₂ column chromatography purification as a colorless, low boiling-point liquid.

Part C

(+/−)-4-Amino-5-carbamoyl-1-(1-methoxy-2-)butyl-1H-1,2,3-triazole (3)

A suspension of cyanoacetamide (46.5 g, 0.553 mol, 1.2 equiv) in absolute EtOH (200 mL) was treated with EtONa (62.73 g, 0.922 mol, 2.0 equiv) at 25° C. under N₂, and the resulting mixture was warmed to reflux for 15 min under N₂. The cooled mixture was then treated with a solution of 1-methoxy-2-butyl azide 2 (59.5 g, 0.467 mol) in Et₂O and the mixture was diluted with additional EtOH (260 mL) at 25° C. The resulting reaction mixture was warmed to reflux and stirred for 6–8 h at reflux before being cooled to room tempearture. The solvent was removed in vacuo, and the residue was treated with H₂O (300 mL) and EtOAc (300 mL). The two layers were separated, and the aqueous was extracted with EtOAc (5×100 mL). The combined EtOAc extracts were washed with saturated aqueous NaCl (50 mL), dried in vacuo, and concentrated in vacuo. The residual yellow solid was directly recrystalized from MeOH (100–150 mL) to afford the desired 1,2,3-triazole 3 (70.7 g, 98.2 g theoretical, 72%) as white crystals.

Part D

(+/−)-9-(1-Methoxy-2-)butyl-2-methyl-8-azaadenine (4)

Method A

A solution of 3 (10.65 g, 0.05 mol) in absolute EtOH (50 mL) was treated with EtONa (6.8 g, 0.1 mol, 2.1 equiv) and EtOAc (8.8 g, 10.0 mL, 0.5 mol, 10 equiv) at 25° C. under N₂, and the resulting reaction mixture was warmed to reflux with stirring for 6–8 h before being quenched with H₂O (50 mL). The solution was then concentrated in vacuo to remove most of EtOH. The residue was treated with H₂O (50 mL), acidified with concentrated HCl (pH 6–7), and extracted with EtOAc (5×50 mL). The combined EtOAc extracts were washed with saturated aqueous NaCl (20 mL), dried (MgSO₄), and concentrated in vacuo. The residual pale-yellow solid was directly recrystalized from 80% EtOAc-Hexane or EtOH to afford 8-azaadenine 4 (8.4 g, 11.85 theoretical, 71%) as white crystals.

Method B

A suspension of cyanoacetamide (47.1 g, 0.561 mol, 1.2 equiv) in absolute EtOH (200 mL) was treated with EtONa (95.3 g, 1.4 mol, 3.0 equiv) at 25° C. under N₂, and the resulting mixture was warmed to reflux for 15 min. under N₂. The cooled mixture was then treated with a solution of 1-methoxy-2-butyl azide 2 (60.3 g, 0.467 mol) in EtOAc (or Et₂O) in absolute EtOH (170 mL) at 25° C., and the resulting reaction mixture was warmed to reflux and stirred 4–6 h at reflux before being cooled to RT. EtOAc (120 mL) was added to the reaction mixture, and the resulting mixture was warmed to reflux for an additional 6–10 h. The cooled reaction mixture was treated with H₂O (200 mL), and the solution was concentrated in vacuo to remove most of EtOH. The residue was treated with H₂O (100 mL) and acidified with concentrated HCl (pH 6–7), and extracted with EtOAc (6×150 mL). The combined EtOAc extracts were washed with saturated aqueous NaCl (100 mL), dried (MgSO₄), and concentrated in vacuo. The residual pale-yellow solid was recrystalized from 80% EtOAc-Hexane (or EtOH) to afford 8-azaadenine 4 (70.8 g, 110.7 g theoretical, 64% for two steps) as white crystals.

Part E

(+/−)-4-Chloro-1-(1-methoxy-2-)butyl-2-methyl-8-azaadenine (5)

Method A

A solution of 4 (6.78 g, 0.017 mol) in POCl₃ (30 mL) was warmed to reflux for 3 h. The excess POCl₃ was removed in vacuo, and the residue was treated with H₂O (50 mL) and EtOAc (50 mL). The two layers were separated, and the aqueous was extracted with EtOAc (3×50 mL). The combined EtOAc extracts were washed with H₂O (2×50 mL) and saturated aqueous NaCl (30 mL), dried (MgSO$_4$), and concentrated in vacuo. Flash chromatography (SiO$_2$, 10–20% EtOAc-Hexane gradient elution) afforded 5 (6.65 g, 7.30 g theoretical, 91%) as a colorless oil, which solidified upon standing in vacuo.

Method B

A solution of 4 (170 mg, 0.72 mmol) was treated with POCl$_3$ (2 mL) and N,N-diethylaniline (0.5 mL) at 25° C. under N$_2$, and the resulting mixture was warmed to reflux for 4–6 h. The excess POCl$_3$ was removed in vacuo, and the residue was directly purified by flash chromatography (SiO$_2$, 10–20% EtOAc-Hexane gradient elution) to afford 5 (159 mg, 184 mg theoretical, 86%) as a colorless oil, which solidified in vacuo. The product obtained by Method B was identical in all comparable respects with that obtained from Method A.

Part F (+/−)-1-(1-Methoxy-2-)butyl-2-methyl-4-[(2,4,6-trimethyl)phenyl]amino-8-azaadenine (6)

A solution of 5 (7.0 g, 0.0274 mol) in toluene (50 mL) was treated with 2,4,6-trimethylphenyl amine (8.1 g, mL, 0.06 mol, 2.2 equiv) at 25° C. under N$_2$. The resulting reaction mixture was warmed to reflux for 6–8 h under N$_2$. The white solid (2,4,6-trimethylaniline HCl salt) was filtered and the solid was washed with toluene (10–20 mL). The filtrate was concentrated in vacuo. The residual pale-yellow solid was recrystalized from 30% EtOAc-Hexane to afford the title compound 6 (7.9 g, 9.7 g theoretical, 81%) as white crystals.

EXAMPLE 527

This illustrates an alternative method for making the compound of Example 259.

Part A 2-(2-Chloro-4,6-dimethyl)-phenylamino-4-(1,3-dimethoxy-2-propyl)amino-6-methyl-3-nitropyridine (3)

A suspention of p-toluenesulfonic acid monohydrate (6.84 g., 36 mmol., 1.2 equiv.) in toluene (150 mL) was warmed to reflux for 2 h, and the azeotropic mixture of water and toluene (50 mL) was removed during the course of the azeotropic distillation. After the mixture was cooled down to room temperature, 2-chloro-4-(1,3-dimethoxy-2-propyl)amino-6-methyl-3-nitropyridine hydrochloride salt (1, 9.8 g, 30 mmol) and 2-chloro-4,6-dimethylaniline (2, 4.68 g, 30 mmol, 1.0 equiv) were introduced to the reaction mixture, and the resulting reaction mixture was warmed to reflux for 6 h. The reaction mixture was then cooled down to room temperature, and was subsequently treated with saturated aqueous NaHCO$_3$ solution (100 mL) and tert-butyl methyl ether (TBME, 100 mL). The two layers were separated, and the aqueous layer was extracted with TBME (2×50 mL). The combined organic extracts were washed with saturated aqueous NaHCO$_3$ solution (50 mL), H$_2$O (50 mL), and saturated aqueous NaCl solution (50 mL), dried (MgSO$_4$), and concentrated in vacuo. The residue was then directly purified by flash column chromatography (SiO$_2$, 15–30% EtOAc-hexane gradient elution) to afford the desired 3 (7.63 g, 12.26 g theoretical, 62.3%) as a yellow oil, which was solidified upon standing at room tempreture in vacuo. The analytically pure material was obtained from recrystalization of the chromatographically pure 3 from TBME/hexane (1:5) as yellow crystals.

Part B

3-Amino-2-(2-chloro-4,6-dimethyl)-phenylamino-4-(1,3-dimethoxy-2-propyl)amino-6-methylpyridine (4)

A solution of 3 (3.0 g, 7.34 mmol) in THF (10 mL) was treated with ammonium hydroxide (28–30% aqueous solution, 10 mL, 73 mmol, 10 equiv), Na$_2$S$_2$O$_4$ (6.38 g, 36.7 mmol, 5.0 equiv) and H$_2$O (10 mL) at room temperature under N$_2$. The resulting reaction mixture was then stirred at room temperature for 12 h before being treated with H$_2$O (20 mL) and EtOAc (50 mL). The two layers were separated, and the aqueous layer was extracted with EtOAc (4×20 mL). The combined organic extracts were washed with saturated NaHCO$_3$ aqueous solution (20 mL), H$_2$O (20 mL), and saturated NaCl aqueous solution (20 mL), dried (MgSO$_4$), and concentrated in vacuo. The residual oil was solidified upon standing at room temperature in vacuo to afford the desired 4 (2.5 g, 2.78 g theoretical, 90%) as yellow solids, which was found to be pure enough to go directly to the next reaction without further purification. The analytically pure product was obtained as yellow crystals by recrystalization of the crude material from TBME.

Part C 3-(2-Chloro-4,6-dimethyl)phenyl-7-(1,3-dimethoxy-2-propyl)amino-5-methyl-[1,2,3]triazolo[4,5-b]pyridine (5) and 4-(2-Chloro-4,6-dimethyl)phenylamino-1-(1,3-dimethoxy-2-)propyl-6-methyl-[1,2,3]triazolo[4,5-c]pyridine (6)

Method A

A solution of 4 (1.5 g, 4.0 mmol) in CH$_2$Cl$_2$ (10 mL) and HOAc (1.14 mL, 20 mmol, 5.0 equiv) at 0° C. under N$_2$ was treated dropwise with a solution of NaNO$_2$ (331 mg, 4.8 mmol, 1.2 equiv) in H$_2$O (3.0 mL). The reaction mixture was kept at 0–5° C. during the addition of the aqueous NaNO$_2$ solution. The resulting reaction mixture was then warmed gradually to room temperature for an additional 30 min before being treated with H$_2$O (20 mL) and CH$_2$Cl$_2$ (30 mL). The two layers were separated, and the aqueous layer was extracted with CH$_2$Cl$_2$ (2×20 mL). The combined organic extracts were washed with H$_2$O (20 mL), saturated aqueous NaHCO$_3$ solution (2×10 mL), H$_2$O (20 mL), and saturated aqueous NaCl solution (20 mL), dried (MgSO$_4$), and concentrated in vacuo. The oily residue was found to be a mixture of 5 and 6 (3:1, 1.4 g, 1.56 g theoretical, 90%) by $^1$H NMR, which was then separated by flash column chromatography purification (SiO$_2$, 15–30% EtOAc-hexane gradient elution) to afford 5 (967 mg, 62%) and 6 (320 mg, 21%). The analytically pure 5 was obtained by recrystalization of the chromatographically pure material from TBME-heptane (1:4).

Method B

A solution of 4 (1.5 g, 4.0 mmol) in THF (10 mL) was treated with HBF$_4$ (54% solution in ether, 1.3 g, 1.1 mL, 8.0 mmol, 2.0 equiv) at 0° C. under N$_2$, and the resulting mixture was then treated dropwise with isoamyl nitrite (643 mg, 0.74 mL, 6.0 mmol, 1.5 equiv). The reaction mixture was kept at 0–5° C. during the addition of isoamyl nitrite. The resulting reaction mixture was then warmed gradually to room temperature for an additional 30 min before being treated with H$_2$O (20 mL) and TBME (30 mL). The two layers were separated, and the aqueous layer was extracted with TBME (20 mL). The combined organic extracts were washed with H$_2$O (20 mL), saturated aqueous NaHCO$_3$ solution (20 mL), H$_2$O (20 mL), and saturated aqueous NaCl solution (20 mL), dried (MgSO$_4$), and concentrated in vacuo. The residual oil was found gradually solidified upon standing in vacuo at room temperature, which was found to be almost exclusively 5 (5:6>95:5) by 1H NMR. The crude solids were recrystalized from TBME-heptane (1:5) to afford pure 5 (1.45 g, 1.56 g theoretical, 93%) as off-white crystals.

Part D

4-(2-Chloro-4,6-dimethyl)-phenylamino-1-(1,3-dimethoxy-2-)propyl-6-methyl-[1,2,3]triazolo[4,5-c]pyridine (6)

Method A

A solution of 5 (195 mg, 0.5 mmol) in anhydrous DMF (2 mL) was cooled down to 0° C. and treated with NaH (60% disposition in mineral oil, 24 mg, 0.6 mmol, 1.2 equiv) under $N_2$. The resulting reaction mixture was gradually warmed to room temperature for 2 h before being warmed to 70° C. for 2 h. The reaction mixture was then cooled down to room temperature and treated with TBME (20 mL) and $H_2O$ (20 mL). The two layers were separated, and the aqueous layer was extracted with TBME (2×10 mL) The combined organic extracts were washed with $H_2O$ (20 mL), and saturated aqueous NaCl (20 mL), dried ($MgSO_4$), and concentrated in vacuo. The residual oil was solidified upon standing at room temperature in vacuo to afford pure 6 (178 mg, 195 mg theoretical, 92%).

Method B

A solution of mixed 5 and 6 (5:6=3:1, 780 mg, 2.0 mmol) in anhydrous 1-methyl-2-pyrrolidone (NMP, 8 mL) was cooled down to 0° C. and treated with NaH (60% disposition in mineral oil, 96 mg, 2.4 mmol, 1.2 equiv) at 0° C. under $N_2$. The resulting reaction mixture was stirred at 0° C. for 10 min before being warmed to room temperature for overnight. The isomerization was found to be very slow at room temperature, so the reaction mixture was further to warmed to 70° C. for 6 h before the isomerization was completed. The reaction mixture was then cooled down to room temperature and treated with TBME (20 mL) and $H_2O$ (20 mL). The two layers were separated, and the aqueous layer was extracted with TBME (2×20 mL). The combined organic extracts were washed with $H_2O$ (2×20 mL), and saturated aqueous NaCl (20 mL), dried ($MgSO_4$), and concentrated in vacuo. The residual oil was solidified upon standing at room temperature in vacuo to afford pure 6 (726 mg, 780 mg theoretical, 93%). Compound 6 can be converted to the corresponding mesylate salt by the method of Example 259, Part J.

The method of Example 527 can be used to produce other compounds of Formula I wherein X is $CR^1$, Y is N, and Z is $NR^3$, such as the compounds of Examples 221–232, 414 and 414a and the compounds of Table 8.

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 mM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 mg/l aprotinin, 1 mg/ml leupeptin and 1 mg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 mg/ml to be used in the assay.

Binding assays are performed in 96 well plates; each well having a 300 ml capacity. To each well is added 50 ml of test drug dilutions (final concentration of drugs range from $10^{-10}$–$10^{-5}$ M), 100 ml of $^{125}$I-ovine-CRF ($^{125}$I-o-CRF) (final concentration 150 pM) and 150 ml of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity was performed as described by G. Battaglia et al. *Synapse* 1:572 (1987). Briefly, assays were carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6}$m) and 0.8 mg original wet weight tissue (approximately 40–60 mg protein). Reactions were initiated by the addition of 1 mM ATP/$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

Some compounds of this invention were tested in this assay and found to be active.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990)

Compounds may be tested in any species of rodent or small mammal. Disclosure of the assays herein is not intended to limit the enablement of the invention.

Compounds of this invention have utility in the treatment of abnormalities in humans and other mammals which are associated with corticotropin releasing factor and/or a receptor for corticotropin releasing factor. This includes depression, affective disorders, anxiety, irritable bowel syndrome, post-traumatic stress disorder, supranuclear palsy, epilepsy, seizures, immune suppression, Alzheimer's disease, gastrointestinal disease, anorexia nervosa or other feeding disorder, drug or alcohol withdrawal symptoms, drug addiction, inflammatory disorders, fertility problems. It includes numerous other disorders such as those mentioned in the disclosure of Pfizer WO95/33750, at pages 7 and 8, which is incorporated herein by reference.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

What is claimed is:

1. A CRF antagonist compound of formula I:

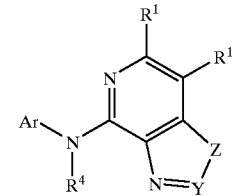

or a pharmaceutically acceptable salt form thereof, wherein:

Y is N or $CR^2$;

Z is $NR^3$, O, or $S(O)_n$;

Ar is naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each optionally substituted with 1 to 5 $R^5$ groups;

$R^1$ is independently at each occurrence H, $C_1$–$C_4$ alkyl, $C_2$–$C_4$ alkenyl, $C_2$–$C_4$ alkynyl, halo, CN, $C_1$–$C_4$ haloalkyl, —$NR^9R^{10}$, $NR^9COR^{10}$, —$OR^{11}$, SH or —$S(O)_nR^{12}$;

$R^2$ is H, $C_1$–$C_4$ alkyl, $C_1$–$C_6$ cycloalkyl, halo, CN, —$NR^6R^7$, $NR^9COR^{10}$, $C_1$–$C_4$ haloalkyl, —$OR^7$, SH or —$S(O)_nR^{12}$;

$R^3$ is H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —NR⁸CO₂R₁₃, —NR⁶R⁷, —CONR⁶R⁷, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —OR⁷, SH, —S(O)$_n$R¹³, —COR⁷, —CO₂R⁷, —OC(O)R¹³, —NR⁸COR⁷, —N(COR⁷)₂, —NR⁸CONR⁶R⁷, —NR⁸CO₂R₁₃, —NR⁶R⁷, and —CONR⁶R⁷;

R⁴ is H, $C_1$–$C_4$ alkyl, allyl, or propargyl, where $C_1$–$C_4$ alkyl, allyl, or propargyl is optionally substituted with $C_3$–$C_6$ cycloalkyl and where $C_1$–$C_4$ alkyl is optionally substituted with, —OR⁷, —S(O)$_n$R¹² or —CO₂R⁷;

R⁵ is independently at each occurrence $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —NO₂, halo, —CN, $C_1$–$C_4$ haloalkyl, —NR⁶R⁷, NR⁸COR⁷, NR⁸CO₂R⁷, —COR⁷ —OR⁷, —CONR⁶R⁷, —CO(NOR⁹)R⁷, CO₂R⁷, or —S(O)$_n$R⁷, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —NO₂, halo, —CN, —NR⁶R⁷, —NR⁶R⁷, NR⁸COR⁷, NR⁸CO₂R⁷, —COR⁷ —OR⁷, —CONR⁶R⁷, CO₂R⁷, —CO(NOR⁹)R⁷, or —S(O)$_n$R⁷;

R⁶ and R7 are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or NR⁶R⁷ is piperidine, pyrrolidine, piperazine, N-methylpiperazine, morpholine or thiomorpholine;

R⁸ is independently at each occurrence H or $C_1$–$C_4$ alkyl;

R⁹ and R¹⁰ are independently at each occurrence selected from H, $C_1$–$C_4$ alkyl, or $C_3$–$C_6$ cycloalkyl;

R¹¹ is H, $C_1$–$C_4$ alkyl, $C_1$–$C_4$ haloalkyl, or $C_3$–$C_6$ cycloalkyl;

R¹² is $C_1$–$C_4$ alkyl or $C_1$–$C_4$ haloalkyl;

R¹³ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —OR⁷, SH, —S(O)$_n$R¹³, —COR⁷, —CO₂R⁷, —OC(O)R¹³, —NR⁸COR⁷, —N(COR⁷)₂, —NR⁸CONR⁶R⁷, —NR⁸CO₂R¹³, —NR⁶R⁷, and —CONR⁶R⁷;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —OR⁷, SH, —S(O)$_n$R¹³, —COR⁷, —CO₂R⁷, —OC(O)R¹³, —NR⁸COR⁷, —N(COR⁷)₂, —NR⁸CONR⁶R⁷, —NR⁸CO₂R¹³, —NR⁶R⁷, and —CONR⁶R⁷;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —OR⁷, SH, —S(O)$_n$R¹³, —COR⁷, —CO₂R⁷, —OC(O)R¹³, —NR⁸COR⁷, —N(COR⁷)₂, —NR⁸CONR⁶R⁷, —NR⁸CO₂R¹³, —NR⁶R⁷, and —CONR⁶R⁷; and n is independently at each occurrence 0, 1 or 2.

2. A CRF antagonist compound of formula I:

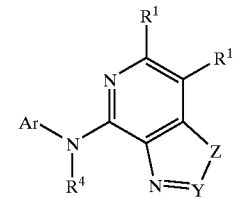

I or a pharmaceutically acceptable salt form thereof, wherein:

Y is CR²;

Z is NR³, O, or S(O)$_n$;

Ar is phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each substituted with 2 to 5 R⁵ groups;

R¹ is independently at each occurrence H, $C_1$–$C_4$ alkyl, $C_2$–$C_4$ alkenyl, $C_2$–$C_4$ alkynyl, halo, CN, $C_1$–$C_4$ haloalkyl, —NR⁹R¹⁰, NR⁹COR¹⁰, —OR¹¹, SH or —S(O)$_n$R¹²;

R² is H, $C_1$–$C_4$ alkyl, $C_1$–$C_6$ cycloalkyl, halo, CN, —NR⁶R⁷, NR⁹COR¹⁰, $C_1$–$C_4$ haloalkyl, —OR⁷, SH or —S(O)$_n$R¹²;

R³ is H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —OR⁷, SH, —S(O)$_n$R¹³, —COR⁷, —CO₂R⁷, —OC(O)R¹³, —NR⁸COR⁷, —N(COR⁷)₂, —NR⁸CONR⁶R⁷, —NR⁸CO₂R¹³, —NR⁶R⁷, —CONR⁶R⁷, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —OR⁷, SH, —S(O)$_n$R¹³, —COR⁷, —CO₂R⁷, —OC(O)R¹³, —NR⁸COR⁷, —N(COR⁷)₂, —NR⁸CONR⁶R⁷, —NR⁸CO₂R¹³, —NR⁶R⁷, and —CONR⁶R⁷;

R⁴ is H, $C_1$–$C_4$ alkyl, allyl, or propargyl, where $C_1$–$C_4$ alkyl, allyl, or propargyl is optionally substituted with $C_3$–$C_6$ cycloalkyl and where $C_1$–$C_4$ alkyl is optionally substituted with, —OR⁷, —S(O)$_n$R¹² or —CO₂R⁷;

R⁵ is independently at each occurrence $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —NO₂, halo, —CN, $C_1$–$C_4$ haloalkyl, —NR⁶R⁷, NR⁸COR⁷, NR⁸CO₂R⁷, —COR⁷ —OR⁷, —CONR⁶R⁷, —CO(NOR⁹)R⁷, CO₂R⁷, or —S(O)$_n$R⁷, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —NO₂, halo, —CN, —NR⁶R⁷, —NR⁶R⁷, NR⁸COR⁷, NR⁸CO₂R⁷, —COR⁷ —OR⁷, —CONR⁶R⁷, CO₂R⁷, —CO(NOR⁹)R⁷, or —S(O)$_n$R⁷;

R⁶ and R⁷ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or NR$^6$R$^7$ is piperidine, pyrrolidine, piperazine, N-methylpiperazine, morpholine or thiomorpholine;

R$^8$ is independently at each occurrence H or C$_1$–C$_4$ alkyl;

R$^9$ and R$^{10}$ are independently at each occurrence selected from H, C$_1$–C$_4$ alkyl, or C$_3$–C$_6$ cycloalkyl;

R$^{11}$ is H, C$_1$–C$_4$ alkyl, C$_1$–C$_4$ haloalkyl, or C$_3$–C$_6$ cycloalkyl;

R$^{12}$ is C$_1$–C$_4$ alkyl or C$_1$–C$_4$ haloalkyl;

R$^{13}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heteroaryl or heteroaryl(C$_1$–C$_4$ alkyl)-;

aryl is phenyl or naphthyl, each optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, and —CONR$^6$R$^7$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, and —CONR$^6$R$^7$;

heterocyclyl is saturated or partially saturated heteroaryl, optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, and —CONR$^6$R$^7$; and n is independently at each occurrence 0, 1 or 2.

3. A CRF antagonist compound of formula I:

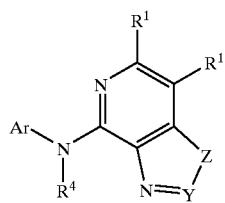

I or a pharmaceutically acceptable salt form thereof, wherein:

Y is N or CR$^2$;

Z is NR$^3$, O, or S(O)$_n$;

Ar is phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each substituted with 2 to 5 R$^5$ groups in imidazopyridine core, and with the proviso that in core involving triazolopyridine Ar will not be trimethyl substituted phenyl;

R$^1$ is independently at each occurrence H, C$_1$–C$_4$ alkyl, C$_2$–C$_4$ alkenyl, C$_2$–C$_4$ alkynyl, halo, CN, —C$_1$–C$_4$ haloalkyl, —NR$^9$R$^{10}$, NR$^9$COR$^{10}$, —OR$^{11}$, SH or —S(O)$_n$R$^{12}$;

R$^2$ is H, C$_1$–C$_4$ alkyl, C$_1$–C$_6$ cycloalkyl, halo, CN, —NR$^6$R$^7$, NR$^9$COR$^{10}$, C$_1$–C$_4$ haloalkyl, —OR$^7$, SH or —S(O)$_n$R$^{12}$;

R$^3$ is H, C$_1$–C$_{10}$ alkyl, C$_2$–C$_{10}$ alkenyl, C$_2$–C$_{10}$ alkynyl, C$_3$–C$_8$ cycloalkyl or C$_4$–C$_{12}$ cycloalkylalkyl each optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, —CONR$^6$R$^7$, aryl, heteroaryl and heterocyclyl, where the aryl, heteroaryl or heterocyclyl is optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, and —CONR$^6$R$^7$;

R$^4$ is H, C$_1$–C$_4$ alkyl, allyl, or propargyl, where C$_1$–C$_4$ alkyl, allyl, or propargyl is optionally substituted with C$_3$–C$_6$ cycloalkyl and where C$_1$–C$_4$ alkyl is optionally substituted with, —OR$^7$, —S(O)$_n$R$^{12}$ or —CO$_2$R$^7$;

R$^5$ is independently at each occurrence C$_2$–C$_{10}$ alkyl, C$_2$–C$_{10}$ alkenyl, C$_2$–C$_{10}$ alkynyl, C$_3$–C$_6$ cycloalkyl, C$_4$–C$_{12}$ cycloalkylalkyl, —NO$_2$, halo, —CN, C$_1$–C$_4$ haloalkyl, —NR$^6$R$^7$, NR$^8$COR$^7$, NR$^8$CO$_2$R$^7$, —COR$^7$ —OR$^7$, —CONR$^6$R$^7$, —CO(NOR$^9$)R$^7$, CO$_2$R$^7$, or —S(O)$_n$R$^7$, where C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are optionally substituted with 1 to 3 substituents independently selected at each occurrence from C$_1$–C$_4$ alkyl, —NO$_2$, halo, —CN, —NR$^6$R$^7$, —NR$^6$R$^7$, NR$^8$COR$^7$, NR$^8$CO$_2$R$^7$, —COR$^7$ —OR$^7$, —CONR$^6$R$^7$, CO$_2$R$^7$, —CO(NOR$^9$)R$^7$, or —S(O)$_n$R$^7$;

R$^6$ and R$^7$ are independently at each occurrence H, C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heteroaryl or heteroaryl(C$_1$–C$_4$ alkyl)-; or NR$^6$R$^7$ is piperidine, pyrrolidine, piperazine, N-methylpiperazine, morpholine or thiomorpholine;

R$^8$ is independently at each occurrence H or C$_1$–C$_4$ alkyl;

R$^9$ and R$^{10}$ are independently at each occurrence selected from H, C$_1$–C$_4$ alkyl, or C$_3$–C$_6$ cycloalkyl;

R$^{11}$ is H, C$_1$–C$_4$ alkyl, C$_1$–C$_4$ haloalkyl, or C$_3$–C$_6$ cycloalkyl;

R$^{12}$ is C$_1$–C$_4$ alkyl or C$_1$–C$_4$ haloalkyl;

R$^{13}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heteroaryl or heteroaryl(C$_1$–C$_4$ alkyl)-;

aryl is phenyl or naphthyl, each optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, and —CONR$^6$R$^7$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from C$_1$–C$_6$ alkyl, C$_3$–C$_6$ cycloalkyl, halo, C$_1$–C$_4$ haloalkyl, cyano, —OR$^7$, SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^{13}$, —NR$^6$R$^7$, and —CONR$^6$R$^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$; and n is independently at each occurrence 0, 1 or 2.

4. A pharmaceutical composition comprising a pharmaceutically acceptable carrier and a therapeutically effective amount of the compound of claim 1.

5. A method of treating anxiety, depression or affective disorder in a mammal which comprises administering to the mammal the pharmaceutical composition of claim 4.

6. A pharmaceutical composition comprising a pharmaceutically acceptable carrier and a therapeutically effective amount of the compound of claim 2.

7. A method of treating anxiety, depression or affective disorder in a mammal which comprises administering to the mammal the pharmaceutical composition of claim 6.

8. A pharmaceutical composition comprising a pharmaceutically acceptable carrier and a therapeutically effective amount of the compound of claim 3.

9. A method of treating anxiety, depression or affective disorder in a mammal which comprises administering to the mammal the pharmaceutical composition of claim 8.

\* \* \* \* \*